US007608272B2

(12) United States Patent
Ansari et al.

(10) Patent No.: US 7,608,272 B2
(45) Date of Patent: *Oct. 27, 2009

(54) METHODS AND COMPOSITIONS FOR VACCINATION OF ANIMALS WITH PRRSV ANTIGENS WITH IMPROVED IMMUNOGENICITY

(75) Inventors: Israrul H. Ansari, Lincoln, NE (US); Fernando A. Osorio, Lincoln, NE (US); Asit K. Pattnaik, Lincoln, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/064,877

(22) PCT Filed: Aug. 30, 2006

(86) PCT No.: PCT/US2006/033990

§ 371 (c)(1),
(2), (4) Date: May 5, 2008

(87) PCT Pub. No.: WO2007/040876

PCT Pub. Date: Apr. 12, 2007

(65) Prior Publication Data

US 2008/0233083 A1     Sep. 25, 2008

Related U.S. Application Data

(60) Provisional application No. 60/712,357, filed on Aug. 30, 2005.

(51) Int. Cl.
*A61K 39/12* (2006.01)
(52) U.S. Cl. .................................. 424/204.1
(58) Field of Classification Search .............. 424/204.1
See application file for complete search history.

(56) References Cited

U.S. PATENT DOCUMENTS 6,268,199 B1    7/2001    Meulenberg et al.
6,500,662 B1    12/2002   Calvert et al.

OTHER PUBLICATIONS

Mardassi et al, Virology, 1996, vol. 221, pp. 98-112.*
Plagemann et al, Archive. Virology, 2002, vol. 147, pp. 2327-2347.*
Wissink et al, Journal of General Virology, 2004, vol. 85, pp. 3715-3723.*
Ansari et al, Journal of Virology, Apr. 2006, vol. 80, No. 8, pp. 3994-4004.*
Pirzadeh et al., "Genomic and Antigenic Variations of Porcine Reproductive and Respiratory Syndrome Virus Major Envelope GP5 Glycoprotein", 1998, Can. J. Vet Res., pp. 170-177, vol. 62.
Pirzadeh et al., "Immune Response in Pigs Vaccinated with Plasmid DNA Encoding ORF5 of Porcine Reproductive and Respiratory Syndrome Virus", 1998, J. General Virology, pp. 989-999, vol. 79.
Wissink et al., "Significance of the Oligosaccharides of the Porcine Reproductive and Respiratory Syndrome Virus Glycoproteins GP2a and GP5 for Infectious Virus Production", 2004, Journal of General Virology, pp. 3715-3723, vol. 85.
Braakman et al., "Folding of Viral Envelope Glycoproteins in the Endoplasmic Reticulum", 2000, Traffic, pp. 533-539, vol. 1.
Shi et al., "Analysis of N-Linked Glycosylation of Hantaan Virus Glycoproteins and the Role of Oligosaccharide Side Chains in Protein Folding and Intracellular Trafficking", 2004, Journal of General Virology, pp. 5414-5422, vol. 78.
Abe et al., "Effect of the Addition of Oligosaccharides on the Biological Activities and Antigenicity of Influenze A/H3N2 Virus Hemagglutinin", 2004, Journal of General Virology, pp. 9605-9611, vol. 78.
Skehel et al., "A Carbohydrate Side Chain on Hemagglutinins of Hong Kong Influenza Viruses Inhibits Recognition by a Monoclonal Antibody", 1984, Proc. Natl. Acad. Sci. USA, pp. 1779-1783, vol. 81.
Wei et al., "Antibody Neutralization and Escape by HIV-1", 2003, Letters to Nature, pp. 307-312, vol. 422.
Lee et al., "The Influence of Glycosylation on Secretion, Stability, and Immunogenicity of Recombinant HBV pre-S Antigen Synthesized in Saccharomyces Cerevisiae", 2003, Biochemical and Biophysical Research Communications, pp. 427-432, vol. 303.
Chen et al., "Neuropathogenicity and Sensitivity to Antibody Neutralization of Lactate Dehydrogenase Elevating Virus Are Determined by Polylactosaminoglycan Chains on the Primary Envelope Glycoprotein", 2000, Virology, pp. 88-98, vol. 266.
Reitter et al., "A Role For Carbohydrates in Immune Evasion in AIDS", 1998, Nature Medicine, pp. 679-684, vol. 4.
Doms et al., "Folding and Assembly of Viral Membrane Proteins", 1993, Virology, pp. 545-562, vol. 193.
Mardassi et al., "Intracellular Synthesis, Processing, and Transport of Proteins Encoded by ORFs 5 to 7 of Porcine Reproductive and Respiratory Syndrome Virus," 1996, Virology, pp. 98-112, vol. 221.
Kwang et al., "Antibody and Cellular Immune Responses of Swine Following Immunisation with Plasmid DNA Encoding the PRRS Virus ORF's 4, 5, 6 and 7", Research in Veterinary Science, 1999, pp. 199-201, vol. 67.

(Continued)

*Primary Examiner*—Ali R. Salimi
(74) *Attorney, Agent, or Firm*—Thompson Coburn LLP; Charles P. Romano

(57) ABSTRACT

Pigs challenged with hypoglycosylated variants of Porcine Reproductive and Respiratory Syndrome Virus (PRRSV) major surface protein GP5 exhibited increased production of PRRSV-neutralizing antibodies relative to the levels of neutralizing antibodies produced by pigs immunized with wild type (wt) or glycosylated GP5. This invention provides for methods of obtaining improved immune responses in pigs to PRRSV, compositions useful for obtaining the improved immune responses as well as isolated polynucleotides that encode hypoglycosylated variants of PRRSV major surface protein GP5.

29 Claims, 6 Drawing Sheets

OTHER PUBLICATIONS

Madsen et al., "Sequence Analysis of Porcine Reproductive and Respiratory Syndrome Virus of the American Type Collected from Danish Swine Herds", Archives of Virology, 1998, pp. 1683-1700, vol. 143.

European Communication dated Apr. 8, 2009 attaching Supplementary European Search Report for European Regional Phase Application No. 06824866.5 dated Mar. 9, 2009.

* cited by examiner

FIG. 1A
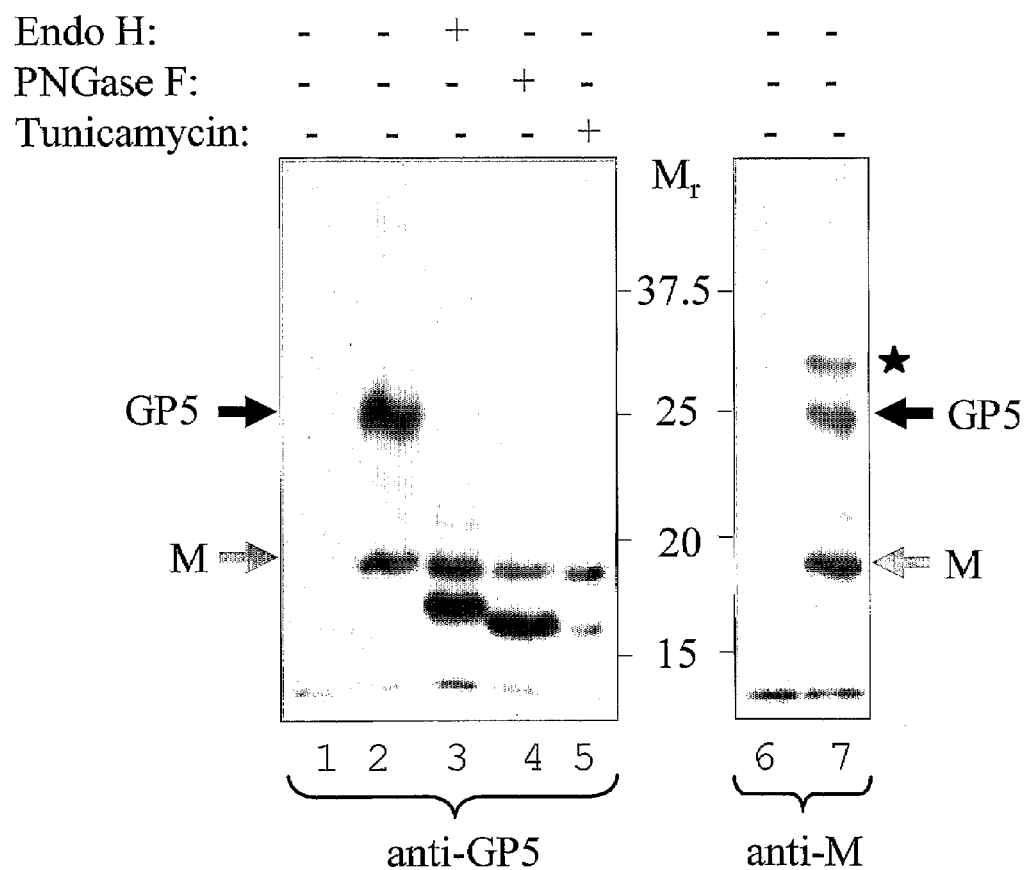
FIG. 1B

FIG. 2A
FIG. 2B
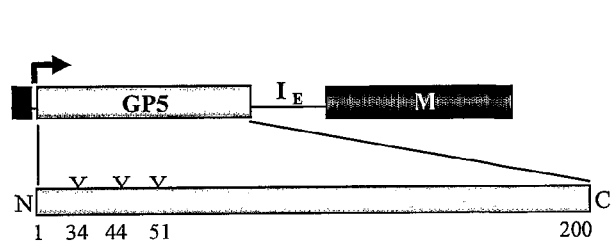
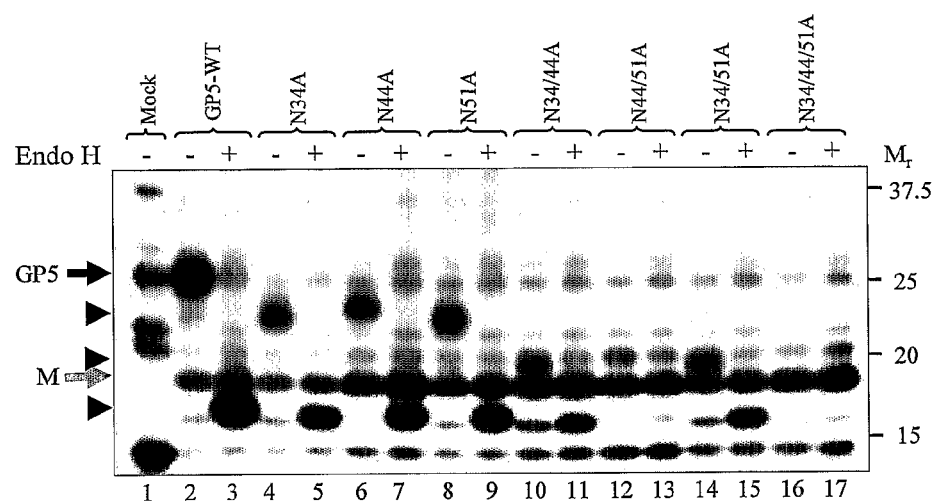
FIG. 2C

```
        M L G K C L T A G C C S Q L P F L W C I V P F C F A A L V N  Majority
                        10                  20                  30
                        +                   +                   +
   1    M L G R C L T A G C C S R L L S L W C I V P F C F A A L V N  SEQ ID NO:1
   1    M L G K C L T A G C C S Q L P F L W C I V P F C F A A L V N  SEQ ID NO:2
   1    M L G K C L T A G C C S Q L P F L W C I V P F C F A A L V N  SEQ ID NO:3
   1    M L G K C L T V G Y C S Q L P F L W C I V P F C F A A L V N  SEQ ID NO:4
   1    M L G K C L T A G C C S Q L P F L W C I V P F C F V A L V N  SEQ ID NO:5
   1    M L G K C L T A G C C S R L P F L W C I V P F C F A A L V N  SEQ ID NO:6
   1    M L G K C L T A G C C S R L P F L W C I V P F C F A V L V N  SEQ ID NO:7
   1    M L G K C L T A G C C S Q L P F L W C I V P F C F A A L V N  SEQ ID NO:8
   1    M L G K C L T A G C C S Q L P F L W C I V P F C F A A L V N  SEQ ID NO:9
   1    M L G K C L T A G C C S Q L L F L W C I V P S W F V A L V S  SEQ ID NO:10
   1    M L E K C L T A G C C S R L L S L W C I V P F C F A V L A N  SEQ ID NO:11
   1    M L G K C L T A G C C S Q L L F L W C I V P S C F V A L V S  SEQ ID NO:12
   1    M L E K C L T A G C C S Q L L S L W C I V P F C F A V L A N  SEQ ID NO:13

A S N N S S S H L Q L I Y N L T I C E L N G T D W L N D K F  Majority
                        40                  50                  60
        ----------------+-------------------+-------------------+-
  31    A N S N S S S H L Q L I Y N L T L C E L N G T D W L K D K F  SEQ ID NO:1
  31    A S S S S S S Q L Q S I Y N L T I C E L N G T D W L N K N F  SEQ ID NO:2
  31    A S N N S S S Q L Q S I Y N L T I C E L N G T D W L N K N F  SEQ ID NO:3
  31    A S S T S S S H L Q L I Y N L T I C E L N G T D W L N E K F  SEQ ID NO:4
  31    A S N S S S S H L Q L I Y N L T L C E L N G T D W L D K K F  SEQ ID NO:6
  31    A S P N S S S H L Q L I Y N L T I C E L N G T D W L N A R F  SEQ ID NO:7
  31    A S N N S S S H L Q L I Y N L T I C E L N G T D W L N D K F  SEQ ID NO:8
  31    A S S S S S S Q L Q S I Y N L T I C E L N G T D W L N K N F  SEQ ID NO:9
  31    A S N S S S S H L Q L I Y N L T L C E L N G T D W L A D K F  SEQ ID NO:10
  31    A S N D S S S H L Q L I Y N L T L C E L N G T D W L A N K F  SEQ ID NO:11
  31    A N G N S G S N L Q L I Y N L T L C E L N G T D W L A N K F  SEQ ID NO:12
  31    A S N D S S S H L Q L I Y N L T L C E L N G T D W L A N K F  SEQ ID NO:13
```

FIG. 5

```
        M R C S H K L G R F L T A G S C S R L L S L L C I V P F C F  Majority
                         10                  20                  30
        ------------------+-------------------+------------------+-
    1   M - - - - - L G R C L T A G C C S R L L S L W C I V P F C F  SEQ ID NO:1
    1   M R C S H K L G R F L T P H S C F W W L F L L C - - - - - -  SEQ ID NO:15

A G L V W S F A A G S G S S S T L Q L I Y N L T L C E L N G  Majority
                         40                  50                  60
        ------------------+-------------------+------------------+-
   26   A A L V - - - N A N S N S S S H L Q L I Y N L T L C E L N G  SEQ ID NO:1
   25   T G L S W S F A D G N G D S S T Y Q Y I Y N L T I C E L N G  SEQ ID NO:15

T D W L S S K F G W A V E T F V L F P V A T H I V S L G A L  Majority
                         70                  80                  90
        ------------------+-------------------+------------------+-
   53   T D W L K D K F D W A V E T F V I F P V L T H I V S Y G A L  SEQ ID NO:1
   55   T D W L S S H F G W A V E T F V L Y P V A T H I L S L G F L  SEQ ID NO:15

T T S H F L D A V G L G A V S T A G F V G G R Y V L S S V Y  Majority
                        100                 110                 120
        ------------------+-------------------+------------------+-
   83   T T S H F L D T V G L V T V S T A G F Y H G R Y V L S S I Y  SEQ ID NO:1
   85   T T S H F F D A L G L G A V S T A G F V G G R Y V L C S V Y  SEQ ID NO:15

G A C A L A A L V C F V I R A A K N C M A W R Y A R T R F T  Majority
                        130                 140                 150
        ------------------+-------------------+------------------+-
  113   A V C A L A A L I C F V I R L A K N C M S W R Y S C T R Y T  SEQ ID NO:1
  115   G A C A F A A F V C F V I R A A K N C M A C R Y A R T R F T  SEQ ID NO:15

N F L V D T K G R V H R W K S P V V V E K G G K A E V D G N  Majority
                        160                 170                 180
        ------------------+-------------------+------------------+-
  143   N F L L D T K G R L Y R W R S P V I I E K G G K V E V E G H  SEQ ID NO:1
  145   N F I V D D R G R V H R W K S P I V V E K L G K A E V D G N  SEQ ID NO:15

L V T L K H V V L D G V V A T P L T R V S A E Q W G A L      Majority
                        190                 200
        ------------------+-------------------+-------------------
  173   L I D L K R V V L D G S V A T P L T R V S A E Q W G R L      SEQ ID NO:1
  175   L V T I K H V V L E G V K A Q P L T R T S A E Q W E A        SEQ ID NO:15
```

FIG. 6

METHODS AND COMPOSITIONS FOR VACCINATION OF ANIMALS WITH PRRSV ANTIGENS WITH IMPROVED IMMUNOGENICITY

CROSS-REFERENCE TO RELATED APPLICATIONS

This application claims priority to U.S. Provisional Patent Application No. 60/712,357, filed on Aug. 30, 2005.

STATEMENT REGARDING FEDERALLY SPONSORED RESEARCH OR DEVELOPMENT

This invention was made with Government support under a National Research Initiative Competitive Grant #2004-01576 from the U.S. Department of Agriculture and under a National Institute of Health COBRE program of the National Center for Research Resources Project #P20RR15636. The government has certain rights to this invention.

APPENDIX

Not Applicable

BACKGROUND OF THE INVENTION

1. Field of the Invention

This invention relates generally to compositions comprising Porcine Reproductive and Respiratory Syndrome Virus (PRRSV) antigens with improved immunogenicity and methods for their use. The compositions and methods described herein result in improved immunogenic responses of pigs to PRRSV antigens, thus providing for improved protection of pigs to PRRSV infection.

2. Related Art

PRRSV is an economically important pathogen that affects pigs. Infection of sows and gilts with PRRSV can result in reproductive failure. PRRSV also causes respiratory disease in pigs of all ages. It is possible to vaccinate the pigs to protect them from infection with PRRSV. However, the current commercially available vaccines (most of which are live attenuated vaccines) are somewhat ineffective and therefore should be improved. The complete immunologic mechanisms of protection against PRRSV are not clear; however, it has been clearly shown that PRRSV-neutralizing antibodies are central to this protection. Unfortunately, the PRRSV itself (in its wild-type form) or the current live vaccines derived from it have poor ability to induce virus-specific neutralizing antibodies in a timely manner and at effective (i.e., protective) levels.

U.S. Pat. No. 6,500,662, "Infectious cDNA clone of North American porcine reproductive and respiratory syndrome (PRRS) virus and uses thereof" (by Calvert et al., Dec. 31, 2002) describes the development of an infectious North American PRRSV cDNA clone and its use as a vaccine. However, U.S. Pat. No. 6,500,662 does not disclose PRRSV vaccines that comprise hypoglycosylated PRRSV antigens.

In another study, sequences of the GP5 protein (or ORF5 protein) from various North American PRRSV strains were compared to one another and to the representative European PRRSV isolate known as the Lelystad strain, revealing that the N-linked glycosylation sites at Asparagine 44 (N44) and Asparagine 51 (N51) of the GP5 consensus sequence were conserved in all of the PRRSV isolates examined (Pirzadeh et al., Can. J. Vet Res., 1998, 62:170-177). However, the N-glycosylation site located at Asparagine 31 (N31) of the GP5 consensus sequence was absent in certain North American PRRSV isolates and absent in the European PRRSV Lelystad strain isolate. Recombinant GST-GP5 fusion proteins from four (4) North American PRRSV strains and the Leylstad strain were produced in $E.\ coli$ as insoluble inclusion bodies, renatured, and used as immunogens in rabbits. Such recombinant proteins produced in $E.\ coli$ retain but do not glycosylate their native N-glycosylation sites.

Inoculation of pigs with a DNA vaccine comprising a CMV promoter fusion to the GP5 gene of the IAF-Klop North American PRRSV isolate has also been shown to provide protection in immunized animals against PRRSV challenge (Pirzadeh and Dea, 1998, J. General Virology, 79, 989-999). This particular GP5 gene isolate encodes a GP5 protein containing the N31, N44 and N51 Asparagine residues that are presumably glycosylated when expressed in pigs immunized with the DNA vaccine. Vaccination of pigs with $E.\ coli$ produced GST-GP5, which retain but do not glycosylate the native N-glycosylation sites of the GP5 gene of the IAF-Klop strain, did not protect the lungs of virus-challenged pigs.

European PRRSV infectious clones containing mutations that result in expression of hypoglycosylated PRRSV proteins have also been described (Wissink et al., 2004, J. Gen. Virol. 85:3715-23). This particular reference reports that PRRSV containing mutations in the Asparagine Residue 53 (N53) of the PRRSV Lelystad strain GP(5) protein that prevent N-linked glycosylation of that site are infectious and can produce infectious PRRSV Lelystad strain virus particles. In contrast, PRRSV containing mutations in the N46 of the PRRSV Lelystad strain GP(5) protein that prevent N-linked glycosylation of that site are not infectious and do not produce infectious PRRSV Lelystad strain virus particles. Wissink et al. speculate that N-glycan sites in the European PRRSV $GP_{2a}$ protein, and, by analogy, the N53 site of the GP5 protein, could act at many different levels in the natural host, including receptor interactions or immune shielding.

In viruses other than PRRSV, glycan residues have been implicated in a variety of roles. The N-linked glycosylation, in general, is important for correct folding, targeting, and biological activity of proteins (Helenius, A. and M. Aebi., Annu. Rev. Biochem. 73:1019-1049, 2004; Williams, D. B. and Glycoconj J., 12:iii-iv, 1995; Zhang, et al., Glycobiology 14:1229-46, 2004). In many enveloped viruses, the envelope proteins are modified by addition of sugar moieties and the N-linked glycosylation of envelope protein plays diverse functions of viral glycoproteins such as receptor binding, membrane fusion, penetration into cells, and virus budding (Braakman, I. and E. van Anken, Traffic 1:533-9, 2000; Doms et al. Virology 193:545-62, 1993). Recent studies have demonstrated the role of N-linked glycosylation of Hantaan virus glycoprotein in protein folding and intracellular trafficking (Shi, X. and R. M. Elliott, J. Virol. 78:5414-22, 2004) as well as in biological activity and antigenicity of influenza virus hemagglutinin (HA) protein (Abe, Y., et al., J. Virol. 78:9605-11, 2004). Furthermore, it has become evident that glycosylation of viral envelope proteins is a major mechanism for viral immune evasion and persistence used by several different enveloped viruses to escape, block or minimize the virus-neutralizing antibody response. Examples of this effect have been reported for SIV (Reitter, J. N. et al., Nat. Med. 4:679-84, 1998) and HIV-1 (Wei, X. et al., Nature 422:307-12, 2003), HBV (Lee, J. et al. Biochem. Biophys. Res. Commun. 303:427-32, 2003), influenza (Skehel, J. J. et al., Proc. Natl.

Acad. Sci. USA 81:1779-83, 1984) and the arterivirus LDV (Chen, Z. et al. Virology 266:88-98, 2000).

SUMMARY OF THE INVENTION

It is in view of the above problems that the present invention was developed. It is demonstrated that hypoglycosylated variants of a PRRSV major surface protein GP5 increased the level of PRRSV-neutralizing antibodies produced by immunized pigs relative to the levels of neutralizing antibodies produced by pigs immunized with wild type (wt) or glycosylated GP5.

This invention first provides for a method of eliciting an improved immune response in a pig to a Porcine Reproductive and Respiratory Syndrome Virus (PRRSV) antigen, comprising the administration of a composition comprising a polynucleotide encoding a hypoglycosylated PRRSV GP5 polypeptide variant wherein at least one N-linked glycosylation site corresponding to asparagine 34 or asparagine 51 in a reference GP5 protein of SEQ ID NO:1 is inactivated. In certain embodiments of the method, at least one N-linked glycosylation site corresponding to asparagine 34 or asparagine 51 in SEQ ID NO:1 is inactivated. This polynucleotide can comprise an infectious PRRSV RNA molecule or a DNA molecule that encodes an infectious PRRSV RNA molecule. The infectious PRRSV RNA molecule is a North American PRRSV derivative or a European PRRSV derivative. Alternatively, this polynucleotide can comprise a DNA molecule wherein a promoter active in mammalian cells is operably linked to said polynucleotide encoding a hypoglycosylated GP5 protein. This promoter is a CMV promoter in certain preferred embodiments of the invention. Alternatively, the polynucleotide can be a viral vector. Representative viral vectors that can be used include vaccinia virus vectors, a herpes simplex viral vectors, adenovirus vectors, alphavirus vectors, and TGEV vectors.

A variety of types and sources of PRRSV sequences can be used to obtain the polynucleotide encoding a hypoglycosylated PRRSV GP5 polypeptide variant wherein at least one N-linked glycosylation site corresponding to asparagine 34 or asparagine 51 in a reference GP5 protein of SEQ ID NO:1 is inactivated. In certain embodiments of the invention, a polynucleotide encoding a hypoglycosylated PRRSV GP5 polypeptide variant is obtained by direct synthesis, mutagenesis of a North American PRRSV isolate GP5 nucleotide sequence or mutagenesis of a consensus North American PRRSV GP5 nucleotide sequence. The North American PRRSV isolate GP5 nucleotide sequence can be selected from the group of nucleotides that encode the GP5 proteins of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, and SEQ ID NO:13. The consensus North American PRRSV GP5 nucleotide sequence encodes a consensus GP5 protein that is at least 85% identical to SEQ ID NO:14. In other embodiments of the invention, the polynucleotide encoding a hypoglycosylated PRRSV GP5 polypeptide variant is obtained by direct synthesis, mutagenesis of a European PRRSV isolate GP5 nucleotide sequence or mutagenesis of a consensus European PRRSV GP5 nucleotide sequence. The European PRRSV isolate GP5 nucleotide sequence encodes a GP5 protein that is at least 85% identical to SEQ ID NO:15.

A variety of methods of inactivating specified N-linked glycosylation sites can be used to effectively practice the method of this invention. One preferred method of inactivating an N-linked glycosylation site corresponding to asparagine 51 is to replace the asparagine codon with a codon encoding an amino acid other than asparagine. This replacement codon can encode an alanine or a glutamine residue. In more preferred embodiments, both of said N-linked glycosylation sites corresponding to asparagine 34 and asparagine 51 in a reference GP5 protein of SEQ ID NO:1 are inactivated. In other embodiments, the N-linked glycosylation site corresponding to asparagine 34 is inactivated. This asparagine 34 N-linked glycosylation site can be inactivated by replacing a codon encoding said asparagine 34 with a codon encoding an amino acid other than asparagine. The codon encoding another amino acid can encode an alanine or a glutamine residue. In other preferred embodiments, both of the N-linked glycosylation sites corresponding to asparagine 34 and asparagine 51 in a reference GP5 protein can be inactivated by replacing codons encoding the asparagine 34 and the asparagine 51 with codons encoding an amino acid other than asparagine. Both codons encoding the asparagine 34 and the asparagine 51 can be replaced with codons encoding either an alanine or a glutamine residue to inactivate those glycosylation sites. Alternatively, both codons can be replaced with codons that encode an alanine residue to inactivate both glycosylation sites. Alternatively, one of the N-linked glycosylation sites is inactivated by replacing one codon encoding said asparagine 34 or said asparagine 51 with a codon encoding an amino acid other than asparagine while the other N-linked glycosylation site is inactivated by other techniques.

In preferred embodiments, the method employs an infectious PRRSV RNA molecule that is a North American PRRSV derivative encoding a hypoglycosylated PRRSV GP5 polypeptide variant protein wherein at least one N-linked glycosylation site corresponding to asparagine 34 or asparagine 51 in a reference GP5 protein of SEQ ID NO:1 is inactivated. In more preferred embodiments, both of said N-linked glycosylation sites corresponding to asparagine 34 and asparagine 51 in a reference GP5 protein of SEQ ID NO:1 are inactivated. Both of the N-linked glycosylation sites corresponding to asparagine 34 and asparagine 51 in a reference GP5 protein can be inactivated by replacing codons encoding the asparagine 34 and the asparagine 51 with codons encoding an amino acid other than asparagine. Both codons encoding the asparagine 34 and the asparagine 51 can be replaced with codons encoding either an alanine or a glutamine residue to inactivate those glycosylation sites. Alternatively, both codons can be replaced with codons that encode an alanine residue to inactivate that glycosylation site.

To practice this method, the polynucleotide containing composition is administered by subcutaneous injection, intravenous injection, intradermal injection, parenteral injection, intramuscular injection, needle free injection, electroporation, oral delivery, intranasal delivery, oronasal delivery, or any combination thereof. The administered composition can further comprise a therapeutically acceptable carrier. This therapeutically acceptable carrier is selected from the group consisting of a protein, a buffer, a surfactant, and a polyethylene glycol polymer, or any combination thereof.

The administered composition can further comprise an adjuvant. This adjuvant can be aluminum hydroxide, Quil A, an alumina gel suspension, mineral oils, glycerides, fatty acids, fatty acid by-products, mycobacteria, and CpG oligodeoxynucleotides, or any combination thereof. The administered composition can also comprise a second adjuvant such as interleukin 1 (IL-1), IL-2, IL4, IL-5, IL6, IL-12, gamma interferon (g-IFN), cell necrosis factor, MDP (muramyl dipeptide), immuno stimulant complex (ISCOM), and liposomes.

The improved immune response of a pig to a PRRSV antigen can comprise increased production of PRRSV neutralizing antibodies by said pig. Increased production of PRRSV neutralizing antibodies is typically observed upon immunization of the pig by the methods and compositions of this invention. The improved immune response can be obtained in a sow, a gilt, a boar, or a piglet.

The invention also provides a method of eliciting an improved immune response in a pig to a Porcine Reproductive and Respiratory Syndrome Virus (PRRSV) antigen, comprising the administration of a composition comprising a hypoglycosylated PRRSV GP5 polypeptide variant wherein at least one N-linked glycosylation site corresponding to asparagine 34 or asparagine 51 in a reference GP5 protein of SEQ ID NO:1 is inactivated to said pig. Hypoglycosylated PRRSV GP5 polypeptide variant protein can be produced by the same polynucleotides used in the previously described methods in bacterial, yeast, or mammalian expression systems.

The instant invention also provides for compositions comprising a polynucleotide encoding a hypoglycosylated North American PRRSV GP5 polypeptide variant wherein at least one N-linked glycosylation site corresponding to asparagine 51 in a reference GP5 protein of SEQ ID NO:1 is inactivated, and a therapeutically acceptable carrier. In certain embodiments, the compositions comprise polynucleotides where both N-linked glycosylation sites corresponding to asparagine 34 and asparagine 51 in SEQ ID NO:1 are inactivated. In preferred embodiments, this composition can comprise either an infectious North American PRRSV RNA molecule or a DNA molecule that encodes an infectious North American PRRSV RNA molecule. In other embodiments, the polynucleotide comprises a DNA molecule wherein a promoter active in mammalian cells is operably linked to said polynucleotide encoding said hypoglycosylated North American PRRSV GP5 polypeptide variant. In certain preferred embodiments, this promoter is a CMV promoter. In still other embodiments, the polynucleotide in the composition comprises a viral vector. Viral vectors that can be used in the composition can be any one of a vaccinia virus vector, a herpes simplex viral vector, an adenovirus vector, an alphavirus vector, and a TGEV vector.

In the polynucleotides of the composition, an N-linked glycosylation site is inactivated by replacing a codon encoding said asparagine 51 with a codon encoding an amino acid other than asparagine. The codon encoding an amino acid other than asparagine encodes an alanine or a glutamine residue. In other embodiments of this composition, an additional N-linked glycosylation site is inactivated by replacing a codon encoding asparagine 34 with a codon encoding an amino acid other than asparagine. This codon encoding another amino acid can encode an alanine or a glutamine residue. Preferred compositions comprising polynucleotides encoding a hypoglycosylated North American PRRSV GP5 polypeptide variant protein wherein both of said N-linked glycosylation sites corresponding to asparagine 34 and asparagine 51 in a North American reference GP5 protein of SEQ ID NO:1 are inactivated are thus provided for by this application. Both of the said N-linked glycosylation sites can be inactivated by replacing codons encoding said asparagine 34 and said asparagine 51 with codons encoding an amino acid other than asparagine. These codons encoding an amino acid other than asparagine can encode either an alanine or a glutamine residue.

The therapeutically acceptable carrier used in the composition can be a protein, a buffer, a surfactant, and a polyethylene glycol polymer, or any combination thereof. The composition further comprises at least one adjuvant.

This adjuvant can be aluminum hydroxide, Quil A, an alumina gel suspension, mineral oils, glycerides, fatty acids, fatty acid by-products, mycobacteria, and CpG oligodeoxynucleotides, or any combination thereof. The composition can further comprise a second adjuvant selected from the group consisting of interleukin 1 (IL-1), IL-2, IL4, IL-5, IL6, IL-12, gamma interferon (g-IFN), cell necrosis factor, MDP (muramyl dipeptide), immuno stimulant complex (ISCOM), and liposomes.

A composition comprising a hypoglycosylated North American PRRSV GP5 polypeptide variant wherein at least one N-linked glycosylation site corresponding to asparagine 51 in a reference GP5 protein of SEQ ID NO:1 is inactivated and a therapeutically acceptable carrier is also provided by this invention. In preferred embodiments, N-linked glycosylation sites corresponding to both asparagine 34 or asparagine 51 in a reference GP5 protein of SEQ ID NO:1 are inactivated. Hypoglycosylated PRRSV GP5 polypeptide variant protein can be produced by the same polynucleotides used in the previously described methods in bacterial, yeast, or mammalian expression systems.

The instant invention also provides isolated polynucleotides encoding a hypoglycosylated North American PRRSV GP5 polypeptide variant wherein at least one N-linked glycosylation site corresponding to asparagine 51 in a reference GP5 protein of SEQ ID NO:1 is inactivated. In certain embodiments, polynucleotides where both N-linked glycosylation sites corresponding to asparagine 34 and asparagine 51 in SEQ ID NO:1 are inactivated are provided. In preferred embodiments, this isolated polynucleotide can comprise either an infectious North American PRRSV RNA molecule or a DNA molecule that encodes an infectious North American PRRSV RNA molecule. In other embodiments, the isolated polynucleotide comprises a DNA molecule wherein a promoter active in mammalian cells is operably linked to said polynucleotide encoding said hypoglycosylated North American PRRSV GP5 polypeptide variant. In certain preferred embodiments, this promoter is a CMV promoter. In still other embodiments, the isolated polynucleotide comprises a viral vector. Viral vectors that can be used in the composition can be any one of a vaccinia virus vector, a herpes simplex viral vector, an adenovirus vector, an alphavirus vector, and a TGEV vector.

In the isolated polynucleotides an N-linked glycosylation site is inactivated by replacing a codon encoding said asparagine 51 with a codon encoding an amino acid other than asparagine. The codon encoding an amino acid other than asparagine encodes an alanine or a glutamine residue. In other preferred embodiments, an additional N-linked glycosylation site is inactivated by replacing a codon encoding asparagine 34 with a codon encoding an amino acid other than asparagine. This codon encoding another amino acid can encode an alanine or a glutamine residue. Preferred polynucleotides encoding a hypoglycosylated North American PRRSV GP5 polypeptide variant protein wherein both of said N-linked glycosylation sites corresponding to asparagine 34 and asparagine 51 in a North American reference GP5 protein of SEQ ID NO:1 are inactivated are thus provided. Both of the said N-linked glycosylation sites can be inactivated by replacing codons encoding said asparagine 34 and said asparagine 51 with codons encoding an amino acid other than asparagine. These codons encoding an amino acid other than asparagine can encode either an alanine or a glutamine residue.

The invention also provides for an isolated polypeptide that is a hypoglycosylated North American PRRSV GP5 polypeptide variant wherein at least one N-linked glycosylation site corresponding to asparagine 51 in a reference GP5 protein of SEQ ID NO:1 is inactivated. The isolated hypoglycosylated PRRSV GP5 polypeptide variant protein can be produced by the same polynucleotides used in the previously described methods in bacterial, yeast, or mammalian expression systems and purified by chromatography or other techniques.

Further features and advantages of the present invention, as well as the structure and operation of various embodiments of the present invention, are described in detail below with reference to the accompanying drawings.

BRIEF DESCRIPTION OF THE DRAWINGS

The accompanying drawings, which are incorporated in and form a part of the specification, illustrate the embodiments of the present invention and together with the description, serve to explain the principles of the invention. In the drawings:

FIG. 1 illustrates the transient Expression of PRRSV GP5 and M protein. A. Schematic of the bicistronic construct showing the GP5 and M coding regions flanking the IRES (IE) from encephalomyocarditis virus. The coding regions are under the control of T7 RNA polymerase promoter (black rectangle) present immediately upstream of the GP5 coding region. The bent arrow shows the position and direction of transcription by T7 RNA polymerase from the vector. B. Expression of GP5 and M proteins in cells transfected with the bicistronic vector. Mock-transfected (lane 1) or plasmid transfected cells (lanes 2-7) were radiolabeled as described in Materials and Methods, immunoprecipitated with anti-Gp5 antibody (lanes 1-5) or anti-M antibody (lanes 6-7). Immunoprecipitated proteins were left untreated (−) (lanes 1, 2, 6, and 7) or treated (+) with Endo H (lane 3), PNGase F (lane 4) and analyzed by electrophoresis. Lane 5 contains immunoprecipitated proteins from transfected cells treated (+) with tunicamycin. Mobility of proteins with relative molecular mass (Mr) in kilodaltons are shown.

FIG. 2 illustrates the glycosylation analysis of WT-GP5 and its mutants using a bicistronic plasmid. A. Schematic of the bicistronic vector and the PRRSV GP5 with the three putative glycosylation sites at amino acid positions 34, 44 and 51 shown. B. Various mutants used in the present study. C. Expression of wt and mutant GP5 and their sensitivity to Endo H. The experiment was performed as described in the legend to FIG. 1, proteins were immunoprecipitated with anti-GP5 antibody, digested with Endo H (+) or left undigested (−) and analyzed by electrophoresis. Mutant GP5 proteins are shown by arrowheads. Mobility of proteins with relative molecular mass (Mr) in kilodaltons are shown on right.

FIG. 5 illustrates an alignment of North American PRRSV GP5 n-terminal amino acid sequences with the North American PRRSV GP5 reference n-terminal sequence (SEQ ID NO:1; strain NVSL 97-7895). The first 60 N-terminal amino acids of an alignment of the 200 amino acid proteins are shown. The asparagine 34 "NSS" and asparagine 51 "NGT" N-linked glycosylation sites in the proteins are shown in bold. Other N-linked glycosylation sites located between residues 29 and 35 of the reference GP5 protein are underlined.

FIG. 6 illustrates an alignment of European PRRSV GP5 N-terminal amino acid sequence with the North American PRRSV GP5 reference n-terminal sequence (SEQ ID NO:1; strain NVSL 97-7895). An alignment of the entire GP5 protein of approximately 200 amino acid proteins is shown where the asparagine 51 "NGT" N-linked glycosylation site in the proteins is shown in bold (i.e., asparagine 53 in SEQ ID NO:15).

DETAILED DESCRIPTION OF THE PREFERRED EMBODIMENTS

Definitions

Figures 3A, 3B, 3C:
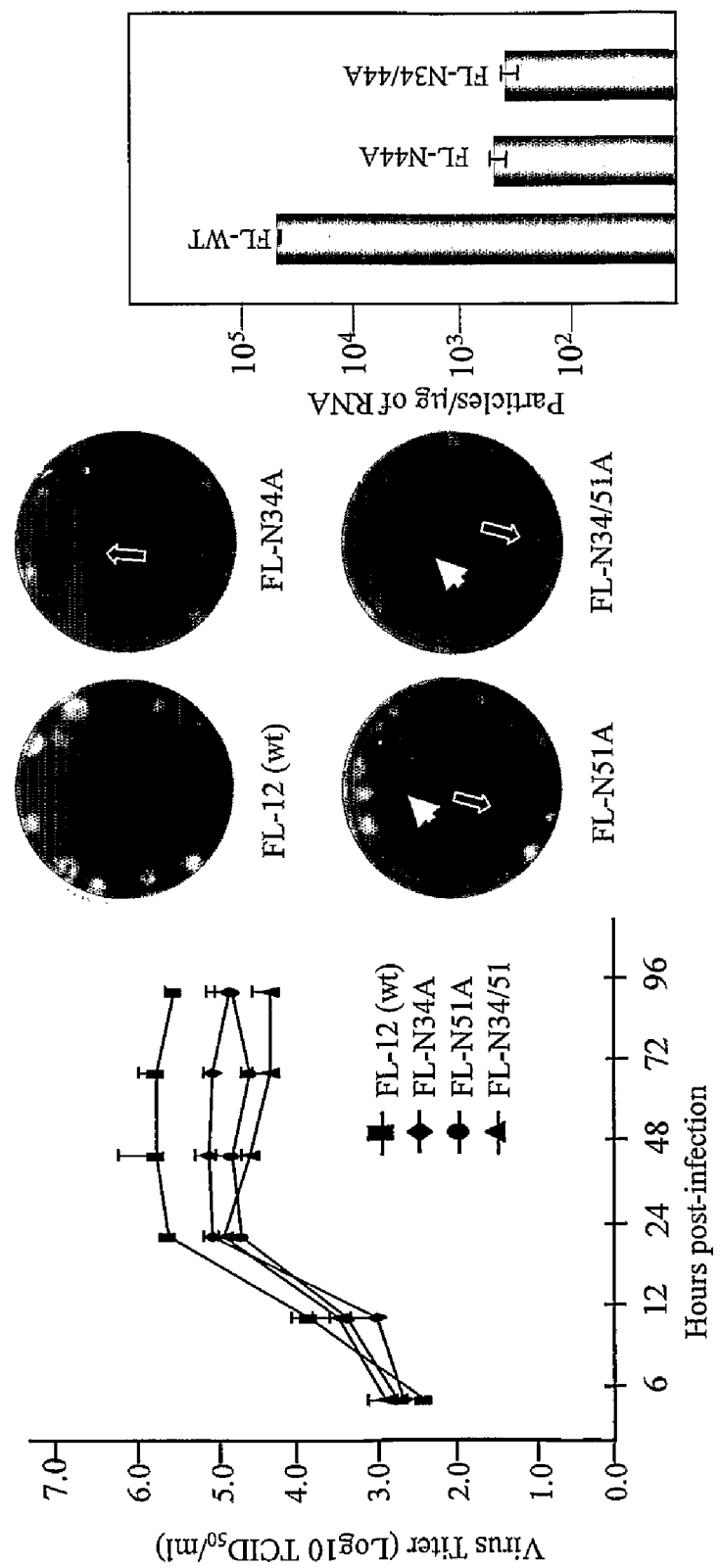
FIG. 3 illustrates the characterization of mutant viruses encoding mutant GP5. A. Single step growth kinetics of wt (FL-12) and various mutant PRRSVs in MARC-145 cells. Cells in six-well plated were infected with PRRSV at an MOI of 3, culture supernatants were collected at indicated times after infection and virus titers were determined. Average titers with standard deviation (error bars) from three independent experiments are shown. B. Plaque morphology of mutant viruses. Open arrows and arrowheads show plaques that are less clear. C. Trans-complementation to recover mutant PRRSVs. Quantitative analysis of mutant virus recovery from cells expressing wt GP5 protein. Average yield of viruses from three independent experiments with standard deviation (represented by error bars) is shown.

"Acceptable carrier", as used herein, refers to a carrier that is not deleterious to the other ingredients of the composition and is not deleterious to material to which it is to be applied. "Therapeutically acceptable carrier" refers to a carrier that is not deleterious to the other ingredients of the composition and is not deleterious to the human or other animal recipient thereof. In the context of the other ingredients of the composition, "not deleterious" means that the carrier will not react with or degrade the other ingredients or otherwise interfere with their efficacy. Interference with the efficacy of an ingredient does not encompass mere dilution of the ingredient. In the context of the animal, "not deleterious" means that the carrier is not injurious or lethal to the plant or animal.

"Adjuvant", as used herein, refers to any material used in conjunction with an antigen that enhances the ability of that antigen to induce an immune response.

"Administration", as used herein, refers to any means of providing a polynucleotide, a polypeptide or composition thereof to a subject. Non-limiting examples of administration means include subcutaneous injection, intravenous injection, intradermal injection, parenteral injection, intramuscular injection, needle free injection, electroporation, oral delivery, intranasal delivery, oronasal delivery, or any combination thereof.

"Antigen", as used herein, refers to any entity that induces an immune response in a host.

"Consensus sequence", as used herein, refers to an amino acid, DNA or RNA sequence created by aligning two or more homologous sequences and deriving a new sequence that represents the common amino acid, DNA or RNA sequence.

"Hypoglycosylated PRRSV GP5 polypeptide variant", as used herein, refers to PRRSV GP5 proteins wherein the original or non-variant amino acid sequence that comprises one or more N-linked glycosylation sites has been changed so as to reduce the number of N-linked glycosylation sites in the resultant GP5 variant protein. Under this definition, expression of an original or non-variant GP5 protein in E. coli to produce a GP5 protein with the original GP5 sequence containing the same number of glycosylation sites would not result in production of a hypoglycosylated PRRSV GP5 polypeptide variant.

"Immune response", as used herein, refers to the production of antibodies and/or cells (such as T lymphocytes) that bind, degrade or otherwise inhibit, a particular antigen. Related phrases such as "an improved immune response" refer to the use of the methods and compositions that result in any measurable improvement in the response of an immunized host to an antigen. For example, measurable improvements in an immune response include, but are not limited to, increased production of neutralizing antibodies (i.e., increased antibody titers) relative to the levels of production observed in control animals that have been immunized with antigens that lack the structural modifications that provide for an improved immune response.

"Infectious RNA molecule" refers to an RNA molecule that encodes all necessary elements for production of a functional virion when introduced into a permissive host cell.

"Infectious clone", as used herein, refers to a DNA molecule that encodes an infectious RNA molecule.

"North American PRRSV", as used herein, refers to any PRRSV comprising polynucleotide sequences associated with a North American PRRSV isolates, such as, but not limited to, the NVSL 97-7895 strain (Truong et al, Virology, 325:308-319 and references contained therein) or IAF-Klop, MLV, ATCC VR-2332, ATCC VR-2385, IAF-BAJ, IAF-DESR, IAF-CM, IAF 93-653, IAF 93-2616, IAF 94-3182, IAF 94-287 strains described in Pirzadeh et al. Can. J. Vet Res, 62: 170-177 and references contained therein). For this invention, PRRSV comprising polynucleotide sequences associated with a North American PRRSV isolates are PRRSV containing polynucleotide sequences wherein the GP5 encoding region encodes a polypeptide that has at least 85% protein sequence identity to SEQ ID NO:1.

"European PRRSV", as used herein, refers to any PRRSV comprising polynucleotide sequences associated with a North American PRRSV isolates, such as, but not limited to, the Lelystad strain (Wissink et al., J. Gen. Virol. 85:3715, 2004 and references contained therein). For this invention, PRRSV comprising polynucleotide sequences associated with a European PRRSV isolates are PRRSV containing polynucleotide sequences wherein the GP5 encoding region encodes a polypeptide that has at least 85% protein sequence identity to SEQ ID NO:15.

"Percent identity", as used herein, refers to the number of elements (i.e., amino acids or nucleotides) in a sequence that are identical within a defined length of two optimally aligned DNA, RNA or protein segments. To calculate the "percent identity", the number of identical elements is divided by the total number of elements in the defined length of the aligned segments and multiplied by 100. When percentage of identity is used in reference to proteins it is understood that certain amino acid residues may not be identical but are nonetheless conservative amino acid substitutions that reflect substitutions of amino acid residues with similar chemical properties (e.g., acidic or basic, hydrophobic, hydrophilic, hydrogen bond donor or acceptor residues). Such substitutions may not change the functional properties of the molecule. Consequently, the percent identity of protein sequences can be increased to account for conservative substitutions.

Introduction

The porcine reproductive and respiratory syndrome virus (PRRSV) glycoprotein 5 (GP5) is the most abundant envelope glycoprotein and a major inducer of neutralizing antibodies in vivo. Three putative N-linked glycosylation sites (N34, N44, and N51) are located on the GP5 ectodomain, where a major neutralization epitope also exists. To determine which of these putative glycosylation sites are used in PRRSV life cycle and the role of the glycan moieties in induction of neutralizing antibodies, we generated a panel of GP5 mutants containing single and multiple amino acid substitutions at these sites. Transient expression of the wild-type (wt) as well as the mutant proteins and subsequent biochemical studies revealed that the mature GP5 contains high-mannose type sugar moieties at all three sites. These mutations were subsequently incorporated into a full-length cDNA clone to recover infectious PRRSV. Our results demonstrate that mutations involving N44 residue did not result in infectious progeny production, indicating that N44 is the most critical amino acid residue for viral infectivity. Viruses carrying mutations at N34, N51, and N34/51 grew to lower titers than the wt PRRSV and exhibited reduced cytopathic effect in MARC 145 cells. In serum neutralization assays, the mutant viruses exhibited enhanced sensitivity to neutralization by wt PRRSV-specific antibodies. Furthermore, inoculation of pigs with the mutant viruses induced significantly higher levels of neutralizing antibodies against the mutant as well as the wt PRRSV, thus suggesting that the loss of glycan residues in the ectodomain of GP5 enhances both the sensitivity of these viruses to in vitro neutralization as well as the immunogenicity of the nearby neutralization epitope. These results should have great significance for development of PRRSV vaccines of enhanced protective efficacy.

Neutralizing antibodies are known to be a major correlate of protection against PRRSV. We have found that elimination of glycosylation sites in PRRSV GP5 protein results in significant enhancement of: (1) the ability of the modified PRRSV strain to be neutralized by a PRRSV convalescent antiserum and (2) the ability of this modified PRRSV strain to produce unprecedented levels of PRRSV-neutralizing antibodies when used to inoculate pigs. The application of this concept to any live (wt or attenuated) virus used for immunizing against PRRSV infection would have significant impact in its usage to confer effective protection against PRRSV infection.

At the current time, there exists three main approaches to immunize against PRRSV infections: (1) live attenuated vaccines, (2) inactivated vaccines (which are based on wt PRRSV grown in vitro and chemically inactivated), and (3) use of purposeful infection with virulent wt PRRSV in a systematic manner to all animals of the herd. There is a lot of discussion and controversy about which of these 3 ways is the most effective. Our invention would be beneficial, regardless of the approach used for immunization. The genetic alteration of a live PRRSV to modify the glycosylation level of its proteins can be done in either the attenuated PRRSV vaccine strain, or the wt PRRSV strain used to produce an inactivated vaccine, or the wt PRRSV strain used for direct inoculation of the herd by mass infection.

The porcine reproductive and respiratory syndrome virus (PRRSV) belongs to the family Arteriviridae within the order Nidovirales that also includes equine arteritis virus (EAV), lactate dehydrogenase-elevating virus (LDV), and simian hemorrhagic fever virus (SHFV). The viral genome is a linear, positive stranded RNA molecule of approximately 15.0 kb in length and possesses a cap structure at the 5'-end and a poly(A) tail at the 3'-end. Eight open reading frames (ORF)

are encoded in the viral genome. The first two open reading frames (ORF1a and ORF1ab) encode viral non-structural (NS) polyproteins that are involved in polyprotein processing and genome transcription and replication. The viral structural proteins, encoded in ORF2-7, are expressed from six subgenomic capped and polyadenylated mRNAs that are synthesized as 3'-coterminal nested set of mRNAs with a common leader sequence at the 5' end. The major viral envelope protein is the glycoprotein 5 (GP5), which is encoded in the ORF5 of the viral genome. GP5 is a glycosylated transmembrane protein of approximately 25 kDa in size. It has a putative N-terminal signal peptide and possesses three potential N-linked glycosylation sites which are located in a small ectodomain comprising the first 40 residues of the mature protein. In EAV and LDV, the major envelope glycoprotein forms a disulfide-linked heterodimer with the ORF6 gene product, the viral matrix (M) protein. Similar interaction between PRRSV GP5 and M protein has been observed but the mode of interaction has not been defined yet. It has been postulated that formation of heterodimers of GP5 and M proteins may play a critical role in assembly of infectious PRRSV. In addition to its role in virus assembly, GP5 appears to be involved in entry of the virus into susceptible host cells. GP5 is presumed to interact with the host cell receptor, sialoadhesin for entry into porcine alveolar macrophages (PAMs), the in vivo target cells for PRRSV. The role of GP5 in receptor recognition is supported by the presence of a major neutralization epitope in the N-terminal ectodomain, thus implying a central role for the GP5 ectodomain in the infection process.

The N-linked glycans of the GP5 ectodomain may be critical for proper functioning of the protein. The N-linked glycosylation, in general, is important for correct folding, targeting, and biological activity of proteins. In many enveloped viruses, the envelope proteins are modified by addition of sugar moieties and the N-linked glycosylation of envelope protein plays diverse functions of viral glycoproteins such as receptor binding, membrane fusion, penetration into cells, and virus budding. Recent studies have demonstrated the role of N-linked glycosylation of Hantaan virus glycoprotein in protein folding and intracellular trafficking as well as in biological activity and antigenicity of influenza virus hemagglutinin (HA) protein. Furthermore, it has become evident that glycosylation of viral envelope proteins is a major mechanism for viral immune evasion and persistence used by several different enveloped viruses to escape, block or minimize the virus-neutralizing antibody response. Examples of this effect have been reported for SIV and HIV-1, HBV, influenza and more importantly, in the case of PRRSV, the arterivirus LDV.

Recently the development of reverse genetic systems for PRRSV has been reported from several laboratories including ours. Evidently, mutational studies with infectious clones have led to a better understanding of the mechanisms of transcription and replication of the viral genome of arteriviruses. Thus, in order to examine the importance of N-linked glycosylation in the biological activity of GP5 of PRRSV in generating infectious virus or eliciting neutralizing antibodies in vivo, we have constructed a series of mutant GP5 proteins in which each of the potential N-linked glycosylation sites has been mutated either individually or in various combinations. The resulting mutant proteins were examined for their glycosylation pattern, role in infectious virus recovery and in cross neutralization by antibodies raised, through experimental inoculations, against the wt PRRSV or against the mutant viruses. Our data show that all three putative glycosylation sites are used for glycosylation with high-mannose type glycans and glycosylation of GP5 protein at residue 44 is critical for recovery of infectious PRRSV. Very importantly, our data from neutralization and antibody response studies indicate that natural infection with PRRSV may involve an immune evasion based on glycan shielding mechanisms as was previously described for other viruses, thus helping to explain the rather ineffective protective humoral immune response that is observed in PRRSV-infected animals.

N-Linked Glycosylation Sites and Methods of Inactivation

N-linked glycosylation in glycoproteins typically occurs at Asn-Xaa-Ser/Thr (NXS/T) sequences, where Xaa (X) is any amino acid residue except Pro. A variety of mutations can be introduced at N-linked glycosylation sites to provide for their inactivation. A preferred method of inactivation comprises substitution of the asparagine residue with a residue encoding any amino acid other than asparagine. In more preferred embodiments of this invention, the asparagine residue is substituted with an alanine or a glutamine residue.

Other methods of inactivating N-linked glycosylation sites, and in particular the N-linked glycosylation sites corresponding to asparagines 34 and/or 51 of the GP5 reference protein of SEQ ID NO:1, are also contemplated herein. Substitutions of certain amino acids such as proline, tryptophan, aspartate, glutamate or Leucine at the Xaa position can also be used to inactivate N-linked glycosylation sites (Kasturi et al., Biochem J. 323 (2):415-9, 1997). Alternatively, substitutions of the final hydroxy amino acid position of the N-linked glycosylation site (i.e., the serine or threonine residue of the NXS/T sequence) with any non-hydroxy amino acid (i.e., any amino acid other than serine or threonine) can also be used to inactivate the N-linked glycosylation site. Examples of non-hydroxy amino acids that have been used to inactivate N-linked glycosylation sites include cysteine (Kasturi et al., J. Biol. Chemistry 270(24), 14756-14761, 1995).

In addition to amino acid substitutions, other types of mutations that inactivate N-linked glycosylation sites such as amino acid insertions or amino acid deletions are also contemplated by this invention. Those skilled in the art will appreciate that an N-linked glycosylation site can be readily inactivated by deletions that remove key amino acids in the NXS/T sequence (i.e., the asparagine residues) will result in the inactivation of that glycosylation site. Deletions of the X residue or serine/threonine residue can similarly inactivate certain N-linked glycosylation sites where the S or T residue is not followed by another S or T residue in the naturally occurring sequence. When X is a non-hydroxy amino acid (i.e., is not serine or threonine), insertions of any amino acid residue at the carboxy terminal end of the N residue can inactivate the N-linked glycosylation site. Insertions of any non-hydroxy amino acids at the carboxy terminal end of the X residue can also inactivate the N-linked glycosylation site.

In summary, it is understood that the key feature of the mutation used to practice the invention is that it inactivates N-linked glycosylation at the asparagine 34 and/or asparagine 51 sites in a GP5 protein. While not being limited by theory, it is believed that the key feature of these mutations are that they prevent glycosylation in a certain region of the protein (i.e., residues corresponding to the asparagine 34 and/or asparagine 51 sites in a GP5 reference protein of SEQ ID NO:1). By preventing glycosylation at these sites, sugar residues that ordinarily shield key epitopes of the wild type virus are removed, thus permitting elicitation of an improved immune response. Consequently, it is anticipated that a number of different types of mutations (i.e., amino acid substitution, insertion or deletion) can be used to inactivate the identified N-linked glycosylation sites and obtain an antigen that will elicit the improved immune response.

Description of PRRSV Polynucleotides and Polypeptides of the Invention

The methods of this invention can be practiced with a variety of different polynucleotides that can be derived from a variety of different sources. The common feature of all of the polynucleotides is that they encode a hypoglycosylated PRRSV GP5 polypeptide variant where N-linked glycosylation sites corresponding to either asparagine 34, asparagine 51, or both asparagine 34 and asparagine 54 in a reference GP5 protein of SEQ ID NO:1 are inactivated. To identify the N-linked glycosylation sites corresponding to asparagine 34 and asparagine 54 in the reference GP5 protein of SEQ ID NO:1, the non-variant and normally glycosylated PRRSV GP5 polypeptide sequence can be aligned with the reference GP5 protein of SEQ ID NO:1. Examples of such an alignment are displayed in FIGS. 5 and 6. The particular sequences used in this alignment are described in Table 1.

TABLE 1

Description of Sequences

| Description | GenBank Accession (Reference) | Sequence ID NO: |
|---|---|---|
| GP5 Protein North American PRRSV strain NVSL 97-7895 | AAS59265.1 (Truong, H. M., et al. Virology 325 (2), 308-319, 2004) | SEQ ID NO: 1 |
| GP5 Protein North American PRRSV strain 1. IAF-Klop | AAC41206.1 | SEQ ID NO: 2 |
| GP5 Protein North American PRRSV strain IAF-BAJ | AAC41209.1 | SEQ ID NO: 3 |
| GP5 Protein North American PRRSV strain IAF-DESR | AAC41212.1 | SEQ ID NO: 4 |
| GP5 Protein North American PRRSV strain IAF 93-653 | AAC41215.1 | SEQ ID NO: 5: |
| GP5 Protein North American PRRSV strain IAF 93-2616 | AAC41218.1 | SEQ ID NO: 6 |
| GP5 Protein North American PRRSV strain 94-3182 | AAC41221.1 | SEQ ID NO: 7 |
| GP5 Protein North American PRRSV strain 94-287 | AAC41224.1 | SEQ ID NO: 8 |
| GP5 Protein North American PRRSV strain IAF-CM | AAC28399.1 (with Ser 106 as per Pirzadeh, B., et al. Can. J. Vet. Res. 62 (3), 170-177 (1998) | SEQ ID NO: 9: |
| GP5 Protein North American PRRSV strain ONT-TS | AAC41227.1 | SEQ ID NO: 10 |
| GP5 Protein North American PRRSV strain VR-2332 | AAD12129.1 | SEQ ID NO: 11 |
| GP5 Protein North American PRRSV strain VR-2385 | AAA67155.1 | SEQ ID NO: 12: |
| GP5 Protein North American PRRSV strain MLV | AAD27656.1 | SEQ ID NO: 13 |
| GP5 Protein North American PRRSV strain Consensus | Pirzadeh, B., et al. Can. J. Vet. Res. 62 (3), 170-177 (1998) | SEQ ID NO: 14 |

TABLE 1-continued

Description of Sequences

| Description | GenBank Accession (Reference) | Sequence ID NO: |
|---|---|---|
| GP5 Protein European PRRSV strain LV | AAA47105.1 | SEQ ID NO: 15 |
| PRRSV Infectious clone DNA North American PRRSV strain NVSL 97-7895 | AAS59265. (Truong, H. M., et al. Virology 325 (2), 308-319, 2004) | SEQ ID NO: 16 |
| PRRSV Infectious clone DNA North American PRRSV strain VR-2332 | AY150564. (Nielsen, H. S., et al., J. Virol. 77 (6), 3702-3711, 2003) | SEQ ID NO: 17 |

To identify N-linked glycosylation sites corresponding to asparagine 34 or asparagine 51 in a reference GP5 protein of SEQ ID NO: 1 that can be inactivated and used in the methods of this invention, the GP5 proteins of either a desired North American PRRSV isolate (FIG. 5) or a European PRRSV isolate (FIG. 6) are aligned with reference GP5 protein of SEQ ID NO:1 (North American strain NVSL 97-7895). By using the GP5 protein of SEQ ID NO:1 as a reference protein, one skilled in the art can readily identify the N-linked glycosylation sites in any GP5 protein and then construct the hypoglygosylated GP5 protein variants of this invention. It is thus apparent that the term "corresponding to (asparagine 34 and/or asparagine 51) in a reference GP5 protein of SEQ ID NO:1" serves as a descriptor of the N-linked glycosylation site in any GP5 protein.

The hypoglycosylated GP5 protein can be obtained from a North American PRRSV isolate including, but not limited to, SEQ ID NO:1-13, a North American PRRSV isolate that is at least 85% identical at an amino sequence level to a North American PRRSV consensus sequence such as SEQ ID NO:14, or from a North American PRRSV consensus sequence. The hypoglycosylated GP5 protein can also be obtained from European PRRSV isolates including, but not limited to, SEQ ID NO:15, a European PRRSV isolate that is at least 85% identical at an amino sequence level to a European PRRSV consensus sequence such as SEQ ID NO:15, or from a European PRRSV consensus sequence. To obtain the hypoglycosylated GP5 variant encoding polynucleotides, polynucleotides from any of the sources listed above can be mutagenized by standard site-directed mutagenesis techniques such that they will encode a hypoglycosylated GP5 variant polypeptide. Alternatively, an entirely synthetic DNA sequence can be constructed that encodes the desired hypoglycosylated GP5 variant polypeptide. This is typically accomplished by using a sequence analysis program such as "back translate" which converts a polypeptide sequence into a corresponding polynucleotide sequence (GCG Wisconsin Package™, Accelrys, Inc, San Diego, Calif.). If desired, a suitable "codon bias" can be incorporated into the "back translate" program to provide for the design of a synthetic gene that incorporates codons appropriate for use in the desired expression host (i.e., mammalian or yeast).

The N-linked glycosylation site corresponding to asparagine 51 of the reference GP5 protein of SEQ ID NO:1 is present in all of the representative North American PRRSV isolates shown in FIG. 5 and in the representative European PRRSV Lelystad strain (FIG. 6). In these exemplary and non-limiting North American and European PRRSV strains, the N-linked glycosylation site at this position comprises the sequence "NGT". However, it is also anticipated that other PRRSV variants may comprise other structurally interchangeable N-linked glycosylation sites at this position (i.e., NXS or T) that could also be inactivated via the methods taught herein. This N-linked glycosylation site can be inactivated by substituting codons encoding other amino acid residues such as glutamine or alanine for asparagine 51 in the corresponding polynucleotide sequence. In these instances, the corresponding amino acid sequence in the hypoglycosylated North American PRRSV GP5 protein variant would comprise the sequences such as "QGT", "AGT", or "XGT", where X is any amino acid other than asparagine. These or other hypoglycosylated variants of the North American PRRSV GP5 protein isolates where the N-linked glycosylation site corresponding to asparagine 51 is inactivated can also be combined with other hypoglycosylated GP5 variants where other N-linked glycosylation sites are inactivated. Other methods of inactivating N-linked glycosylation sites include amino acid substitutions of the "X" or "S/T" residues of the NXS/T sequence, amino acid deletions or amino acid insertions and are described above.

The N-linked glycosylation site corresponding exactly to asparagine 34 of the reference GP5 protein of SEQ ID NO:1 is present in only certain representative North American PRRSV isolates shown here (FIG. 5). More specifically, the GP5 proteins of North representative American PRRSV isolates IAF-BAJ (SEQ ID NO:3), 94-3182 (SEQ ID NO:7), and 94-287 (SEQ ID NO:8) contain the N-linked glycosylation site corresponding exactly to asparagine 34 of the reference GP5 protein of SEQ ID NO:1 and comprises the N-linked glycosylation site "NSS". It is of course anticipated that other PRRSV GP5 isolates not shown here will also contain N-linked glycosylation sites corresponding to asparagine 34 of the reference GP5 protein of SEQ ID NO:1 and that hypoglycosylated variants of these other GP5 proteins can also be obtained using the methods described herein. This N-linked glycosylation site of SEQ ID NO:3, 7, and 8 or other PRRSV isolates containing the asparagine 34 N-linked glycosylation site can be inactivated by substituting codons encoding other amino acid residues such as glutamine or alanine for asparagine 34 in the corresponding polynucleotide sequence. In these instances where the N-linked glycosylation site at asparagine 34 is "NSS", the corresponding amino acid sequence in the hypoglycosylated North American PRRSV GP5 protein variant would comprise the sequences such as "QSS", "ASS", or "XSS", where X is any amino acid other than asparagine. Alternatively, the serine residue of the "NSS" sequence can be substituted with a non-hydroxy amino acid (i.e., non-serine of non-threonine). In these instances, the corresponding amino acid sequence in the hypoglycosylated North American PRRSV GP5 protein variant would comprise the sequence "NSX", where X is any amino acid other than asparagine. An insertion of a non-hydroxy amino acid between the two serine residues of the "NSS" sequence (i.e., between serines 35 and 36) can also be used to inactivate this particular glycosylation site.

In other North American PRRSV isolates that lack the N-linked glycosylation site corresponding exactly to asparagine 34 of the reference GP5 protein of SEQ ID NO:1, other N-linked glycosylation sites located at residue 30 (FIG. 5 "NAS" in SEQ ID NO:2, 3, 4, 6, 7, 8, 9, 11, 13), and residue 33 (FIG. 5 "NNS" in SEQ ID NO:3, 8; "NSS" in SEQ ID NO:6, 10, "NDS" in SEQ ID NO:11, 13) can also be inactivated. In other words, N-linked glycosylation sites in other North American isolates located at amino acid positions corresponding to residues 30 and 33 of the reference GP5 protein of SEQ ID NO:1 can also be inactivated and used in the methods of this invention. Without being limited by theory, the particular region of the PRRSV GP5 protein located between residues 29 and 35 of the GP5 reference protein of SEQ ID NO:1 appears to be a hypervariable region (FIG. 5) that can tolerate a variety of distinct amino sequences (FIG. 5; also see Pirzadeh et al., Can. J. Vet Res., 1998, 62: 170-177). Although certain naturally occurring PRRSV isolates contain no N-linked glycosylation sites in this region (i.e., North American isolates of SEQ ID NO:5, 12; European isolate of SEQ ID NO:15), other isolates can contain between 1 to 3 glycosylation sites in this region. Consequently, inactivation of any one of the glycosylation sites of a given GP5 protein in the region located between residues 29 and 35 of the GP5 reference protein of SEQ ID NO:1 is contemplated herein as a composition or method for eliciting an improved immune response to the PRRSV GP5 protein. Furthermore, inactivation of more than one or all of the glycosylation sites a given GP5 protein in the region located between residues 29 and 35 of the GP5 reference protein of SEQ ID NO:1 is also contemplated herein as a composition or method for eliciting an improved immune response to the PRRSV GP5 protein.

Alignment of the North American and the European PRRSV sequence shows that the N-linked glycosylation site corresponding to asparagine 51 of the reference GP5 protein of SEQ ID NO:1 is also present in a representative European PRRSV isolate. In this particular instance, the N-linked glycosylation site comprises the sequence "NGT" and the asparagine 51 of the SEQ ID NO:1 reference sequence corresponds to asparagine 53 of SEQ ID NO:15. This N-linked glycosylation site can be inactivated by substituting codons encoding other amino acid residues such as glutamine or alanine for asparagine 53 in the corresponding European PRSSV polynucleotide sequence. In these instances, the corresponding amino acid sequence in the hypoglycosylated European PRRSV GP5 protein variant would comprise the sequences such as "QGT", "AGT", or "XGT", where X is any amino acid other than asparagine. These or other hypoglycosylated variants of the European PRRSV isolates where N-linked glycosylation site corresponding to asparagine 51 is inactivated can also be combined with other hypoglycosylated GP5 variants where other N-linked glycosylation sites are inactivated.

The hypoglycosylated GP5 variant proteins can be encoded by PRRS viruses that can be used to prepare live, killed, or attenuated vaccines for protecting pigs from PRRSV infections. In preferred embodiments of the invention, the hypoglycosylated GP5 variant proteins of this invention are engineered into infectious PRRSV clones that are capable of producing infectious PRRSV RNA. Descriptions of infectious North American PRRSV clones that could be engineered to encode hypoglycosylated GP5 variant proteins are found in U.S. Pat. No. 6,500,662, Nielsen et al., J. Virol. 77:3702-11, 2003, and Truong et al., Virology 325:308-19, 2004. North American PRRSV infectious clone sequences that can be mutagenized to obtain PRRSV viruses for use in vaccines include but are not limited to the North American strains NVSL 97-7895 (SEQ ID NO:16) and strain VR-2332 (SEQ ID NO:17). Descriptions of infectious European PRRSV clones that could be engineered to encode hypoglycosylated GP5 variant proteins are found in U.S. Pat. No. 6,268,199. In embodiments where the vaccine comprises a live or attenuated PRRSV, the N-linked glycosylation site corresponding to N44 in the reference GP5 protein of SEQ ID NO:1 (i.e., the "NLT" sequence in FIGS. 5 and 6) is not inactivated as glycosylation of this site is required for infectivity of the PRRSV. In the case of the European PRRSV isolates, the N-linked glycosylation site corresponding to N44 in the reference GP5 protein of SEQ ID NO:1 is the NLT sequence that begins at asparagine 46 of the representative European PRRSV strain Lelystad (SEQ ID NO:15; FIG. 6). The N46 N-linked glycosylation site of the European PRRSV strains is also required for infectivity and is not inactivated in embodiments of the invention where a live or attenuated PRRSV vaccine is used.

Alternatively, the hypoglycosylated GP5 variant proteins can be introduced into pigs with DNA vaccines. Such DNA vaccines typically comprise a DNA molecule wherein a promoter active in mammalian cells is operably linked to said polynucleotide encoding said hypoglycosylated PRRSV GP5 polypeptide variant. Promoters that can be used to drive expression of the hypoglycosylated GP5 variant proteins include, but are not limited to, the CMV (cytomegalovirus) immediate early promoter, RSV (Rous sarcoma virus) long terminal repeat promoter, and SV40 (Simian Virus 40) T-antigen promoter. In certain preferred embodiments, this promoter is a CMV promoter.

In still other embodiments, the isolated polynucleotide expressing the hypoglycosylated GP5 variant protein comprises a viral vector other than PRRSV. Viral vectors other than PRRSV include, but are not limited to, vaccinia virus vectors, a herpes simplex viral vectors, adenovirus vectors, alphavirus vectors, and TGEV vectors. Such vectors are described in various publications such as U.S. Pat. No. 7,041,300 (for TGEV vectors) and U.S. Pat. No. 6,692,750 (for alphavirus vectors).

Therapeutically Acceptable Carriers and Adjuvants

In practicing the invention, the hypoglycosylated GP5 variant polypeptides or polynucleotides that encode hypoglycosylated GP5 variant polypeptides can be combined with therapeutically acceptable carriers or excipients. Non limiting examples of such carriers include physiological saline or other similar saline solutions, proteins such as serum albumin proteins, buffers such as carbonate, phosphate, phosphonate, or Tris based buffers, surfactants such as NP40 or Triton X100, and a polyethylene glycol polymers. Any combination of such carriers can be used in the compositions and methods of this invention. A preferred carrier for compositions comprising live or attenuated PRRSV viruses is dl-α-tocopherol acetate at a concentration of between 50 to 100 mg/ml.

The use of adjuvants in compositions containing either the hypoglycosylated GP5 variant polypeptides or polynucleotides that encode hypoglycosylated GP5 variant polypeptides is also contemplated. Such adjuvants are typically either aqueous or oily in nature. Adjuvants that can be used include, but are not limited to, aluminum hydroxide, Quil A, an alumina gel suspension, mineral oils, glycerides, fatty acids, fatty acid by-products, mycobacteria, and CpG oligodeoxynucleotides, or any combination thereof. Various types of CpG adjuvants that can be used are described U.S. Pat. Nos. 6,977,245 and 6,406,705.

The use of other adjuvants that potentiate cellular immune responses (i.e., T helper cell (Th.sub.1 and Th.sub.2) subpopulation potentiators) is also contemplated. Such adjuvants include but are not limited to interleukin 1 (IL-1), IL-2, IL4, IL-5, IL6, IL-12, gamma interferon (g-IFN), cell necrosis factor, MDP (muramyl dipeptide), immuno stimulant complex (ISCOM), and liposomes.

Administration of the composition can be accomplished by subcutaneous injection, intravenous injection, intradermal injection, parenteral injection, intramuscular injection, needle free injection, electroporation, oral delivery, intranasal delivery, oronasal delivery, or any combination thereof. Needle free injection is typically effected with a device such as an Agro-Jet® injector (Medical International Technologies, Montreal, Canada).

EXAMPLES

Example 1

The following example illustrates the construction of various PRRSV polynucleotides that encode various hypoglycosylated North American PRRSV GP5 polypeptide variants, compositions including such polynucleotides that are used to elicit improved immune responses to a PRRSV antigen, and methods of using the polynucleotides and compositions to elicit an improved immune response in a pig to a PRRSV antigen.

Materials and Methods

Cells, media, and antibodies. The MARC-145 cells were propagated in Dulbecco's Modified Eagle's Medium (DMEM) containing 10% fetal bovine serum (FBS) and 100 units of penicillin, 20 units of streptomycin and 20 units of kanamycin per ml of growth medium. These cells were used for RNA electroporation, virus infection, viral growth, and plaque assays. The baby hamster kidney (BHK-21) cells were maintained in Minimal Essential Medium (MEM) with Earl's salt containing 5% FBS and the above mentioned antibiotics. BHK-21 cells were used for transient expression of GP5 followed by either immunofluorescence assays (IFA) or radiolabeling and immunoprecipitation experiments. All cells were maintained at 37° C. and 5% $CO_2$ environment. Rabbit polyclonal antibodies to PRRSV GP5 and M proteins were kindly provided by Carl A. Gagnon (University of Quebec, Montreal, Canada). The monoclonal antibody (SDOW17) against nucleocapsid protein (N) was purchased from National Veterinary Services Laboratories (NVSL, Ames, Iowa, USA). Anti-mouse Alexa-488 was obtained from Molecular Probes, Inc. (Eugene, Oreg., USA).

Genetic Manipulation of Plasmids Encoding GP5 and PRRSV Infectious Clone

The full-length PRRSV infectious cDNA clone (FL12; SEQ ID NO:16) in pBR322 was digested with EcoRV and BstZ17 I restriction enzyme and the ~4.9 kbp fragment encompassing majority of ORF2, complete ORF3-7, and the entire 3'UTR of PRRSV was cloned in pBR322 using the same enzyme sites. This intermediate plasmid served as the template for mutagenesis to introduce mutations at the potential N-linked glycosylation sites (N34, N44, and N51) within GP5 (FIG. 2). Mutagenesis was carried out using overlap extension PCR with synthetic primers (Table 2) using standard techniques.

TABLE 2

Primers and their sequences used in this study.

| Primers | Nucleotide sequences |
|---|---|
| GP5-N34A-For | 5' GCCAACAGC<u>GCC</u>AGCAGCTCTC 3'<br>(SEQ ID NO:18) |
| GP5-N44A-For | 5' GTTGATTTAC<u>GCC</u>TTGACGCTATG 3'<br>(SEQ ID NO:19) |
| GP5-N51A-For | 5' GTGAGCTG<u>GCT</u>GGCACAGATTG 3'<br>(SEQ ID NO:20) |

TABLE 2-continued

Primers and their sequences used in this study.

| Primers | Nucleotide sequences |
|---|---|
| GP5-N34/44A-For | 5' GCCAACAGC<u>GCC</u>AGCAGCTCTCATCTTCA GTTGATTTAC<u>GCC</u>TTGACGCTATG 3' (SEQ ID NO:21) |
| GP5-N44/51A-For | 5' GTTGATTTAC<u>GCC</u>TTGACGCTATGTGAGC TG<u>GCT</u>GGCACAGATTG 3' (SEQ ID NO:22) |
| GP5-N34/51A-For | 5' GCCAACAGC<u>GCC</u>AGCAGCTCTCATCTTCA GTTGATTTAC<u>AAC</u>TTGACGCTATGTGAGCTG<u>G CT</u>GGCACAGATTG 3' (SEQ ID NO:23) |
| GP5-N34/44/51A-For | 5' GCCAACAGC<u>GCC</u>AGCAGCTCTCATCTTCA GTTGATTTAC<u>GCC</u>TTGACGCTATGTGAGCTG<u>G CT</u>GGCACAGATTG 3' (SEQ ID NO:24) |
| PRRSV-13177-For | 5' CTACCAACATCAGGTCGATGGCGG 3' (SEQ ID NO:25) |
| PRRSV-14473-Rev | 5' GTCGGCCGCGACTTACCTTTAGAG 3' (SEQ ID NO:26) |

Underlined codon sequences indicate the site of mutation.

The PCR product was digested with BsrG I and BstE II restriction enzymes and replaced back in the intermediate plasmid. Clones containing the desired mutations were identified and confirmed by sequencing. The entire coding region of GP5 was sequenced to make sure that additional mutations were not present in the clones. The EcoRV-Pac I fragment from the intermediate plasmid containing mutations in the GP5 coding region was moved back into the full-length cDNA clone using the same restriction enzyme sites. The GP5 coding region in the full length clones was again sequenced with PRRSV specific internal primers to confirm the presence of the mutations.

The wt GP5 and individual mutants were cloned in a bicistronic vector where the GP5 is the first cistron followed by encephalomyocarditis virus (EMCV) internal ribosome entry site (IRES) and M coding sequences (FIG. 1A). The full length GP5 was also cloned in a CMV promoter driven vector (pcDNA 3.0™, Clontech Laboratories, Inc., Mountain View, Calif., USA) for complementation studies. To this end, the GP5 coding region was PCR amplified, cloned and sequenced.

In Vitro Transcription and Electroporation

The full-length plasmids were digested with AclI and linearized DNA was used as the template to generate capped RNA transcripts using the mMESSAGE mMACHINE Ultra T7™ kit as per manufacturer's (Ambion, Inc., Austin, Tex., USA) recommendations and as described earlier. The reaction mixture was treated with DNaseI to digest the DNA template and extracted with phenol and chloroform and finally precipitated with isopropanol. The integrity of the in vitro transcripts was analyzed by glyoxal agarose gel electrophoresis followed by ethidium bromide staining.

MARC-145 cells were electroporated with approximately 5.0 μg of in vitro transcripts along with 5.0 μg of total RNA isolated from MARC-145 cells. About 2×106 cells in 400 μl of DMEM containing 1.25% DMSO were pulsed once using Bio-Rad Gene Pulser Xcell™ (Bio-Rad, Inc., Hercules, Calif., USA) at 250V, 950 μF in a 4.0 mm cuvette. The cells were diluted in normal growth media, plated in a 60-mm cell culture plate. A small portion of the electroporated cells was plated in a 24-well plate to examine expression of N protein at 48 hrs post-electroporation, which would indicate genome replication and transcription. Once expression of N protein is confirmed using indirect immunofluorescence assay (IFA), the supernatant from bulk of the electroporated cells in 60-mm plate was collected at 48 hrs post-electroporation, clarified and passed onto naïve MARC-145 cells. The infected cells were observed for cytopathic effect (CPE) along with the expression of N protein using IFA. The supernatants from infected cells showing both CPE and positive fluorescence were assigned to contain infectious virus. After confirmation, the virus stock was grown and frozen at −80° C. in small aliquots for further studies. In all the experiments, FL12 containing wt PRRSV genome and FL12pol-containing polymerase-defective PRRSV genome were used as controls.

Metabolic Radiolabeling and Analyses of Proteins

BHK-21 cells in six-well plates were infected with recombinant vaccinia virus (vTF7-3) at an MOI of 3.0 and subsequently transfected with bicistronic plasmid DNA encoding wt or various mutant GP5 under T7 RNA polymerase promoter. DNA transfection was carried out using Lipofectamine2000™ as per manufacturer's protocol (Life Technologies, USA). At 16 hrs post-transfection, cells were washed twice with PBS and starved in methionine/cysteine-free DMEM for one hr and radiolabeled with 0.6 ml of methionine/cysteine-free DMEM containing 100 μCi of Expre$^{35}$S$^{35}$S Protein Labeling Mix (NEN Life Sciences, Boston, Mass.) per ml of medium for three hrs. Following radiolabeling, the cells were washed in cold PBS three times and cell extracts were prepared in 300 μl of radioimmunoprecipitation assay (RIPA) buffer (10 mM Tris-HCl pH 8.0, 150 mM NaCl, 1% Triton X-100, 0.1% SDS, 1% Sodium deoxycholate, and 1× protease inhibitor). The clarified cell extracts were incubated overnight at 40 C with rabbit anti-GP5 or anti-M protein antibody. A slurry of approximately 4.0 mg of protein A sepharose (Pharmacia, Uppsala, Sweden) in 100 μl RIPA buffer was added and further incubated for 2 hrs. The immunoprecipitated complexes were washed 3 times with 500 μl of RIPA buffer and used for further analysis.

For endoglycosidase H (Endo H) treatment, the immunoprecipitated complexes were resuspended in 20 μl of 1× denaturing buffer (0.5% SDS, 1.0% β-mercaptoethanol) and boiled for 10 min. The supernatant was collected, adjusted to 1× G5 buffer (0.05 M sodium citrate pH 5.5) and incubated for 16 hrs at 37° C. with 100 units of Endo H (New England Biolabs, Beverly, Mass., USA). The undigested control samples were processed similarly but no Endo H was added. Following Endo H digestion, the samples were mixed with equal volume of 2×SDS-PAGE sample buffer, boiled for 5 min and resolved by SDS-12% PAGE under denaturing conditions along with protein marker (Protein Plus Precision Standard, Bio-Rad, Inc). The gel was fixed with 10% acetic acid for 15 min, washed three times with water, treated with 0.5 M sodium salicylate for 30 min, dried and finally exposed to X-ray film at −70° C. For peptide N-Glycosidase F (PNGase F) (New England Biolabs, Inc) digestion, immunoprecipitated complexes were resuspended in 1× G7 buffer (0.05 M sodium phosphate pH 7.5, 1.0% NP-40) and digestion was performed by incubating for 16 hrs at 37° C. with 2 units of the enzyme. To examine synthesis of GP5 in the presence of tunicamycin (Sigma, St. Louis, Mo.), transfected cells were treated with 2.0 μg of tunicamycin per ml of medium for one hr and radiolabeling was performed in the presence of the drug for 3 hrs as above.

For obtaining radiolabeled extracellular virions or intracellular virus expressed GP5, MARC-145 cells were infected with wt or mutant PRRSVs. At 48 hrs post-infection, the cells were starved for one hr and radiolabeled with 100 μCi of Expre$^{35}$S$^{35}$S Protein Labeling Mix per ml of medium containing 90% methionine/cysteine free DMEM and 10% regular DMEM for 24 hrs. Following labeling, the culture supernatant was harvested, cleared of cell debris and the extracellular virions were pelleted at 100,000×g for 3 hrs at 4° C. The viral pellets were resuspended in 200 μl of RIPA buffer, immunoprecipitated with anti-GP5 antibody and the proteins were examined with or without Endo H treatment. For immunoprecipitation of intracellular virus expressed GP5, infection was carried as above and at 24 hrs post-infection, the cells were starved for one hr, radiolabeled as above for 2 hrs prior to preparing cell extracts.

Viral Growth Kinetics and Plaque Assay

MARC-145 cells were infected with mutant or wt PRRSV at an MOI of 3.0 PFU per cell and incubated at 370 C in an incubator. At various time points post-infection, aliquots of culture supernatants from infected cells were collected and virus titer in the supernatants was determined and expressed by tissue culture infectious dose 50 per ml (TCID50/ml). The viral growth kinetics was performed three times. To examine the plaque morphology of mutant viruses, plaque assay was performed using MARC-145 cells. Cells were infected with 10-fold serial dilutions of individual viruses for one hr at 37° C. The infected cell monolayer was washed with PBS and overlaid with DMEM-5% FBS containing 0.8% Seaplaque agarose (FMC Bioproducts, Rockland, Me. USA). After 96 hrs, the agarose plugs were removed and cell monolayer was incubated with staining solution (20% Formaldehyde 9.0% Ethanol, and 0.1% Crystal violet) for 30 min at room temperature. The cells were gently washed with water to remove excess dye and air dried to examine and count the plaques.

Complementation of Virus Recovery by Expressing Wt GP5 in Trans

BHK-21 cells were transfected with pcDNA-GP5. At 40 hrs post-transfection, the cells were harvested and electroporated with capped in vitro transcripts derived from full-length PRRSV cDNA encoding mutant GP5. The electroporated cells were diluted with fresh media and plated in 6-well plate. The supernatant from electroporated cells was collected at 48 hrs post-electroporation, centrifuged to remove cell debris and used to infect naïve MARC-145 cells. The infected MARC-145 cells were examined at 48 hrs post-infection for expression of N protein by IFA as described above. The number of positive cells was counted to assign the number of pseudo-particles produced in the supernatant. The average number of positive cells was calculated from three independent experiments and was presented as the number of pseudo-particles produced per microgram of in vitro transcribed RNA transfected into the cells.

Serum-Neutralization (SN) Assays

The titer of PRRSV-neutralizing antibodies in a serum sample was determined using the fluorescence focus neutralization assay described previously. Serial dilutions of test sera were incubated for 60 min at 37° C. in the presence of 200 TCID50 of the challenge virus, which consisted of either FL12 (wt PRRSV) or any of the GP5 mutant encoding viruses, FL-N34A, FL-N51A, and FL-N34/51A in Dulbecco's modified Eagle's medium containing 5% fetal calf serum. The mixtures were added to 96-well microtitration plates containing confluent MARC-145 cells which had been seeded 48 hrs earlier. After incubation for 24 hrs at 37° C. in a humidified atmosphere containing 5% CO2, the cells were fixed for 10 min with a solution of 50% methanol and 50% acetone. After extensive washing with PBS, the expression of N protein of PRRSV was detected with monoclonal antibody SDOW17 using a 1:500 dilution, followed by incubation with FITC-conjugated goat anti-mouse IgG (Sigma, St. Louis, Mo., USA) at a 1:100 dilution. Neutralization titers were expressed as the reciprocal of the highest dilution that inhibited 90% of the foci present in the control wells.

Experimental Inoculation of Pigs with GP5 Mutants and Wt PRRSV

High titer stocks (obtained through 3 passages in MARC 145 cells) of the GP5 mutant viruses (FL-N34A, FL-N51A, and FL-N34/51A) and the FL12 (wt PRRSV) were used to infect young pigs. Twenty-one-day old, recently weaned pigs were purchased from a specific-pathogen-free herd with a certified record of absence of PRRSV infection. All animals were negative for anti-PRRSV antibodies as tested by ELISA (Iddex Labs, Portland, Me.). Three pigs per group were infected with either FL12 wt PRRSV or mutants FL-N34A, FL-N51A, and FL-N34/51A. In all cases, the inoculum consisted of 105 TICD50 diluted in 2 ml and administered intramuscularly in the neck. The rectal temperatures of the inoculated animals were monitored for 15 days post-inoculation (PI). Viremia was measured by regular isolation on MARC 145 cells at days 4, 7 and 14 PI. Serum samples were drawn weekly for a total period of 49 days PI. The serum samples were used to detect homologous and heterologous cross-neutralization titers for each of the mutants and wt PRRSV.

Results

Expression and Characterization of PRRSV GP5

The GP5 of PRRSV strain 97-7895 has three putative glycosylation sites (N34, N44, and N51). To examine the glycosylation pattern of GP5, we first generated a bicistronic vector in which the coding regions of GP5 and M proteins flanking the IRES from EMCV were placed under the control of T7 RNA polymerase promoter (FIG. 1A). The rationale for constructing the bicistronic vector is that the GP5 and M proteins are known (for LDV and EAV) or postulated (for PRRSV) to interact with each other and that such interactions may be important for protein folding, glycosylation, intracellular transport, and/or other biological activity of GP5.

Transient expression of GP5 and M by transfection of the bicistronic plasmid followed by radiolabeling and immunoprecipitation with anti-GP5 antibody revealed two major protein species. The protein species migrating with a mass of ~25.5 kDa is the fully glycosylated form of GP5 (FIG. 1B, lane 2). Since each N-linked glycosylation adds ~2.5 kDa of molecular mass to a protein, this indicates that all three potential glycosylation sites are possibly used for glycosylation of GP5. The 19.0 kDa protein species is the viral M protein since it was also was immunoprecipitated with anti-M antibody (lane 7). The results indicate that GP5 and M proteins interact with each other in cells expressing both proteins. Upon treatment with Endo H, an enzyme that removes high-mannose type oligosaccharide chains, the size of the GP5 was reduced to ~18 kDa, whereas the size of the M protein remained unchanged (lane 3). Treatment of GP5 with PNGase F (lane 4), an enzyme that removes all type sugars from protein backbone or synthesis of GP5 in the presence of tunicamycin (lane 5) resulted in a protein that migrated with slightly faster electrophoretic mobility than the protein with Endo-H treatment. This is expected, since tunicamycin treatment or digestion with PNGase F would generate unglycosylated proteins whereas Endo-H treatment would result in proteins that retain N-acetylglucosamine residues at each of the N-linked glycosylation sites. It is of note that a prominent protein species of ~30 kDa molecular mass was immunoprecipitated with anti-M antibody. The identity of this protein is not known but it could be a cellular protein that interacts with the M protein.

The results from the above studies suggest that the unglycosylated and fully glycosylated forms of GP5 possess apparent molecular sizes of 18.0 kDa and 25.5 kDa, respectively. It appears that all three potential glycosylation sites are used to generate the fully glycosylated form of GP5. The glycan moieties added to these sites are of high-mannose type since they are sensitive to digestion by Endo H. In addition, the results indicate that both unglycosylated and fully glycosylated forms of GP5 appear to interact with the M protein.

Analysis of N-Linked Glycosylation Sites Used for Glycosylation of GP5

To more precisely determine whether all or some of the potential N-linked glycosylation sites in GP5 are used for addition of sugar moieties, a series of mutants were generated in the bicistronic plasmid where all three potential glycosylation sites N34, N44, and N51 (FIG. 2A) were altered to alanines either individually or in various combinations (FIG. 2B). In plasmid-transfected cells, the proteins were radiolabeled and immunoprecipitated with anti-GP5 antibody. The immune complexes were either left untreated or treated with Endo H and examined by SDS-PAGE. As can be seen from the data presented in FIG. 2C, mutant GP5 proteins carrying single mutations (N34A, N44A or N51A) migrated as approximately 23.0 kDa protein species (lanes 4, 6 and 8, arrowhead). Upon Endo H treatment, these proteins migrated as ~18.0 kDa protein species (lanes 5, 7, and 9, respectively) similar to the wt GP5 after Endo H treatment (lane 3). The minor differences in electrophoretic mobility of the proteins is most likely reflective of the fact that the wt protein would retain all three N-acetylglucosamine residues following Endo H treatment as compared to the single mutants that would contain two such residues. The double mutants (N34/44A, N44/51A and N34/51A) produced protein species that migrated close to ~20.5 kDa protein (lanes 10, 12 and 14) and upon Endo H treatment, the size of the proteins was reduced to 18.0 kDa (lanes 11, 13, and 15). The triple mutant (N34/44/51A) generated a protein that migrated as 18.0 kDa protein (lane 16) and was resistant to Endo H digestion (lane 17).

Thus, from the above mutational studies, it is clear that all the three potential glycosylation sites are used for glycosylation to generate fully mature PRRSV GP5. It appears that all three glycosylation sites are modified by high-mannose type glycan moieties.

Recovery of Infectious PRRSV Virus with GP5 Mutants

To assess the importance of N-linked glycosylation in generation of infectious PRRSV, the coding regions of the mutant GP5 proteins were inserted into the full-length cDNA clone. Capped in vitro transcripts produced from the clones were electroporated into MARC-145 cells and generation of infectious PRRSV was examined. Our results showed that infectious virus was readily recovered from the cells electroporated with full-length transcripts containing mutations at N34, N51, and N34/51. However, under similar conditions of virus recovery, repeated attempts to recover other mutant viruses were unsuccessful. Although the growth kinetics of the recovered viruses were similar to that of the wt virus, the overall yield of FL-N34A and FL-N51A viruses containing mutations at N34 and N51 was approximately one log less in MARC-145 cells while that of FL-N34/51A with double mutations (N34/51A) was almost 1.5 log less than the wt PRRSV (FIG. 3A). The RT-PCR amplification of RNA from infected cells followed by nucleotide sequencing indicated that these viruses are stable, contained the desired mutations and no other mutations were detected in the entire GP5 region (data not shown).

Viral plaque assay was performed on MARC-145 cells to monitor the plaque phenotype of mutant viruses. The plaques generated by wt PRRSV were clear and distinct while the mutant viruses produced plaques that have different phenotypes. FL-N34A, FL-N51A and FL-N34/51A viruses generated plaques that were less distinct and many of the cells within the plaque appeared normal (FIG. 3B, open arrow). In addition, FL-N51A, FL-N34/51A produced some plaques in which the viruses failed to clear the cell monolayer (FIG. 3B, solid arrow). This data indicate that the recovered mutant viruses are indeed less cytopathic as compared to wt PRRSV.

Since we were unable to recover infectious PRRSV with mutant templates FL-N44A, FL-N31/44A, FL-N44/51A, and FL-N31/44/51A, it is possible that mutations in GP5 coding region may have affected some other functions of the RNA templates, such as packaging of the genomic RNA into particles. To address this, we examined whether cells expressing wt GP5 in trans could support packaging of mutant RNA templates that are otherwise defective in generating infectious PRRSV. BHK-21 cells transfected with pcDNA-GP5 were electroporated with in vitro transcripts and at 48 hrs post-electroporation, the culture supernatants were collected and used to infect naïve MARC-145 cells to determine the production of PRRSV pseudo-particles. If the pseudo-particles are generated, one would then expect to observe expression of the N protein in these infected MARC-145 cells. The expression of N is only possible when naïve MARC-145 cells receive full-length encapsidated mutant RNA genome that sets up replication following entry of the pseudo-particles into cells. Of all the mutants that could not be recovered previously, we were able to recover pseudo-particles containing two mutant full-length genomes (FL-N44A and FL-N34/44A) (FIG. 3C). Each green fluorescing cell in the mutant virus-infected culture represents one infectious pseudo-particle. Since these particles contain only the functional wt GP5 on the envelope but contain the coding sequences for non-functional mutant GP5 in the genome, they cannot produce infectious particles to spread to surrounding cells. Multiple attempts to recover pseudo-infectious particles with the other mutant templates (FL-N44/51A, and FL-N31/44/51A) were unsuccessful.

A quantitative estimation of the number of infectious pseudo-particles produced from these experiments suggests that approximately 1000 particles are produced per microgram of mutant RNA electroporated into the cells (FIG. 3D). This is approximately 100 fold less than that obtained with RNA encoding wt GP5. Production of such low levels of infectious pseudo-particles could be due to the fact that only about 5-10% of cells that expressed the wt GP5 received the full-length transcripts as seen by the expression of the N protein in these cells. It is also possible that low levels of expression of wt GP5 in the transfected cells may have contributed to the low levels of production of these pseudo-virions.

Examination of GP5 Incorporated into Mutant Viruses and Those Expressed in Infected Cells To determine the nature of GP5 protein incorporated into infectious virions produced from transfected cells, we generated radiolabeled PRRSV from cells infected with wt and mutant viruses. The extracellular virions present in the culture supernatant were pelleted by ultracentrifugation and GP5 present in these virions was examined by immunoprecipitation using anti-GP5 antibody and subsequent electrophoretic analysis. Results show the wt GP5 incorporated into virions migrated as a broadly diffuse band of ~25-27 kDa protein species (FIG. 4A, lane 1), which is partially resistant to Endo H digestion (lane 2). Mutant GP5 (N34A and N51A) incorporated into virions were sensitive to Endo H. Based on the size of the products generated following Endo H digestion, it appears that only one glycan moiety in these single site mutants is sensitive while the other is resistant. In contrast, the double mutant GP5 (N43/52A) was resistant to Endo H. Furthermore, Endo H digestion of GP5 from mutant viruses also produced very small amounts of GP5 protein backbone, indicating that these viruses incorporate GP5 proteins that contain Endo H-resistant as well as Endo H-sensitive glycan moieties.

Figure 4A:
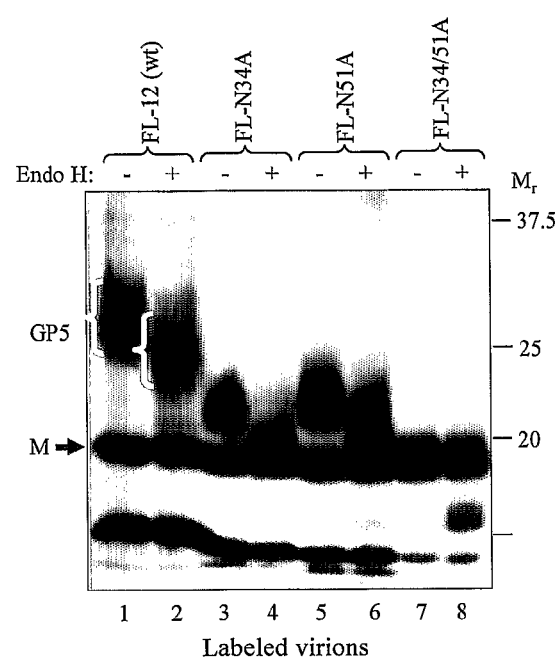
FIG. 4 illustrates an examination of GP5 incorporated into mutant virions and synthesized in mutant virus-infected cells. A. Radiolabeled virions from culture supernatants of infected cells were pelleted, GP5 protein was immunoprecipitated, treated with (+) or without (−) Endo H and analyzed by electrophoresis. GP5 with and without Endo H digestion in lanes 1 and 2 are shown by white brackets. B. Cells infected with various mutant viruses were radiolabeled, GP5 was immunoprecipitated, treated with (+) or without (−) Endo H and analyzed by electrophoresis. GP5 with and without Endo H digestion in lanes 2 and 3 are shown by white brackets. Mobility of proteins with relative molecular mass (Mr) in kilodaltons are shown on right side of each panel.
Figure 4B:
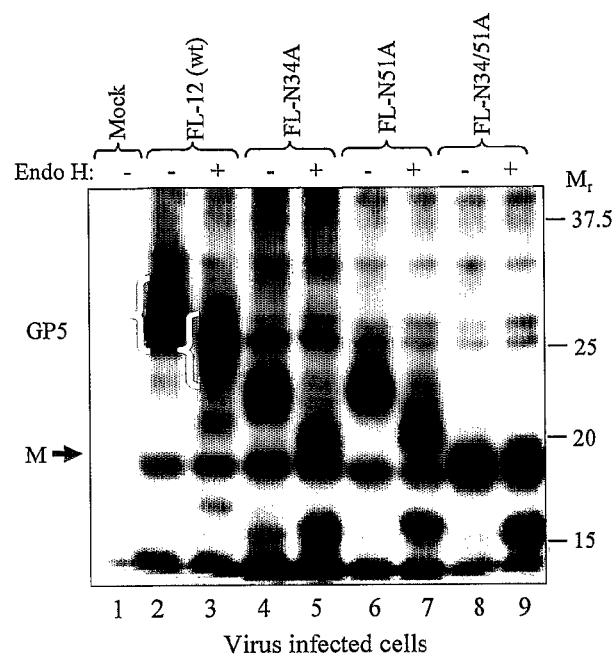

Since in cells transfected with the bicistronic vector, the wt as well as the mutant GP proteins were completely Endo H sensitive (FIGS. 1 and 2), we were surprised by the observation that GP5 on PRRS virions contained largely Endo H resistant forms. To examine if the Endo H resistant forms of the protein are also synthesized in infected cells, MARC-145 cells infected with wt or mutant PRRSV were radiolabeled, GP proteins were immunoprecipitated with anti-GP5 antibody and analyzed by electrophoresis with or without Endo H digestion. Results of such an experiment are shown in FIG. 4B. Majority of wt GP5 contained Endo H-resistant glycans at all three sites (lanes 2 and 3), whereas the two single mutants contained Endo H-resistant glycans only at one site (lanes 4-7). Some of the glycan moieties in the double mutant are resistant while others are sensitive to Endo H (lanes 8 and 9). Although the pattern of Endo H-resistance is similar to what is observed for virion-associated GP5, it is different from that observed in cells expressing both GP5 and M proteins (FIGS. 1 and 2). These results indicate that other viral proteins may play a role in further modification of glycans on GP5. Influence of hypoglycosylation of GP5 on PRRSV's ability to be neutralized by specific antibodies.

The level of glycosylation of viral glycoproteins that are involved in the interaction with viral receptors is known to affect the ability of virions to react with virus-neutralizing antibodies. To test whether this phenomenon occurs in the case of PRRSV, the PRRSV GP5 mutants with altered glycosylation patterns (FL-N34A, FL-N51A and FL-N34/51A) were compared with PRRSV wt (FL12) in their ability to be neutralized by convalescent antisera. For this, we used convalescent antisera (47 days p.i.) from 4 animals that had been infected with wt PRRSV. Similar doses (2,000 TCID50) of infectious PRRSV GP5 mutants (FL-N34A, FL-N51A and FL-N34/51A) as well as of the infectious clone-derived wt PRRSV (FL12) were used as challenge virus in serum-neutralization assays following our standard assay protocol and the set of 4 anti-wt PRRSV (FL12) sera used as reference. Table 3 shows the different end-point serum neutralizing titers obtained. Normally, a PRRSV wt-convalescent serum sample collected at 47-54 days p.i. contains moderate levels of wt PRRSV neutralizing activity (1:8 to 1:32, Tables 3 and 4), reflecting the relatively weak and tardy character of the neutralizing antibody response that is typical of infections with wt PRRSV. However, the use of hypoglycosylated PRRSV mutants (which lack one or two glycan moieties on the GP5 ectodomain) as challenge virus in the SN assays seem to have significantly enhanced the end-point of the reference sera, with end-point titer enhancement ranging from six to twenty-two fold (Table 3). This observation clearly suggests that the removal of one, and particularly two, of the glycan moieties increases the accessibility of the neutralizing epitope to specific antibodies. These results appear to indicate the presence of significant amount of PRRSV-neutralizing antibodies in the wt PRRSV-infected convalescent sera that would otherwise be undetectable because of the typical use of wt PRRSV containing fully glycosylated GP5 in SN assays.

TABLE 3

Effect of alteration of glycosylation pattern of PRRSV GP5 on the ability of the infectious virion to react with neutralizing antibodies. Numbers in Table 3 correspond to the inverse end point dilution showing neutralization (SN endpoint).

| Serum from animals infected with $10^5$ | PRRSV strain used as challenge for SN test | | | |
|---|---|---|---|---|
| $TCID_{50}$ of wt PRRSV FL12 | Wt PRRSV(FL12) | FL-N34A | FL-N51A | FL-N34/51A |
| Animal No. 11404(47 days pi) | 1:32 | 1:256 | 1:256 | 1:32,768 |
| Animal No. 11346(47 days pi) | 1:8 | 1:64 | 1:256 | 1:16,384 |
| Animal No. 11457(47 days pi) | 1:16 | ND | 1:128 | 1:2,048 |
| Animal No. 11407(47 days pi) | 1:8 | ND | 1:64 | 1:2,048 |

Influence of Hypoglycosylation of GP5 on PRRSV's Ability to Induce Neutralizing Antibodies In Vivo One remarkable effect that has been reported where carbohydrate removal from a viral envelope glycoprotein leads to production of high titers of neutralizing antibodies against the mutant virus when this mutant is used for in vivo inoculation of the host; in some cases also inducing higher titers of antibody to the wt virus than the wt virus itself. We infected groups of pigs with identical doses of either the wt PRRSV FL12 or of each of the mutants with altered glycosylation patterns. Interestingly, clinical/virological assessment of the infection by evaluation of rectal temperature and evaluation of viremia at days 4, 7 and 10 p.i. indicated a similar pattern of infection in all groups as previously described for FL12 without evidence of virulence attenuation or exacerbation for either of the mutants (data not shown). However, the sequential sampling of serum from these animals throughout a period of 48 days indicated pronounced differences between the wt PRRSV and the mutants in their kinetics of induction of a PRRSV-neutralizing antibody response (Tables 4A and 4B). The mutants developed an early and more robust homologous neutralizing antibody response than that developed by wt PRRSV, to the point where, in the case of the mutants, the characteristically sluggish and meager nature of PRRSV-neutralizing antibody response appears to have been corrected (Table 4B). The kinetics of appearance of mutant-homologous neutralizing antibodies (Table 4B) indicate a more regular neutralizing antibody seroconversion consistent with that described for other viral infections such as influenza or Pseudorabies virus but not for PRRSV. Of utmost importance is the fact that the infection with GP5 glycosylation mutants induced a wt PRRSV-specific neutralizing antibody response that is significantly higher than the response with the wt PRRSV itself. The mutant viruses FL-N34 and FL-N51A induced five-fold higher (p<0.05) levels of neutralizing antibody titer against wt PRRSV than the wt PRRSV itself while the mutant FL-N34/51 induced six-fold higher (p<0.01) titer of wt PRRSV-neutralizing antibodies than wt PRRSV itself (Table 4B).

TABLE 4A

| Group infected with | Neutralizing antibody activity against FL12 at different times PI (days PI) | | | |
|---|---|---|---|---|
| | 0 | 14 | 21 | 48 |
| Wt PRRSV FL-12 | 1.0* | 1.0 | 3.2 | 25.4 |
| FL-N34A | 1.0 | 1.0 | 4.0 | 128.0 |
| FL-N51A | 1.0 | 1.0 | 4.0 | 128.0 |
| FL-N34/51A | 1.0 | 1.0 | 5.0 | 161.3 |

Table 4A. Effect of alteration of glycosylation pattern of PRRSV GP5 on the ability of the PRRSV strains to induce neutralizing antibodies to the wt PRRSV (4A) or to the infecting, homologous strain (4B) (*) Numbers in Table 4A and B correspond to geometric mean of the SN end-point for the group (n = 3).

TABLE 4B

| Group infected with | End-point titer against the homologous infecting strain at different PI periods | | | |
|---|---|---|---|---|
| | 0 | 14 | 21 | 48 |
| Wt PRRSV FL-12 | 1.0 | 1.0 | 3.2 | 25.4 |
| FL-N34A | 1.0 | 4.0 | 128 | 8,192 |
| FL-N51A | 1.0 | 4.0 | 128 | 2,048 |
| FL-N34/51A | 1.0 | 4.0 | 64 | 4,096 |

Discussion

In the present study, we examined the influence of glycosylation of GP5 of PRRSV in recovery of infectious virus, its role in the ability of the mutant viruses to be neutralized by antibodies, and in inducing neutralizing antibodies in vivo. We have found that all three potential glycosylation sites (N34, N44, and N51) in GP5 are used for addition of glycan moieties. Our results reveal that glycan addition at N44 site is most critical for recovery of infectious virus. Furthermore, our results show that PRRSV containing hypoglycosylated forms of GP5 are exquisitely sensitive to neutralization by antibodies and that the mutant viruses induce significantly higher levels of neutralizing antibodies not only to the homologous mutant viruses but also to wt PRRSV.

Confirmation that all three potential N-linked glycosylation sites are used for glycan addition in GP5 was provided by using mutants with alterations at single or multiple sites (FIG. 2). Biochemical studies showed that the PRRSV GP5 protein when coexpressed with M protein in transfected cells, contains Endo H sensitive high-mannose type glycans. The observation that majority of GP5 incorporated into virions is resistant to Endo H (FIG. 4A) whereas GP5 expressed in the presence of M protein in transfected cells is fully Endo H sensitive, is intriguing. It is possible that GP5 when expressed in the presence of M protein in transfected cells, accumulates mostly in the ER or in the cis-Golgi region and therefore remains Endo H sensitive. However, in PRRSV-infected cells, GP5 may interact with additional viral proteins and the transport of GP5 beyond ER or cis-Golgi is facilitated through formation of complexes with the other viral proteins. Consistent with this interpretation, we have observed that in wt or mutant PRRSV-infected cells, GP5 protein is also resistant to Endo H. We suggest that GP5, which is synthesized in the ER in infected cells, is transported to the medial- and/or trans-Golgi regions where majority of GP5 molecules acquire Endo H resistance prior to being incorporated into PRRSV virions. Several studies with arteriviruses including PRRSV suggest that GP5 and M protein form heterodimer, which may play a key role in viral infectivity. In EAV and LDV, direct interaction of GP5 and M protein through formation of disulfide bridges have been demonstrated. Such interactions may occur prior to further processing of N-linked oligosaccharide side chains, presumably before GP5 is transported out of the ER or the cis-Golgi compartment.

It is interesting to note that the pattern of Endo H resistance of GP5 incorporated into wt and mutant virions is different. While the majority of GP5 molecules in wt PRRSV were Endo H resistant, most of GP5 molecules in the single site mutant virions (FL-N34A and FL-N51A) were Endo H sensitive (FIG. 4A). Furthermore, of the two glycans moieties in these mutants, only one was sensitive while the other was resistant. The double mutant (FL-N34/51A) virion also incorporated GP5 that contained glycans, some of which were also sensitive to Endo H. These data are consistent with the interpretation that wt as well as mutant PRRSV virions incorporate a mixed population of GP5 molecules that contain different glycan moieties at different sites. Previous studies demonstrating incorporation of differentially glycosylated forms of GP5 into wt PRRSV virions further strengthens our interpretation. From the pattern of Endo H sensitivity of GP5 incorporated into the virions, it is tempting to speculate that N44 site may contain the Endo H resistant glycans, although some GP5 molecules with Endo H sensitive glycans at this site were incorporated into the virions. Whether this unusual pattern of glycans at various sites in GP5 and incorporation of various forms of GP5 into virions has any relevance to the pattern of immune response seen in PRRSV infected animals remains to be investigated.

In a recent study, it was shown that of the two N-linked glycosylation sites (N46 and N53) in GP5 of Lelystad PRRSV, glycosylation of N46 residue was strongly required for virus particle production. Infectious virus yield was reduced by approximately 100-fold with mutation at N46. Our results suggest that glycan addition at N44 (for North American PRRSV) is absolutely essential for recovery of infectious PRRSV. It is possible then that the European and North American isolates of PRRSV may somewhat differ in their requirements for N-linked glycosylation for production of infectious viruses. In this regard, it is of note that the Lelystad virus contains only two N-linked glycosylation sites whereas the North American isolate we have used in this study contain three such sites.

The GP5 is the most important glycoprotein of PRRSV involved in the generation of PRRSV-neutralizing antibodies and protective immunity. Our results reveal that the absence of glycans at residues 34 and 51 in the GP5 ectodomain, while generating viable PRRSV mutants, enhance both the sensitivity of these mutants to neutralization by antibodies as well as the immunogenicity of the nearby neutralization epitope. The immediate effect of the absence of glycans in GP5 of mutant PRRSVs has been the increased sensitivity of the viruses to neutralization by convalescent sera from pigs infected with wt PRRSV (Table 3). Studies with HIV-1 and SIV have shown that acquisition or removal of glycans in the variable loops of gp160 modify their sensitivity to neutralization. Therefore, it has been postulated that glycans play at least two types of essential roles during viral envelope glycoprotein biosynthesis. In one case, lack of glycans entails defects of the glycoprotein and thus, in the overall viability of the viral strain. We postulate that glycans at N44 of PRRSV GP5 serve a similar role. In the second case, the glycans potentially serve to shield viral proteins against neutralization by antibodies. For PRRSV GP5, glycans at N34 and N51 may have a similar role. In the case of HIV, "glycan shielding" is postulated to be a primary mechanism to explain evasion from neutralizing immune response, thus ensuring in vivo persistence of HIV. This invites to draw some parallel comparisons with the PRRSV. Infection with PRRSV, which is known to persist for several months in individual animals, presents an unusual behavior in terms of induction of virus-specific neutralizing immune response. It is well established that animals infected with PRRSV usually take longer than normal time to establish a detectable PRRSV-neutralizing antibody response. Once established, this PRRSV-neutralizing response is weak, and varies significantly from animal to animal. The delay in neutralizing antibody response has been postulated to be due to the presence of a nearby immunodominant decoy epitope (amino acid positions 27 to 30), which evokes a robust, early, non-protective immune response that masks and/or slows the response to the neutralizing epitope (amino acid position 37 to 45) (26, 38). While this being a plausible explanation for the atypical character of the PRRSV-neutralizing antibody response, it remains to be tested. In our laboratory, deletion of the decoy epitope has consistently proven lethal to the recovery of infectious PRRSV (Ansari et al., unpublished data), thus making it difficult to test this hypothesis.

It is possible that an alternative or complementary mechanism to explain the peculiar nature of the PRRSV-neutralizing response could be envisioned by the "glycan shielding" phenomenon proposed for HIV and SIV. The use of mutant PRRSVs lacking one or two glycan moieties in our studies provides evidence for the first time the presence of large amounts of PRRSV neutralizing antibodies in the sera of wt PRRSV-infected animals that were otherwise undetectable because of the use of wt PRRSV in the SN assays. The PRRSV-neutralizing antibodies, while present in the host's response, are unable to react with the infecting wt PRRSV virions due to the blocking or shielding of the neutralizing epitope by the glycan moieties on GP5.

One important precedent for neutralization escape by glycosylation of glycoproteins in arteriviruses has been described for lactate dehydrogenase-elevating virus (LDV). LDV is highly resistant to antibody neutralization due to the heavy glycan shielding of their major glycoprotein, VP-3, however, certain naturally occurring strains of LDV are highly susceptible to neutralization, due to loss of two glycosylation sites on the ectodomain of the VP-3. Interestingly, this neutralization-sensitive phenotype correlates with a high degree of neurotropism in the host acquired by these easily neutralizable LDV strains. Such neuropathogenicity enhancement probably reflects the facilitation of interaction of the viral glycoproteins with receptors in neural cells, possibly due to the absence of glycan shielding. In the young pig model that we used for inoculation with PRRSV, we were not able to detect pathogenic differences between any of the mutant PRRSVs and the wt PRRSV, although we limited our observations to temperature and viremia measurements. It is possible that under different experimental conditions (i.e., in a pregnant sow model), some alterations in pathogenicity of these mutant PRRSVs might be observed. It is not known whether the finding of naturally occurring hypoglycosylated PRRSV strains is a common occurrence, although previous reports have suggested their presence.

A remarkable observation in our experiments has been that the GP5 mutants, when infecting pigs in vivo, can outperform the wt PRRSV in their ability to mount a sizable wt PRRSV-neutralizing response at late phases of infection (Table 4A). In a parallel scenario, we have observed not only higher neutralizing titers against homologous PRRSV mutants but also sizable titers against wt PRRSV (Table 4A). In addition, the response occurred earlier, with neutralizing titers detectable at 14 days p.i., an observation not typically noted with wt PRRSV infection (Table 4B). The increased neutralization of wt PRRSV by sera from pigs infected with the PRRSV mutants suggests that glycans were masking neutralizing epitope(s) that do not induce neutralizing antibodies when glycans are present. This observation has great significance on the design of better, more efficacious PRRSV vaccines, suggesting that new, rationally-designed vaccines should carry modifications in the glycosylation pattern of GP5 in order to enhance the production of neutralizing antibodies. In addition, it will be important to study the effects that this removal of carbohydrates from immunologically prominent glycoproteins of PRRSV may have on increasing SN titers not only to the homologous immunizing strain but also to diverse unrelated PRRSV strains.

Example 2

Identification of N-Linked Glycosylation Sites in North American and European PRRSV Isolates To identify N-linked glycosylation sites corresponding to asparagine 34 or asparagine 51 in a reference GP5 protein of SEQ ID NO:1 that can be inactivated and used in the methods of this invention, the GP5 proteins of either a desired North American PRRSV isolate (FIG. 5) or a European PRRSV isolate (FIG. 6) are aligned with reference GP5 protein of SEQ ID NO:1 (North American strain NVSL 97-7895). In this example, the alignments were created with the MegAlign™ program from DNASTAR, Inc. (Madison, Wis., USA) using the Jotun-Hein method of alignment (Hein, J. J. In Methods in Enzymology, Vol. 183: pp. 626-645, 1990). Multiple sequence alignment parameters were a gap penalty of 11 and a gap length penalty of 3. For pairwise comparisons, a Ktuple value of 2 was used.

In FIG. 5, it is clear that the N-linked glycosylation site corresponding to asparagine 51 of the reference GP5 protein of SEQ ID NO:1 present in all of the North American PRRSV isolates shown and comprises the N-linked glycosylation site "NGT". This N-linked glycosylation site can be inactivated by substituting codons encoding other amino acid residues such as glutamine or alanine for asparagine 51 in the corresponding polynucleotide sequence. In these instances, the corresponding amino acid sequence in the hypoglycosylated North American PRRSV GP5 protein variant would comprise the sequences such as "QGT", "AGT", or "XGT", where X is any amino acid other than asparagine. These or other hypoglycosylated variants of the North American PRRSV isolates where N-linked glycosylation site corresponding to asparagine 51 is inactivated can also be combined with other hypoglycosylated GP5 variants where other N-linked glycosylation sites are inactivated.

It is also clear from FIG. 5, that the N-linked glycosylation site corresponding exactly to asparagine 34 of the reference GP5 protein of SEQ ID NO:1 is present in only certain North American PRRSV isolates. More specifically, the GP5 proteins of North American PRRSV isolates IAF-BAJ (SEQ ID NO:3), 94-3182 (SEQ ID NO:7), and 94-287 (SEQ ID NO:8) contain the N-linked glycosylation site corresponding exactly to asparagine 34 of the reference GP5 protein of SEQ ID NO:1 and comprises the N-linked glycosylation site "NSS". This N-linked glycosylation site of SEQ ID NO:3, 7, and 8 can be inactivated by substituting codons encoding other amino acid residues such as glutamine or alanine for asparagine 34 in the corresponding polynucleotide sequence. In these instances, the corresponding amino acid sequence in the hypoglycosylated North American PRRSV GP5 protein variant would comprise the sequences such as "QSS", "ASS", or "XSS", where X is any amino acid other than asparagine.

In other North American PRRSV isolates that lack the N-linked glycosylation site corresponding exactly to asparagine 34 of the reference GP5 protein of SEQ ID NO:1, other N-linked glycosylation sites located at residue 30 (FIG. 5 "NAS" in SEQ ID NO:2, 3, 4, 6, 7, 8, 9, 11, 13), and residue 33 (FIG. 5 "NNS" in SEQ ID NO:3, 8; "NSS" in SEQ ID NO:6, 10, "NDS" in SEQ ID NO:11, 13) can also be inactivated. In other words, N-linked glycosylation sites in other North American isolates located at amino acid positions corresponding to residues 30 and 33 of the reference GP5 protein of SEQ ID NO:1 can also be inactivated and used in the methods of this invention.

In FIG. 6, it is clear that the N-linked glycosylation site corresponding to asparagine 51 of the reference GP5 protein of SEQ ID NO:1 is also present in a representative European PRRSV isolate and comprises the N-linked glycosylation site "NGT". This N-linked glycosylation site can be inactivated by substituting codons encoding other amino acid residues such as glutamine or alanine for asparagine 51 in the corresponding polynucleotide sequence. In these instances, the corresponding amino acid sequence in the hypoglycosylated European PRRSV GP5 protein variant would comprise the sequences such as "QGT", "AGT", or "XGT", where X is any amino acid other than asparagine. These or other hypoglycosylated variants of the European PRRSV isolates where N-linked glycosylation site corresponding to asparagine 51 is inactivated can also be combined with other hypoglycosylated GP5 variants where other N-linked glycosylation sites are inactivated.

In view of the foregoing, it will be seen that the several advantages of the invention are achieved and attained.

The embodiments were chosen and described in order to best explain the principles of the invention and its practical application to thereby enable others skilled in the art to best utilize the invention in various embodiments and with various modifications as are suited to the particular use contemplated.

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

A variety of patent and non-patent references are disclosed herein, each of which is expressly incorporated herein by reference in their entirety.

---

What is claimed is:

1. A composition comprising a polynucleotide encoding a hypoglycosylated North American PRRSV GP5 polypeptide variant wherein at least one N-linked glycosylation site corresponding to asparagine 51 in a reference GP5 protein of SEQ ID NO: 1 is inactivated by mutation, and a therapeutically acceptable carrier.

2. The composition of claim 1, wherein said polynucleotide comprises an infectious North American PRRSV RNA molecule.

3. The composition of claim 1, wherein said polynucleotide comprises a DNA molecule that encodes an infectious North American PRRSV RNA molecule.

4. The composition of claim 1, wherein said polynucleotide comprises a DNA molecule wherein a promoter active in mammalian cells is operably linked to said polynucleotide encoding said hypoglycosylated North American PRRSV GP5 polypeptide variant.

5. The composition of claim 4, wherein said promoter is a CMV promoter.

6. The composition of claim 1, wherein said N-linked glycosylation site is inactivated by replacing a codon encoding said asparagine 51 with a codon encoding an amino acid other than asparagine.

7. The composition of claim 6, wherein said codon encoding an amino acid other than asparagine encodes an alanine or a glutamine residue.

8. The composition of claim 1, wherein said polynucleotide encodes a hypoglycosylated North American PRRSV GP5 polypeptide variant protein wherein both of said N-linked glycosylation sites corresponding to asparagine 34 and asparagine 51 in a North American reference GP5 protein of SEQ ID NO:1 are inactivated.

9. The composition of claim 8, wherein both of said N-linked glycosylation sites are inactivated by replacing codons encoding said asparagine 34 and said asparagine 51 with codons encoding an amino acid other than asparagine.

10. The composition of claim 9, wherein said codons encoding another amino acid encode either an alanine or a glutamine residue.

11. The composition of claim 8, wherein one of said N-linked glycosylation sites is inactivated by replacing one codon encoding said asparagine 34 or said asparagine 51 with a codon encoding an amino acid other than asparagine.

12. The composition of claim 1, wherein said therapeutically acceptable carrier is selected from the group consisting of a protein, a buffer, a surfactant, and a polyethylene glycol polymer, or any combination thereof.

13. The composition of claim 1, wherein said composition further comprises at least one adjuvant.

14. The composition of claim 13, wherein said adjuvant is selected from the group consisting of aluminum hydroxide, Quil A, an alumina gel suspension, mineral oils, glycerides, fatty acids, fatty acid by-products, mycobacteria, and CpG oligodeoxynucleotides, or any combination thereof.

15. The composition of claim 13, wherein said composition further comprises a second adjuvant is selected from the group consisting of interleukin 1 (IL-1), IL-2, IL4, IL-5, IL6, IL-12, gamma interferon (g-IFN), cell necrosis factor, MDP (muramyl dipeptide), immuno stimulant complex (ISCOM), and liposomes.

16. The composition of claim 1, wherein said polynucleotide comprises a viral vector selected from the group consisting of a vaccinia virus vector, a herpes simplex viral vector, an adenovirus vector, an alphavirus vector, and a TGEV vector.

17. An isolated polynucleotide encoding a hypoglycosylated North American PRRSV GP5 polypeptide variant wherein at least one N-linked glycosylation site corresponding to asparagine 51 in a reference GP5 protein of SEQ ID NO:1 is inactivated by mutation.

18. The isolated polynucleotide of claim 17, wherein both N-linked glycosylation sites corresponding to asparagine 34 and asparagine 51 in SEQ ID NO:1 are inactivated.

19. The isolated polynucleotide of claim 17, wherein said polynucleotide comprises an infectious North American PRRSV RNA molecule.

20. The isolated polynucleotide of claim 17, wherein said polynucleotide comprises a DNA molecule that encodes an infectious North American PRRSV RNA molecule.

21. The isolated polynucleotide of claim 17, wherein said polynucleotide comprises a DNA molecule wherein a promoter active in mammalian cells is operably linked to said polynucleotide encoding said hypoglycosylated North American PRRSV GP5 polypeptide variant.

22. The isolated polynucleotide of claim 21, wherein said promoter is a CMV promoter.

23. The isolated polynucleotide of claim 17, wherein said N-linked glycosylation site corresponding to asparagine 51 is inactivated by replacing a codon encoding said asparagine 51 with a codon encoding an amino acid other than asparagine.

24. The isolated polynucleotide of claim 23, wherein said codon encoding another amino acid encodes an alanine or a glutamine residue.

25. The isolated polynucleotide of claim 17, wherein an N-linked glycosylation site corresponding to asparagine 34 in a reference GP5 protein of SEQ ID NO:1 is inactivated.

26. The isolated polynucleotide of claim 25, by replacing a codon encoding said asparagine 34 with a codon encoding an amino acid other than asparagine.

27. The isolated polynucleotide of claim 25, wherein said codon encoding another amino acid encodes an alanine or a glutamine residue.

28. The isolated polynucleotide of claim 25, wherein one of said N-linked glycosylation sites is inactivated by replacing one codon encoding said asparagine 34 or said asparagine 51 with a codon encoding an amino acid other than asparagine.

29. The isolated polynucleotide of claim 17, wherein said polynucleotide comprises a viral vector selected from the group consisting of a vaccinia virus vector, a herpes simplex viral vector, an adenovirus vector, an alphavirus vector and a TGEV vector.

* * * * *

SEQUENCE LISTING

```
<160> NUMBER OF SEQ ID NOS: 26

<210> SEQ ID NO 1
<211> LENGTH: 200
<212> TYPE: PRT
<213> ORGANISM: Porcine reproductive and respiratory syndrome virus

<400> SEQUENCE: 1

Met Leu Gly Arg Cys Leu Thr Ala Gly Cys Cys Ser Arg Leu Leu Ser
1               5                   10                  15

Leu Trp Cys Ile Val Pro Phe Cys Phe Ala Ala Leu Val Asn Ala Asn
            20                  25                  30

Ser Asn Ser Ser Ser His Leu Gln Leu Ile Tyr Asn Leu Thr Leu Cys
35                  40                  45

Glu Leu Asn Gly Thr Asp Trp Leu Lys Asp Lys Phe Asp Trp Ala Val
50                  55                  60

Glu Thr Phe Val Ile Phe Pro Val Leu Thr His Ile Val Ser Tyr Gly
65                  70                  75                  80

Ala Leu Thr Thr Ser His Phe Leu Asp Thr Val Gly Leu Val Thr Val
85                  90                  95

Ser Thr Ala Gly Phe Tyr His Gly Arg Tyr Val Leu Ser Ser Ile Tyr
100                 105                 110

Ala Val Cys Ala Leu Ala Ala Leu Ile Cys Phe Val Ile Arg Leu Ala
115                 120                 125

Lys Asn Cys Met Ser Trp Arg Tyr Ser Cys Thr Arg Tyr Thr Asn Phe
130                 135                 140

Leu Leu Asp Thr Lys Gly Arg Leu Tyr Arg Trp Arg Ser Pro Val Ile
145                 150                 155                 160

Ile Glu Lys Gly Gly Lys Val Glu Val Glu Gly His Leu Ile Asp Leu
165                 170                 175

Lys Arg Val Val Leu Asp Gly Ser Val Ala Thr Pro Leu Thr Arg Val
180                 185                 190
```

Ser Ala Glu Gln Trp Gly Arg Leu
195                 200

<210> SEQ ID NO 2
<211> LENGTH: 200
<212> TYPE: PRT
<213> ORGANISM: Porcine reproductive and respiratory syndrome virus

<400> SEQUENCE: 2

Met Leu Gly Lys Cys Leu Thr Ala Gly Cys Cys Ser Gln Leu Pro Phe
1               5                   10                  15

Leu Trp Cys Ile Val Pro Phe Cys Phe Ala Ala Leu Val Asn Ala Ser
        20                  25                  30

Ser Ser Ser Ser Gln Leu Gln Ser Ile Tyr Asn Leu Thr Ile Cys
35              40                  45

Glu Leu Asn Gly Thr Asp Trp Leu Asn Lys Asn Phe Asp Trp Ala Val
50                  55                  60

Glu Thr Phe Val Ile Phe Pro Val Leu Thr His Ile Val Ser Tyr Gly
65                  70                  75                  80

Ala Leu Thr Thr Ser His Phe Leu Asp Ala Val Gly Leu Ile Thr Val
                85                  90                  95

Ser Thr Ala Gly Tyr Tyr His Gly Arg Tyr Val Leu Ser Ser Val Tyr
100                 105                 110

Ala Val Cys Ala Leu Ala Ala Leu Ile Cys Phe Val Ile Arg Leu Thr
115                 120                 125

Lys Asn Cys Met Ser Trp Arg Tyr Ser Cys Thr Arg Tyr Thr Asn Phe
130                 135                 140

Leu Leu Asp Ser Lys Gly Lys Leu Tyr Arg Trp Arg Ser Pro Val Ile
145                 150                 155                 160

Ile Glu Lys Gly Gly Lys Val Glu Val Asp Gly His Leu Ile Asp Leu
                165                 170                 175

Lys Arg Val Val Leu Asp Gly Ser Ala Ala Thr Pro Val Thr Lys Val
180                 185                 190

Ser Ala Glu Gln Trp Cys Arg Pro
195                 200

<210> SEQ ID NO 3
<211> LENGTH: 200
<212> TYPE: PRT
<213> ORGANISM: Porcine reproductive and respiratory syndrome virus

<400> SEQUENCE: 3

Met Leu Gly Lys Cys Leu Thr Ala Gly Cys Cys Ser Gln Leu Pro Phe
1               5                   10                  15

Leu Trp Cys Ile Val Pro Phe Cys Phe Ala Ala Leu Val Asn Ala Ser
        20                  25                  30

Asn Asn Ser Ser Ser Gln Leu Gln Ser Ile Tyr Asn Leu Thr Ile Cys
35              40                  45

Glu Leu Asn Gly Thr Asp Trp Leu Asn Lys Asn Phe Asp Trp Ala Val
50                  55                  60

Glu Thr Phe Val Ile Phe Pro Val Leu Thr His Ile Val Ser Tyr Gly
65                  70                  75                  80

Ala Leu Thr Thr Ser His Phe Leu Asp Thr Val Gly Leu Ile Thr Val
                85                  90                  95

Ser Thr Ala Gly Tyr Tyr His Gly Arg Tyr Val Leu Ser Ser Val Tyr
100                 105                 110

Ala Val Cys Ala Leu Ala Ala Leu Ile Cys Phe Val Ile Arg Leu Thr
115                 120                 125

Lys Asn Cys Met Ser Trp Arg Tyr Ser Cys Thr Arg Tyr Thr Asn Phe
130                 135                 140

Leu Leu Asp Ser Lys Gly Lys Leu Tyr Arg Trp Arg Ser Pro Val Ile
145                 150                 155                 160

Ile Glu Lys Gly Gly Lys Val Glu Val Asp Gly His Leu Ile Asp Leu
165                 170                 175

Lys Arg Val Val Leu Asp Gly Ser Ala Ala Thr Pro Val Thr Lys Val
180                 185                 190

Ser Ala Glu Gln Trp Cys Arg Pro
195                 200

<210> SEQ ID NO 4
<211> LENGTH: 200
<212> TYPE: PRT
<213> ORGANISM: Porcine reproductive and respiratory syndrome virus

<400> SEQUENCE: 4

Met Leu Gly Lys Cys Leu Thr Val Gly Tyr Cys Ser Gln Leu Pro Phe
1               5                   10                  15

Leu Trp Cys Ile Val Pro Phe Cys Phe Ala Ala Leu Val Asn Ala Ser
20                  25                  30

Ser Thr Ser Ser Ser His Leu Gln Leu Ile Tyr Asn Leu Thr Ile Cys
35                  40                  45

Glu Leu Asn Gly Thr Asp Trp Leu Asn Glu Lys Phe Asp Trp Ala Val
50                  55                  60

Glu Thr Phe Val Ile Phe Pro Val Leu Thr His Ile Val Ser Tyr Gly
65                  70                  75                  80

Ala Leu Thr Thr Ser His Phe Leu Asp Thr Val Gly Leu Val Thr Val
85                  90                  95

Ser Thr Ala Gly Tyr Tyr His Gly Arg Tyr Val Leu Ser Ser Ile Tyr
100                 105                 110

Ala Val Cys Ala Leu Ala Ala Leu Ile Cys Phe Val Ile Arg Leu Val
115                 120                 125

Lys Asn Cys Met Ser Trp Arg Ty

```
Thr Asp Ser Ser Ser His Leu Gln Leu Ile Tyr Asn Leu Thr Ile Cys
 35                  40                  45

Glu Leu Asn Gly Thr Asp Trp Leu Asn Asp Lys Phe Asp Trp Ala Val
 50                  55                  60

Glu Thr Phe Val Ile Phe Pro Val Leu Thr His Ile Val Ser Tyr Gly
 65                  70                  75                  80

Ala Leu Thr Thr Ser His Phe Leu Asp Thr Val Gly Leu Ile Thr Val
 85                  90                  95

Ser Thr Ala Gly Tyr Tyr His Gly Arg Tyr Val Leu Ser Ser Ile Tyr
100                 105                 110

Ala Val Cys Ala Leu Ala Ala Leu Ile Cys Phe Ala Ile Arg Leu Thr
115                 120                 125

Lys Asn Cys Met Ser Trp Arg Tyr Ser Cys Thr Arg Tyr Thr Asn Phe
130                 135                 140

Leu Leu Asp Thr Lys Gly Lys Leu Tyr Arg Trp Arg Ser Pro Val Ile
145                 150                 155                 160

Ile Glu Arg Gln Gly Lys Val Glu Val Glu Gly His Leu Ile Asp Leu
165                 170                 175

Lys Arg Val Val Leu Asp Gly Ser Ala Ala Thr Pro Val Thr Arg Val
180                 185                 190

Ser Ala Glu Arg Trp Gly Arg Pro
195                 200

<210> SEQ ID NO 6
<211> LENGTH: 200
<212> TYPE: PRT
<213> ORGANISM: Porcine reproductive and respiratory syndrome virus

<400> SEQUENCE: 6

Met Leu Gly Lys Cys Leu Thr Ala Gly Cys Cys Ser Arg Leu Pro Phe
  1               5                  10                  15

Leu Trp Cys Ile Val Pro Phe Cys Phe Ala Ala Leu Val Asn Ala Ser
 20                  25                  30

Asn Ser Ser Ser Ser His Leu Gln Leu Ile Tyr Asn Leu Thr Ile Cys
 35                  40                  45

Glu Leu Asn Gly Thr Asp Trp Leu Asp Lys Lys Phe Asp Trp Ala Val
 50                  55                  60

Glu Thr Phe Val Ile Phe Pro Val Leu Thr His Ile Val Ser Tyr Gly
 65                  70                  75                  80

Ala Leu Thr Thr Ser His Phe Leu Asp Thr Val Gly Leu Ile Thr Val
 85                  90                  95

Ser Thr Ala Gly Tyr Tyr His Gly Arg Tyr Val Leu Ser Ser Ile Tyr
100                 105                 110

Ala Val Cys Ala Leu Ala Ala Leu Ile Cys Phe Val Ile Arg Leu Thr
115                 120                 125

Lys Asn Cys Met Ser Trp Arg Tyr Ser Cys Thr Arg Tyr Thr Asn Phe
130                 135                 140

Leu Leu Asp Thr Lys Gly Lys Leu Tyr Arg Trp Arg Ser Pro Val Ile
145                 150                 155                 160

Ile Glu Lys Arg Gly Lys Val Glu Val Glu Gly Gln Leu Ile Asp Leu
165                 170                 175

Lys Arg Val Val Leu Asp Gly Ser Ala Ala Thr Pro Ile Thr Lys Val
180                 185                 190

Ser Ala Glu Gln Trp Gly Arg Pro
195                 200
```

<210> SEQ ID NO 7
<211> LENGTH: 200
<212> TYPE: PRT
<213> ORGANISM: Porcine reproductive and respiratory syndrome virus

<400> SEQUENCE: 7

```
Met Leu Gly Lys Cys Leu Thr Ala Gly Cys Cys Ser Arg Leu Pro Phe
1               5                   10                  15

Leu Trp Cys Ile Val Pro Phe Cys Phe Ala Val Leu Val Asn Ala Ser
            20                  25                  30

Pro Asn Ser Ser Ser His Leu Gln Leu Ile Tyr Asn Leu Thr Ile Cys
        35                  40                  45

Glu Leu Asn Gly Thr Asp Trp Leu Asn Ala Arg Phe Asp Trp Ala Val
    50                  55                  60

Glu Thr Phe Val Ile Phe Pro Val Val Thr His Ile Val Ser Tyr Gly
65                  70                  75                  80

Ala Leu Thr Thr Ser His Phe Leu Asp Thr Val Gly Leu Val Thr Val
                85                  90                  95

Ser Thr Ala Gly Tyr Tyr His Gly Arg Tyr Val Leu Ser Ser Ile Tyr
            100                 105                 110

Ala Val Cys Ala Leu Ala Ala Leu Ile Cys Phe Val Ile Arg Leu Ala
        115                 120                 125

Lys Asn Cys Met Ser Trp Arg Tyr Ser Cys Thr Arg Tyr Thr Asn Phe
    130                 135                 140

Leu Leu Asp Thr Lys Gly Lys Leu Tyr Arg Trp Arg Ser Pro Val Ile
145                 150                 155                 160

Ile Glu Lys Arg Gly Lys Val Glu Val Glu Gly His Leu Ile Asp Leu
                165                 170                 175

Lys Arg Val Val Leu Asp Gly Ser Ala Ala Thr Pro Val Thr Arg Val
            180                 185                 190

Ser Ala Glu Gln Trp Cys Arg Pro
        195                 200
```

<210> SEQ ID NO 8
<211> LENGTH: 200
<212> TYPE: PRT
<213> ORGANISM: Porcine reproductive and respiratory syndrome virus

<400> SEQUENCE: 8

```
Met Leu Gly Lys Cys Leu Thr Ala Gly Cys Cys Ser Gln Leu Pro Phe
1               5                   10                  15

Leu Trp Cys Ile Val Pro Phe Cys Phe Ala Ala Leu Val Asn Ala Ser
            20                  25                  30

Asn Asn Ser Ser Ser His Leu Gln Leu Ile Tyr Asn Leu Thr Ile Cys
        35                  40                  45

Glu Leu Asn Gly Thr Asp Trp Leu Asn Asp Lys Phe Asp Trp Ala Val
    50                  55                  60

Glu Thr Phe Val Ile Phe Pro Val Leu Thr His Ile Val Ser Tyr Gly
65                  70                  75                  80

Ala Leu Thr Thr Ser His Phe Leu Asp Thr Val Gly Leu Ile Thr Val
                85                  90                  95

Ser Thr Ala Gly Tyr Tyr His Gly Arg Tyr Val Leu Ser Ser Ile Tyr
            100                 105                 110

Ala Val Cys Ala Leu Ala Ala Leu Ile Cys Phe Val Ile Arg Leu Ala
```

```
                115                 120                 125
Lys Asn Cys Met Ser Trp Arg Tyr Ser Cys Thr Arg Tyr Thr Asn Phe
130                 135                 140

Leu Leu Asp Thr Lys Gly Arg Leu Tyr Arg Trp Arg Ser Pro Val Ile
145                 150                 155                 160

Ile Glu Lys Lys Gly Lys Val Glu Val Glu Gly Gln Leu Ile Asp Leu
165                 170                 175

Lys Arg Val Val Leu Asp Gly Ser Ala Ala Thr Pro Ile Thr Arg Val
180                 185                 190

Ser Ala Glu Gln Trp Gly Arg Pro
195                 200

<210> SEQ ID NO 9
<211> LENGTH: 200
<212> TYPE: PRT
<213> ORGANISM: Porcine reproductive and respiratory syndrome virus

<400> SEQUENCE: 9

Met Leu Gly Lys Cys Leu Thr Ala Gly Cys Cys Ser Gln Leu Pro Phe
1               5                   10                  15

Leu Trp Cys Ile Val Pro Phe Cys Phe Ala Ala Leu Val Asn Ala Ser
20                  25                  30

Ser Ser Ser Ser Ser Gln Leu Gln Ser Ile Tyr Asn Leu Thr Ile Cys
35                  40                  45

Glu Leu Asn Gly Thr Asp Trp Leu Asn Lys Asn Phe Asp Trp Ala Val
50                  55                  60

Glu Thr Phe Val Ile Phe Pro Val Leu Thr His Ile Val Ser Tyr Gly
65                  70                  75                  80

Ala Leu Thr Thr Ser His Phe Leu Asp Ala Val Gly Leu Ile Thr Val
85                  90                  95

Ser Thr Ala Gly Tyr Tyr His Gly Arg Ser Val Leu Ser Ser Val Tyr
100                 105                 110

Ala Val Cys Ala Leu Ala Ala Leu Ile Cys Phe Val Ile Arg Leu Thr
115                 120                 125

Lys Asn Cys Met Ser Trp Arg Tyr Ser Cys Thr Arg Tyr Thr Asn Phe
130                 135                 140

Leu Leu Asp Ser Lys Gly Lys Leu Tyr Arg Trp Arg Ser Pro Val Ile
145                 150                 155                 160

Ile Glu Lys Gly Gly Lys Val Glu Val Asp Gly His Leu Ile Asp Leu
165                 170                 175

Lys Arg Val Val Leu Asp Gly Ser Ala Ala Thr Pro Val Thr Lys Val
180                 185                 190

Ser Ala Glu Gln Trp Cys Arg Pro
195                 200

<210> SEQ ID NO 10
<211> LENGTH: 200
<212> TYPE: PRT
<213> ORGANISM: Porcine reproductive and respiratory syndrome virus

<400> SEQUENCE: 10

Met Leu Gly Lys Cys Leu Thr Ala Gly Cys Cys Ser Gln Leu Leu Phe
1               5                   10                  15

Leu Trp Cys Ile Val Pro Ser Trp Phe Val Ala Leu Val Ser Ala Ser
20                  25                  30

Asn Ser Ser Ser Ser His Leu Gln Leu Ile Tyr Asn Leu Thr Leu Cys
```

```
                35                  40                  45
Glu Leu Asn Gly Thr Asp Trp Leu Ala Asp Lys Phe Asp Trp Ala Val
 50                  55                  60

Glu Thr Phe Val Ile Phe Pro Val Leu Thr His Ile Val Ser Tyr Gly
 65                  70                  75                  80

Ala Leu Thr Thr Ser His Phe Leu Asp Thr Val Gly Leu Val Thr Val
                 85                  90                  95

Ser Thr Ala Gly Phe His His Gly Arg Tyr Val Leu Ser Ser Ile Tyr
            100                 105                 110

Ala Val Cys Ala Leu Ala Ala Leu Ile Cys Phe Val Ile Arg Leu Ala
        115                 120                 125

Lys Asn Cys Met Ser Trp Arg Tyr Ser Cys Thr Arg Tyr Thr Asn Phe
    130                 135                 140

Leu Leu Asp Thr Lys Gly Arg Leu Tyr Arg Trp Arg Ser Pro Val Ile
145                 150                 155                 160

Ile Glu Lys Gly Gly Lys Val Glu Val Glu Gly His Leu Ile Asp Leu
                165                 170                 175

Lys Arg Val Val Leu Asp Gly Ser Val Ala Thr Pro Ile Thr Arg Val
            180                 185                 190

Ser Ala Glu Gln Trp Gly Arg Pro
        195                 200

<210> SEQ ID NO 11
<211> LENGTH: 200
<212> TYPE: PRT
<213> ORGANISM: Porcine reproductive and respiratory syndrome virus

<400> SEQUENCE: 11

Met Leu Glu Lys Cys Leu Thr Ala Gly Cys Cys Ser Arg Leu Leu Ser
  1               5                  10                  15

Leu Trp Cys Ile Val Pro Phe Cys Phe Ala Val Leu Ala Asn Ala Ser
             20                  25                  30

Asn Asp Ser Ser Ser His Leu Gln Leu Ile Tyr Asn Leu Thr Leu Cys
        35                  40                  45

Glu Leu Asn Gly Thr Asp Trp Leu Ala Asn Lys Phe Asp Trp Ala Val
 50                  55                  60

Glu Ser Phe Val Ile Phe Pro Val Leu Thr His Ile Val Ser Tyr Gly
 65                  70                  75                  80

Ala Leu Thr Thr Ser His Phe Leu Asp Thr Val Ala Leu Val Thr Val
                 85                  90                  95

Ser Thr Ala Gly Phe Val His Gly Arg Tyr Val Leu Ser Ser Ile Tyr
            100                 105                 110

Ala Val Cys Ala Leu Ala Leu Thr Cys Phe Val Ile Arg Phe Ala
        115                 120                 125

Lys Asn Cys Met Ser Trp Arg Tyr Ala Cys Thr Arg Tyr Thr Asn Phe
    130                 135                 140

Leu Leu Asp Thr Lys Gly Arg Leu Tyr Arg Trp Arg Ser Pro Val Ile
145                 150                 155                 160

Ile Glu Lys Arg Gly Lys Val Glu Val Glu Gly His Leu Ile Asp Leu
                165                 170                 175

Lys Arg Val Val Leu Asp Gly Ser Val Ala Thr Pro Ile Thr Arg Val
            180                 185                 190

Ser Ala Glu Gln Trp Gly Arg Pro
        195                 200
```

<210> SEQ ID NO 12
<211> LENGTH: 200
<212> TYPE: PRT
<213> ORGANISM: Porcine reproductive and respiratory syndrome virus

<400> SEQUENCE: 12

```
Met Leu Gly Lys Cys Leu Thr Ala Gly Cys Cys Ser Gln Leu Leu Phe
1               5                   10                  15

Leu Trp Cys Ile Val Pro Ser Cys Phe Val Ala Leu Val Ser Ala Asn
            20                  25                  30

Gly Asn Ser Gly Ser Asn Leu Gln Leu Ile Tyr Asn Leu Thr Leu Cys
        35                  40                  45

Glu Leu Asn Gly Thr Asp Trp Leu Ala Asn Lys Phe Asp Trp Ala Val
    50                  55                  60

Glu Cys Phe Val Ile Phe Pro Val Leu Thr His Ile Val Ser Tyr Gly
65                  70                  75                  80

Ala Leu Thr Thr Ser His Phe Leu Asp Thr Val Gly Leu Val Thr Val
                85                  90                  95

Ser Thr Ala Gly Phe Val His Gly Arg Tyr Val Leu Ser Ser Met Tyr
            100                 105                 110

Ala Val Cys Ala Leu Ala Ala Leu Ile Cys Phe Val Ile Arg Leu Ala
        115                 120                 125

Lys Asn Cys Met Ser Trp Arg Tyr Ser Cys Thr Arg Tyr Thr Asn Phe
    130                 135                 140

Leu Leu Asp Thr Lys Gly Arg Leu Tyr Arg Trp Arg Ser Pro Val Ile
145                 150                 155                 160

Ile Glu Lys Arg Gly Lys Val Glu Val Glu Gly His Leu Ile Asp Leu
                165                 170                 175

Lys Arg Val Val Leu Asp Gly Ser Ala Ala Thr Pro Val Thr Arg Val
            180                 185                 190

Ser Ala Glu Gln Trp Ser Arg Pro
        195                 200
```

<210> SEQ ID NO 13
<211> LENGTH: 200
<212> TYPE: PRT
<213> ORGANISM: Porcine reproductive and respiratory syndrome virus

<400> SEQUENCE: 13

```
Met Leu Glu Lys Cys Leu Thr Ala Gly Cys Cys Ser Gln Leu Leu Ser
1               5                   10                  15

Leu Trp Cys Ile Val Pro Phe Cys Phe Ala Val Leu Ala Asn Ala Ser
            20                  25                  30

Asn Asp Ser Ser Ser His Leu Gln Leu Ile Tyr Asn Leu Thr Leu Cys
        35                  40                  45

Glu Leu Asn Gly Thr Asp Trp Leu Ala Asn Lys Phe Asp Trp Ala Val
    50                  55                  60

Glu Ser Phe Val Ile Phe Pro Val Leu Thr His Ile Val Ser Tyr Gly
65                  70                  75                  80

Ala Leu Thr Thr Ser His Phe Leu Asp Thr Val Ala Leu Val Thr Val
                85                  90                  95

Ser Thr Ala Gly Phe Val His Gly Arg Tyr Val Leu Ser Ser Ile Tyr
            100                 105                 110

Ala Val Cys Ala Leu Ala Ala Leu Thr Cys Phe Val Ile Arg Phe Ala
        115                 120                 125
```

```
Lys Asn Cys Met Ser Trp Arg Tyr Ala Cys Thr Arg Tyr Thr Asn Phe
130                 135                 140

Leu Leu Asp Thr Lys Gly Gly Leu Tyr Arg Trp Arg Ser Pro Val Ile
145                 150                 155                 160

Ile Glu Lys Arg Gly Lys Val Glu Val Glu Gly His Leu Ile Asp Leu
165                 170                 175

Lys Arg Val Val Leu Asp Gly Ser Val Ala Thr Pro Ile Thr Arg Val
180                 185                 190

Ser Ala Glu Gln Trp Gly Arg Pro
195                 200

<210> SEQ ID NO 14
<211> LENGTH: 200
<212> TYPE: PRT
<213> ORGANISM: Porcine reproductive and respiratory syndrome virus
      Consensus
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (58)..(58)
<223> OTHER INFORMATION: Xaa can be any naturally occurring amino acid
<220> FEATURE:
<221> NAME/KEY: misc_feature
<222> LOCATION: (94)..(94)
<223> OTHER INFORMATION: Xaa can be any naturally occurring amino acid
<220> FEATURE:
<221> NAME/KEY: misc_feature
<222> LOCATION: (164)..(164)
<223> OTHER INFORMATION: Xaa can be any naturally occurring amino acid

<400> SEQUENCE: 14

Met Leu Gly Lys Cys Leu Thr Ala Gly Cys Cys Ser Gln Leu Pro Phe
1               5                   10                  15

Leu Trp Cys Ile Val Pro Phe Cys Phe Ala Ala Leu Val Asn Ala Ser
20                  25                  30

Asn Xaa Ser Ser His Leu Gln Leu Ile Tyr Asn Leu Thr Ile Cys
35                  40                  45

Glu Leu Asn Gly Thr Asp Trp Leu Asn Xaa Lys Phe Asp Trp Ala Val
50                  55                  60

Glu Thr Phe Val Ile Phe Pro Val Leu Thr His Ile Val Ser Tyr Gly
65                  70                  75                  80

Ala Leu Thr Thr Ser His Phe Leu Asp Thr Val Gly Leu Xaa Thr Val
85                  90                  95

Ser Thr Ala Gly Tyr Tyr His Gly Arg Tyr Val Leu Ser Ser Ile Tyr
100                 105                 110

Ala Val Cys Ala Leu Ala Ala Leu Ile Cys Phe Val Ile Arg Leu Ala
115                 120                 125

Lys Asn Cys Met Ser Trp Arg Tyr Ser Cys Thr Arg Tyr Thr Asn Phe
130                 135                 140

Leu Leu Asp Thr Lys Gly Lys Leu Tyr Arg Trp Arg Ser Pro Val Ile
145                 150                 155                 160

Ile Glu Lys Xaa Gly Lys Val Glu Val Glu Gly His Leu Ile Asp Leu
165                 170                 175

Lys Arg Val Val Leu Asp Gly Ser Ala Ala Thr Pro Val Thr Arg Val
180                 185                 190

Ser Ala Glu Gln Trp Gly Arg Pro
195                 200
```

<210> SEQ ID NO 15
<211> LENGTH: 201
<212> TYPE: PRT
<213> ORGANISM: Porcine reproductive and respiratory syndrome virus

<400> SEQUENCE: 15

```
Met Arg Cys Ser His Lys Leu Gly Arg Phe Leu Thr Pro His Ser Cys
1               5                   10                  15

Phe Trp Trp Leu Phe Leu Leu Cys Thr Gly Leu Ser Trp Ser Phe Ala
            20                  25                  30

Asp Gly Asn Gly Asp Ser Ser Thr Tyr Gln Tyr Ile Tyr Asn Leu Thr
        35                  40                  45

Ile Cys Glu Leu Asn Gly Thr Asp Trp Leu Ser Ser His Phe Gly Trp
    50                  55                  60

Ala Val Glu Thr Phe Val Leu Tyr Pro Val Ala Thr His Ile Leu Ser
65                  70                  75                  80

Leu Gly Phe Leu Thr Thr Ser His Phe Phe Asp Ala Leu Gly Leu Gly
                85                  90                  95

Ala Val Ser Thr Ala Gly Phe Val Gly Gly Arg Tyr Val Leu Cys Ser
            100                 105                 110

Val Tyr Gly Ala Cys Ala Phe Ala Ala Phe Val Cys Phe Val Ile Arg
        115                 120                 125

Ala Ala Lys Asn Cys Met Ala Cys Arg Tyr Ala Arg Thr Arg Phe Thr
    130                 135                 140

Asn Phe Ile Val Asp Asp Arg Gly Arg Val His Arg Trp Lys Ser Pro
145                 150                 155                 160

Ile Val Val Glu Lys Leu Gly Lys Ala Glu Val Asp Gly Asn Leu Val
                165                 170                 175

Thr Ile Lys His Val Val Leu Glu Gly Val Lys Ala Gln Pro Leu Thr
            180                 185                 190

Arg Thr Ser Ala Glu Gln Trp Glu Ala
        195                 200
```

<210> SEQ ID NO 16
<211> LENGTH: 15414
<212> TYPE: DNA
<213> ORGANISM: Porcine reproductive and respiratory syndrome virus

<400> SEQUENCE: 16

```
atgacgtata ggtgttggct ctatgccatg acatttgtat tgtcaggagc tgcgaccatt      60
ggtacagccc aaaactagct gcacagaaaa cgcccttctg tgacagccct cttcagggga     120
gcttaggggt ctgtccctag caccttgctt ccggagttgc actgctttac ggtctctcca     180
acccttaac catgtctggg atacttgatc ggtgcacgtg cacccccaat gccagggtgt      240
ttatggcgga gggccaagtc tactgcacac gatgtctcag tgcacggtct ctccttcctc     300
tgaatctcca agttcctgag cttggagtgc tgggcctatt ttacaggccc gaagagccac     360
tccggtggac gttgccacgt gcattcccca ctgttgagtg ctcccccgcc ggggcctgct     420
ggctttctgc gatctttcca attgcacgaa tgaccagtgg aaacctgaac tttcaacaaa     480
gaatggtgcg gtcgcagct gagatttaca gagccggcca gctcacccct gcagtcttga     540
aggctctaca agtttatgaa cggggttgcc gctggtaccc tatagtcgga cctgtccctg     600
gagtggccgt ttttgccaac tcccctacatg tgagtgataa accttcccg ggagcaactc     660
atgtgctaac caacctgcca ctcccgcaga ggcctaagcc tgaagacttt tgccccttttg    720
```

-continued

```
agtgtgctat ggctgacgtc tatgatattg gtcatggcgc cgtcatgtat gtggccaaag    780
ggaaagtctc ctgggcccct cgtggcgggg atgaggcgaa atttgaaact gtccctaggg    840
agttgaagtt gatcgcgaac caactccaca tctccttccc gccccaccac gcagtggaca    900
tgtctaagtt tgtgttcata gcccctggga gtggtgtctc tatgcgggtc gagtgcccac    960
acggctgtct ccccgctaat actgtccctg aaggtaactg ctggtggcgc ttgtttgact   1020
cgctcccact ggacgttcag aacaaagaaa ttcgccgtgc caaccaattc ggctatcaaa   1080
ccaagcatgg tgtcgctggc aagtacctac aacggaggct gcaagctaat ggtctccgag   1140
cagtgactga tacagatgga cccattgtcg tacagtattt ctctgttagg gagagctgga   1200
tccgccactt cagactggcg gaagagccta gcctccctgg gtttgaagac ctcctcagaa   1260
taagggtaga gcccaatacg tcgccattga gtgacaaggg tggaaaaatc ttccggtttg   1320
gcagtcacaa atggtacggt gctggaaaga gagcaaggaa agcacgctct ggtatgacca   1380
ccacagtcgc tcaccgcgcc ttgcccgctc gtgaaatcca gcaagccaaa aagcacgagg   1440
atgccggcgc tgataaggct gtgcatctca ggcactattc tccgcctgcc gacgggaact   1500
gtggttggca ctgcatttcc gccatcgcca accgaatggt gaattccaaa tttgaaacta   1560
ctcttcccga gagggtgaga ccttcagatg actgggctac tgacgaggac cttgtgaaca   1620
ccatccaaat tctcaagctc cctgcggcct tggacaggaa cggtgcttgt gttggcgcca   1680
aatacgtgct taagctggaa ggcgagcatt ggactgtctc tgtgacccctt gggatgtccc   1740 cttcttttgct ccccccttgaa tgtgttcagg gctgttgtga gcataagagc ggacttggtc   1800
ccccagatgc ggtcgaagtt ttcggatttg accctgcctg ccttgaccga ctggctgagg   1860
taatgcactt gcctagcagt gtcatcccag ctgctctggc cgaaatgtcc ggcgacccca   1920
actgtccggc ttccccggtc actactgtgt ggactgtttc acaattcttt gcccgccaca   1980
gaggaggaga gcaccctgat caggtgcgct taggaaaaat catcagcctt tgtcaagttg   2040
ttgaggaatg ctgttgccat cagaataaaa ccaaccgggc caccccggaa gaggttgcgg   2100
caaggattga tcagtacctc catggtgcaa caagtcttga agaatgcttg attaggcttg   2160
agagggtttg cccgccgagc gctgcggaca ccttctttga ttggaatgtt gtgctccctg   2220
gggttggggc ttcaactcag acaaccaaac agctccatgt caaccagtgc cgcgctctgg   2280
ttcctgtcgt gactcaagag cctttggaca aagactcagt ccctctgacc gccttctcgc   2340
tgtccaattg ctactatcct gcacaaggtg acgaggttcg tcaccgtgag aggctaaact   2400
ccgtactctc taagctggag ggggttgttc gtgaggaata tgggctcacg ccaactgaac   2460
ctggcccgcg acccgcacta ccgaacgggc tcgtcgaact aaagaccag atggaggagg   2520 atctgctgaa actagtcaac gcccaggcaa cttcagaaat gatggcctgg gcagccgagc   2580
aggttgatct gaaagcttgg gtcaaaaact acccacggtg gacaccgcca cccccctccac   2640 caagagttca gcctcgaaaa acaaagtctg tcaagagctt gccagggaac aaacctgtcc   2700
ccgctccacg caggaaggtc agatctgatt gtggcagccc gattttgatg ggcgacaatg   2760
ttcctgacgg tcgggaagat ttgactgttg gtggccccct tgatctttcg acaccatccg   2820
agccgatgac acctctgagt gagcctgcac ttatgccccgc gttgcaatat atttctaggc   2880
cagtgacatc tttgagtgtg ctggccccag ttcctgcacc gcgtagaact gtgtcccgac   2940
cggtgacgcc cttgagtgag ccaattttttg tgtctgcacc gcgacacaaa tttcagcagg   3000
tggaagaagc gaatctggcg gcaacaacgc tgacgcacca ggacgaacct ctagatttgt   3060
ctgcatcctc acagactgaa tatgaggctt ctccccctaac accactgcag aacatgggta   3120
```

```
ttctggaggt ggggggggcaa gaagctgagg aagttctgag tgaaatctcg gatacactga    3180
atgacatcaa ccctgcacct gtgtcatcaa gcagctccct gtcaagtgtt aagatcacac    3240
gcccaaaaca ctctgctcaa gccatcattg actcgggcgg gccctgcagt gggcatctcc    3300
gaagggaaaa agaagcatgc ctcagcatca tgcgtgaggc ttgtgatgcg gctaagctta    3360
gtgaccctgc cacgcaggaa tggctttctc gcatgtggga tagggttgac atgctgactt    3420
ggcgcaacac gtctgcttac caggcgttcc gcatcttaga tggtaggttt gagtttctcc    3480
caaagatgat actcgagaca ccgccgccct acccgtgtgg gtttgtgatg ctgcctcaca    3540
cgcctgcacc ttccgtgggt gcagagagtg accttaccat tggttcagtc gccactgaag    3600
atgttccacg catcctcggg aaaatagaaa acgccggcga gatgcccaac caggggctct    3660
tgacatcctt cggggaagaa ccggtgtgcg accaacctgt caaggactcc tggatgtcgt    3720
cgcgggggtt tgacgagagc acaacggctc cgtccgctgg tacaggtggt gctgacttac    3780
ccaccgattt gccaccttca gatggtttgg atgcggacga gtgggggccg ttacggacgg    3840
taagaaagaa agctgaaagg ctcttcgacc aattgagccg tcaggttttt aacctcgtct    3900
cccatctccc tgttttcttc tcacacctct tcaaatctga cagtggttat tctccgggtg    3960 attgggggttt tgcagctttt actttatttt gcctctttt gtgttacagc tacccattct    4020
ttggttttgt tccctcttg ggtgttttt ctgggtcttc tcggcgtgtg cgcatggggg    4080
tttttggctg ttggttggct tttgctgttg gcctgttcaa gcctgtgtcc gacccagtcg    4140
gcactgcttg tgagtttgac tcgccagagt gtaggaacgt ccttcattct tttgagcttc    4200
tcaaaccttg ggaccctgtt cgcagccttg ttgtgggccc cgtcggtctc ggccttgcca    4260
ttcttggcag gttactgggc ggggcacgct acatctggca ttttttgctt aggcttggca    4320
ttgttgcaga ttgtatcttg gctggagctt atgtgctttc tcaaggtagg tgtaaaaagt    4380 gctgggggatc ttgtgtaaga actgctccta atgaaatcgc cttcaacgtg ttccctttta    4440
cgcgtgcgac caggtcgtca ctcatcgacc tgtgcgatcg gttttgtgcg ccaaaaggca    4500 tggacccccat tttcctcgct actgggtggc gcgggtgctg gaccggccga agtcccattg    4560
agcaaccctc tgaaaaaccc atcgcgttcg cccagttgga tgaaaagagg attacggcta    4620
gaactgtggt cgctcagcct tatgatccta accaagccgt aaagtgcttg cgggtgttac    4680
aggcgggtgg ggcgatagtg gccgaggcag tcccaaaagt ggtcaaggtt tccgctattc    4740
cattccgagc tcccttttt cccaccggag tgaaggttga tcctgagtgc aggatcgtgg    4800
tcgaccccga cacttttact acagctctcc ggtctggtta ctccaccaca aacctcgtcc    4860
ttggtgtggg gactttgcc caactgaatg gattaaaaat caggcaaatt tccaagccct    4920
cgggaggagg cccgcacctc attgctgccc tgcatgttgc ttgctcgatg gcgttgcaca    4980
tgcttgctgg agtttatgta actgcagtgg ggtcttgcgg taccggcacc aacgatccgt    5040
ggtgcactaa cccattcgcc gtccctggct acggacctgg ctccctctgc acgtccagat    5100
tgtgcatctc ccaacatggc cttaccctgc ccttgacagc acttgtggca ggattcggtc    5160
ttcaggaaat tgccctagtc gttttgattt tcgtttccat cggaggcatg gctcataggt    5220
tgagttgtaa ggctgatatg ctgtgcgtct tacttgcaat cgccagctat gtttgggtac    5280
cccttacctg gttgctctgt gtgtttcctt gctggttgcg ctggttctct ttgcaccctc    5340
tcaccattct atggtggtg tttttcttga tgtctgtaaa tatgccttcg ggaatcttaa    5400
ccgtggtgtt attggttgct ctttggcttc taggccgtta tactaatgtt gttggtcttg    5460
```

-continued

```
ttaccccta tgatattcat cattacacca atggcccccg cggtgttgcc gccttggcta    5520
ccgcaccaga tgggacttac ttggccgctg tccgccgcgc tgcgttgact ggccgcaccg    5580
tgctgtttac cccgtctcag cttgggtccc ttcttgaggg cgctttcaga actcgaaagc    5640
cctcactgaa caccgtcaat gtggtcgggt cctccatggg ctctggcgga gtgttcacta    5700
tcgatgggaa aattaagtgc gtgactgccg cacatgtcct tacgggtaat tcagctaggg    5760
tttccggggt cggcttcaat caaatgcttg actttgatgt aaaagggggac ttcgccatag    5820
ctgattgccc gaattggcaa ggggctgctc ctaagaccca attctgcgag gatggatgga    5880
ctggccgcgc ctattggctg acatcctctg gcgtcgaacc cggtgtcatt gggaatggat    5940
tcgccttctg cttcaccgcg tgcggcgatt ccgggtcccc agtgatcacc gaagccggtg    6000
agcttgtcgg cgttcacaca ggatcaaaca aacaaggagg aggcattgtt acgcgccct    6060
ctggccagtt ttgcaatgtg gcacccatca agctgagcga attaagtgag ttctttgctg    6120
gacctaaggt cccgctcggt gatgtgaagg ttggcagcca cataattaaa gacatatgcg    6180
aggtaccttc agatctttgc gccttgcttg ctgccaaacc cgaactggaa ggaggcctct    6240
ccaccgtcca acttctgtgt gtgttttttcc tcctgtggag aatgatggga catgcctgga    6300
cgcccttggt tgctgttggg ttttttatct tgaatgaggt tctcccagct gtactggtcc    6360
ggagtgtttt ctcctttgga atgtttgtgc tatcttggct cacaccatgg tctgcgcaag    6420
ttctgatgat caggcttcta acagcagctc ttaacaggaa cagattgtca ctcgccttt    6480
acagccttgg tgcagcgacc ggttttgtcg cagatctggc ggcaactcaa gggcacccgt    6540
tgcaggcagt aatgaattta agtacctatg ccttcctgcc tcggataatg gtcgtgacct    6600
caccagtccc agtgattgcg tgtggtgttg tgcacctcct tgccataatt ttgtacttgt    6660
ttaagtaccg ctgcctgcac aatgtccttg ttggcgatgg tgcgttctct gcggctttct    6720
tcttgcgata ctttgccgag gggaaattga gggaagggggt gtcgcaatcc tgcgggatga    6780
atcatgagtc gctgactggt gccctcgcta tgagacttaa tgacgaggac ttggattttc    6840
ttacgaaatg gactgatttt aagtgttttg tttctgcatc caacatgagg aatgcggcgg    6900
gccagttcat cgaggctgcc tatgctaaag cacttagaat tgaacttgcc cagttggtgc    6960
aggttgataa ggttcgaggt actttggcca aacttgaagc ttttgctgat accgtggcac    7020
cccaactctc gccggtgac attgttgttg ctcttggcca tacgcctgtt ggcggtatct    7080
tcgacctaaa ggttggtagc accaagcata ccctccaagc cattgagacc agagttcttg    7140
ccgggtccaa aatgaccgtg gcgcgtgtcg ttgatccaac ccccacaccc ccacccgcac    7200
ccgtgcctat cccccttcca ccgaaagttc tggagaatgg tccccaacgcc tggggggatg    7260
aggatcgttt gaataagaag aagaggcgca ggatggaagc cgtcggcatc tttgttatgg    7320
gtggaaagaa atatcagaaa ttttgggaca agaactccgg tgatgtgttt tatgaggagg    7380
tccatgataa cacagacgcg tgggagtgcc tcagagttga caaccctgcc gactttgacc    7440
ctgagaaggg aactctgtgc gggcatacta ccattgaaga taagacttac agtgtctacg    7500
cctccccatc tggcaagaaa ttcctggtcc ccgtctaccc agagagcaaa aaaaccaat    7560
gggaagctgc gaagctttcc gtggaacagg cccttggcat gatgaatgtc gacggtgaac    7620
tgacagccaa agaagtggag aaactgaaaa gaataattga caaactccag ggcctgacta    7680
aggagcagtg tttaaactgc tagccgccag cggcttgacc cgctgtggtc gcggcggctt    7740
ggttgttact gagacagcgg taaaaatagt caaatttcac aaccggacct tcaccctagg    7800
acctgtgaat ttaaaagtgg ccagtgaggt tgagctaaaa gacgcggtcg agcataacca    7860
```

-continued

```
acacccggtt gcaagaccgg ttgatggtgg tgttgtgctc ctgcgctccg cagttccttc   7920
gcttatagac gtcttaatct ccggcgctga tgcatctccc aagttactcg cccgccacgg   7980
gccgggaaac actgggatcg atggcacgct ttgggatttt gaggccgagg ccactaaaga   8040
ggaaattgca ctcagtgcgc aaataataca ggcttgtgac attaggcgcg gcgacgcacc   8100
tgaaattggt cttccttata agctgtaccc tgtcaggggc aaccctgagc gggtaaaagg   8160
agttttacag aatacaaggt ttggagacat accttataaa accccagtg acactggaag    8220
cccagtgcac gcggctgcct gcctcacgcc caatgccact ccggtgactg atgggcgctc   8280
cgtcttggcc acgactatgc cctccggttt tgagttgtat gtaccgacca ttccagcgtc   8340
tgtccttgat tatcttgatt ctaggcctga ctgccccaaa cagttgacag agcacggctg   8400
tgaggacgcc gcattaagag acctctccaa gtatgacttg tccacccaag ctttgttttt   8460
acctggagtt cttcgccttg tgcgtaagta cctgtttgct catgtgggta agtgcccgcc   8520
cgttcatcgg ccttccactt accctgccaa gaattctatg gctggaataa atgggaacag   8580
gtttccaacc aaggacatcc agagcgtccc tgaaatcgac gttctgtgcg cacaggccgt   8640
gcgggaaaac tggcaaactg ttaccccttg taccctcaag aaacagtatt gtgggaagaa   8700
gaagactagg acaatactcg gcaccaataa cttcattgca ctggcccacc gggcagcgtt   8760
gagtggtgtc acccagggct tcatgaaaaa ggcgtttaac tcgcccattg ccctcggtaa   8820
aaacaaattt aaagagcttc agactccggt cttaggcagg tgccttgaag ctgatcttgc   8880
atcctgcgat cgctccacac ctgcaattgt ccgctggttt ccgccaatc ttctttatga    8940
acttgcctgt gctgaagagc acctgccgtc gtacgtgttg aactgctgcc acgacctact   9000
ggtcacgcag tccggcgcag taactaagag aggtggcctg tcgtctggcg acccgatcac   9060
ttctgtgtcc aacaccattt acagcttggt gatatatgca caacacatgg tgctcagtta   9120
ctttaaaagt ggtcaccctc atggccttct gtttctacaa gaccagctga gtttgaggga   9180
catgctcaag gttcaacccc tgatcgtcta ttcggacgac ctcgtactgt atgccgagtc   9240
tcccaccatg ccaaactacc actggtgggt tgaacatctg aacctgatgc tgggttttca   9300
gacggaccca aagaagacag ccataacaga ctcgccatca tttctaggct gtaggataat   9360
aaatggacgc cagctcgtcc ctaaccgtga caggattctc gcggccctcg cctaccatat   9420
gaaggcaagc aatgtctctg aatactacgc ctcggcggct gcgatactca tggacagctg   9480
tgcttgttta gagtatgatc ccgaatggtt tgaagagctt gtagttggga tagcgcagtg   9540
tgcccgcaag gacggctaca gttttcccgg cccgccgttc ttcttgtcca tgtgggaaaa   9600
actcagatcc aatcatgagg ggaagaagtc cagaatgtgc gggtactgcg gggccccggc   9660
tccgtacgcc actgcctgtg gcctcgacgt ctgtatttac cacacccact ccaccagca    9720
ttgtccagtc atcatctggt gtggccaccc ggctggttct ggttcttgta gtgagtgcaa   9780
accccccta gggaaaggca caagccctct agatgaggtg ttagaacaag tcccgtataa    9840
gcctccacgg actgtaatca tgcatgtgga gcagggctctc accctcttg acccaggcag   9900
ataccagact cgccgcggat tagtctccgt taggcgtggc attagaggaa atgaggttga   9960
tctaccagac ggtgattatg ctagcaccgc cctactccct acttgtaaag agattaacat   10020
ggtcgctgtc gcctctaatg tgttgcgcag caggttcatc atcggcccgc ctggtgctgg   10080
gaaaacatac tggctccttc aacaggtcca ggatggtgat gtcatttaca cgccaactca   10140
ccagaccatg ctcgatatga ttagggcttt ggggacgtgc cggttcaacg tcccagcagg   10200
```

```
tacgacgctg caattccctg cccccteccg taccggccct tgggttcgca tcctagccgg   10260
cggttggtgt cctggcaaga attccttcct ggatgaagca gcgtattgta atcaccttga   10320
tgtcttgagg cttcttagca aaactaccct cacctgtctg ggagatttca aacaactcca   10380
cccagtgggt tttgattctc attgctatgt ttttgacatc atgcctcaga ctcaactgaa   10440
gaccatctgg agatttggac agaatatctg tgatgccatt cagccagatt acagggacaa   10500
acttgtatcc atggtcaaca aacccgtgt aacctacgtg gaaaaacctg tcaagtatgg   10560
gcaagtcctc accccttacc acagggaccg agaggacggc gccatcacaa ttgactccag   10620
tcaaggcgcc acatttgatg tggttacact gcatttgccc actaaagatt cactcaacag   10680
gcaaagagcc cttgttgcta ttaccagggc aagacatgct atctttgtgt atgacccaca   10740
caggcaactg cagagcatgt ttgatcttcc tgcgaaaggc acacccgtca acctcgctgt   10800
gcaccgtgac gagcagctga tcgtgctaga tagaaataac aaagaatgca cggttgctca   10860
ggctctaggc aatggggata aattcagggc cacagacaag cgcgttgtag attctctccg   10920
cgccatttgt gcagatctgg aagggtcgag ctccccgctc cccaaggtcg cacacaactt   10980
gggattttat ttctcgcctg atttgacaca gtttgctaaa ctcccggtag aacttgcacc   11040
ccactggccc gtggtgacaa cccagaacaa tgaaaagtgg ccagaccggt tggttgctag   11100
ccttcgcccc gtccataagt atagccgcgc gtgcatcggt gccggctaca tggtgggccc   11160
ctcagtgttt ctgggcaccc ctggggttgt gtcatactat ctcacaaaat ttgtcagggg   11220
cgaggctcaa atgcttccgg agacagtctt cagcaccggc cgaattgagg tagattgccg   11280
tgagtatctt gatgaccggg agcgagaaat tgctgagtcc ctcccccatg ctttcattgg   11340
cgacgtcaaa ggcactaccg ttggaggatg tcaccatgtc acctccaaat accttccgcg   11400
cttccttccc aaggaatcag tcgcggtagt cggggtttca agccccggga aagccgcaaa   11460
agcagtttgc acattaacag atgtgtatct cccagatctc gaagcttacc tccacccaga   11520
gacccagtcc aagtgctgga aaatgatgtt ggacttcaag gaagttcgac tgatggtctg   11580
gaaggacaag acggcctatt ttcaacttga aggccgccat ttcacctggt accagcttgc   11640
aagctatgcc tcgtacatcc gagttcctgt taactctacg gtgtatttgg acccctgcat   11700
gggccctgcc ctttgcaaca gaagagttgt cgggtccact cattggggag ctgacctcgc   11760
agtcacccct tatgattacg gtgccaaaat catcctgtct agtgcatacc atggtgaaat   11820 gcccccctggg tacaaaatcc tggcgtgcgc ggagttctcg cttgacgatc cagtgaggta   11880
caaacacacc tggggtttg aatcggatac agcgtatctg tacgagttca ccggaaacgg   11940
tgaggactgg gaggattaca atgatgcgtt tcgtgcgcgc cagaaaggga aaatttataa   12000
ggccactgcc accagcatga ggtttcattt tcccccgggc cctgtcattg aaccaacttt   12060
aggcctgaat tgaaatgaaa tggggtccat gcaaagcctc tttgacaaaa ttggccaact   12120
ttttgtggat gctttcacgg aattttttggt gtccattgtt gatatcatca tattttttggc   12180 cattttgttt ggctttacca tcgctggctg gctggtggtc ttctgcatcc gattggtttg   12240
ctccgcggta ctccgtgcgc gccctaccat tcacctgag caattacaga agatcctatg   12300
aggcctttct ttctcagtgc caggtggata ttcccacctg ggaactaga catcccctgg   12360 ggatgctttg gcaccataag gtgtcaaccc tgattgatga atggtgtcg cgtcggatgt   12420 accgcaccat ggaaaaagca ggacaggctg cctggaaaca ggtggtgagc gaggccacgc   12480
tgtctcgcat tagtggtttg gatgtggtgg ctcattttca gcatcttgcc gccattgaag   12540
ccgagacctg taaatatttg gcctctcggc tgcccatgct acacaatctg cgcatgacag   12600
```

```
ggtcaaatgt aaccatagtg tataatagta ctttgaatca ggtgtttgct attttttccaa    12660 cccctggatc ccggccaaag cttcatgatt ttcagcaatg ctaatagct gtgcactcct     12720 ccatattttc ctccgttgcg gcttcttgta ctcttttgt tgtgctgtgg ttgcggattc      12780
caatactacg tactgttttt ggtttccgct ggttaggggc aattttttcct tcgaactcac    12840 ggtgaattac acggtgtgtc cgccttgcct cacccggcaa gcagccgctg aggtctacga    12900
accaggcagg tctctttggt gcaggatagg gcatgaccga tgtagtgagg acgaccatga    12960
cgatctaggg ttcatggttc cgcctggcct ctccagcgaa ggccacttga ccagtgttta    13020
cgcctggttg gcgttcctgt ccttcagcta cacggcccag ttccatcccg agatatttgg    13080
gatagggaat gtgagtcaag tttatgttga catcaagcac caattcatct gcgccgttca    13140
cgacggggag aacgccacct tgcctcgtca tgacaatatt tcagccgtat ttcagaccta    13200
ctaccaacat caagtcgacg gcggcaattg gtttcaccta gaatggctgc gccccttctt    13260
ttcctcttgg ttggttttaa atgtttcttg gtttctcagg cgttcgcctg caagccatgt    13320
ttcagttcaa gtcttccgga catcaaaacc aacactaccg cagcatcagg ctttgttgtc    13380
ctccaggaca tcagctgcct taggcatggc gactcgtcct ctcagacgat tcgcaaaagc    13440
tctcagtgcc gcgcggcgat agggacgccc gtgtacatca ctgtcacagc caatgtcaca    13500
gatgagaatt atttacattc ttctgatctc cttatgcttt cttcttgcct tttctatgct    13560
tctgagatga gtgaaaaggg attcaaggtg atatttggca atgtgtcagg catcgtggct    13620
gtgtgtgtca actttaccag ctacgtccaa catgtcaagg agtttacccca acgctccttg    13680 gtggtcgatc atgtgcggct gctccatttc atgacacctg agaccatgag gtgggcaacc    13740
gttttagcct gttttttttgc catcttactg gcaatttgaa tgttcaagta tgttggggag    13800
atgcttgacc gcgggctgtt gctcgcgatt gctttctttg tggtgtatcg tgccattttg    13860
ttttgctgcg ctcgtcaacg ccaacagcaa cagcagctct catcttcagt tgatttacaa    13920
cttgacgcta tgtgagctga atggcacaga ttggctgaaa gacaaatttg attgggcagt    13980
ggagactttt gtcatctttc ccgtgttgac tcacattgtc tcatatggtg cactcaccac    14040
tagccatttc cttgacacag tcggtctggt tactgtgtct accgccgggt tctaccacgg    14100
gcggtatgtt ctgagtagca tctacgcggt ctgcgctctg gccgcattga tttgcttcgt    14160
cattaggctt gcgaagaact gcatgtcctg gcgctactct tgtaccagat atactaactt    14220
ccttctggac actaagggca gactctatcg ctggcggtcg cccgttatca tagagaaagg    14280
gggtaaggtt gaggtcgaag gtcacctgat cgacctcaaa agagttgtgc ttgatggttc    14340
cgtggcaacc cctttaacca gagtttcagc ggaacaatgg ggtcgtcttt agacgacttt    14400
tgctatgata gcacggctcc acaaaaggtg cttttggcgt tttccattac ctacacgcca    14460
gtgatgatat atgctctaaa ggtaagtcgc ggccgacttt tagggcttct gcacctttg     14520 atctttctga attgtactttt taccttcggg tacatgacat tcgtgcactt taatagcaca    14580
aataaggtcg cgctcactat gggagcagta gttgcacttc tttggggggt gtactcagcc    14640
atagaaacct ggaagttcat cacctccaga tgccgtttgt gcttgctagg ccgcaagtac    14700
attctggccc ccgcccacca cgtcgaaagt gccgcgggct ttcatccgat cgcggcaaat    14760
gataaccacg catttgtcgt ccggcgtccc ggctccacta cggttaacgg cacattggtg    14820
cccgggttga aaagcctcgt gttgggtggc agaaaagctg ttaaacaggg agtggtaaac    14880
cttgtcaaat atgccaaata acaacggcaa gcagcaaaag aaaaagaggg ggaatggcca    14940
```

```
gccagtcaat cagctgtgcc agatgctggg taagatcatc gcccagcaaa accagtccag   15000
aggcaaggga ccggggaaga aaattaagaa taaaaacccg agaagcccc  attttcctct   15060 agcgactgaa gatgacgtca ggcatcactt caccccctagt gagcggcaat tgtgtctgtc   15120
gtcgatccag actgccttta accagggcgc tggaacctgt accctatcag attcaggtag   15180
gataagttac actgtggagt ttagtttgcc gacgcatcat actgtgcgcc tgatccgcgt   15240
cacagcgcca tcatcagcgt aatgggctgg cattccttaa gcacctcagt gttagaattg   15300
gaagaatgtg tggtgaatgg cactgattgg cactgtgcct ctaagtcacc tattcaatta   15360
gggcgaccgt gtgggggtta agtttaattg gcgagaacca tgcggccgaa atta          15414

<210> SEQ ID NO 17
<211> LENGTH: 15451
<212> TYPE: DNA
<213> ORGANISM: Porcine reproductive and respiratory syndrome virus

<400> SEQUENCE: 17
tatgacgtat aggtgttggc tctatgcctt ggcatttgta ttgtcaggag ctgtgaccat     60
tggcacagcc caaaacttgc tgcacagaaa caccccttctg tgatagcctc cttcagggga    120
gcttagggtt tgtccctagc accttgcttc cggagttgca ctgctttacg gtctctccac    180
ccctttaacc atgtctggga tacttgatcg gtgcacgtgt accccccaatg ccagggtgtt    240 tatggcggag ggccaagtat actgcacacg atgcctcagt gcacggtctc tccttcccct    300
gaacctccaa gtttctgagc tcggggtgct aggcctattc tacaggcccg aagagccact    360
ccggtggacg ttgccacgtg cattccccac tgttgagtgc tcccccgccg gggcctgctg    420
gctttctgca atctttccaa tcgcacgaat gaccagtgga aacctgaact tccaacaaag    480
aatggtacgg gtcgcagctg agctttacag agccggccag ctcacccctg cagtcttgaa    540
ggctctacaa gtttatgaac ggggttgccg ctggtacccc attgttggac ctgtccctgg    600
agtggccgtt ttcgccaatt ccctacatgt gagtgataaa cctttcccgg gagcaactca    660
cgtgttgacc aacctgccgc tcccgcagag acccaagcct gaagactttt gccccttgtga    720 gtgtgctatg gctactgtct atgacattgg tcatgacgcc gtcatgtatg tggccgaaag    780
gaaagtctcc tgggcccctc gtggcgggga tgaagtgaaa tttgaagctg tccccgggga    840
gttgaagttg attgcgaacc ggctccgcac ctccttcccg ccccaccaca cagtggacat    900
gtctaagttc gccttcacag cccctgggtg tggtgttct atgcgggtcg aacgccaaca    960
cggctgcctt cccgctgaca ctgtccctga aggcaactgc tggtggagct gtttgactt   1020 gcttccactg gaagttcaga caaagaaat tcgccatgct aaccaatttg gctatcagac   1080
caagcatggt gtctctggca gtacctaca gcggaggctg caagttaatg gtctccgagc   1140
agtaactgac ctaaacggac ctatcgtcgt acagtacttc tccgttaagg agagttggat   1200
ccgccatttg aaactggcgg gagaacccag ctactctggg tttgaggacc tcctcagaat   1260
aagggttgag cctaacacgt cgccattggc tgacaaggaa gaaaaatttt ccggttttgg   1320
cagtcacaag tggtacggcg ctggaaagag agcaagaaaa gcacgctctt gtgcgactgc   1380
tacagtcgct ggccgcgctt tgtccgttcg tgaaacccgg caggccaagg agcacgaggt   1440
tgccggcgcc aacaaggctg agcacctcaa acactactcc ccgcctgccg aagggaattg   1500
tggttggcac tgcatttccg ccatcgccaa ccggatggtg aattccaaat ttgaaaccac   1560
ccttcccgaa agagtgagac ctccagatga ctgggctact gacaggatc ttgtgaatgc   1620 catccaaatc ctcagactcc ctgcggcctt agacaggaac ggtgcttgta ctagcgccaa   1680
```

```
gtacgtactt aagctggaag gtgagcattg gactgtcact gtgacccctg ggatgtcccc    1740
ttctttgctc cctcttgaat gtgttcaggg ctgttgtggg cacaagggcg gtcttggttc    1800
cccagatgca gtcgaggtct ccggatttga ccctgcctgc cttgaccggc tggctgaggt    1860
gatgcacctg cctagcagtg ctatcccagc cgctctggcc gaaatgtctg gcgattccga    1920
tcgttcggct ctccggtca ccaccgtgtg gactgtttcg cagttctttg cccgtcacag     1980
cggagggaat caccctgacc aagtgcgctt agggaaaatt atcagccttt gtcaggtgat    2040
tgaggactgc tgctgttccc agaacaaaac caaccgggtc accccggagg aggtcgcagc    2100
aaagattgac ctgtacctcc gtggtgcaac aaatcttgaa gaatgcttgg ccaggcttga    2160
gaaagcgcgc ccgccacgcg taatcgacac ctcctttgat tgggatgttg tgctccctgg    2220
ggttgaggcg gcaacccaga cgatcaagct gccccaggtc aaccagtgtc gtgctctggt    2280
ccctgttgtg actcaaaagt ccttggacaa caactcggtc cccctgaccg ccttttcact    2340
ggctaactac tactaccgtg cgcaaggtga cgaagttcgt caccgtgaaa gactaaccgc    2400
cgtgctctcc aagttggaaa aggttgttcg agaagaatat gggctcatgc caaccgagcc    2460
tggtccacgg cccacactgc cacgcgggct cgacgaactc aaagaccaga tggaggagga    2520
cttgctgaaa ctggctaacg cccagacgac ttcggacatg atggcctggg cagtcgagca    2580
ggttgaccta aaaacttggg tcaagaacta cccgcggtgg acaccaccac cccctccgcc    2640
aaaagttcag cctcgaaaaa cgaagcctgt caagagcttg ccggagagaa agcctgtccc    2700
cgccccgcgc aggaaggttg ggtccgattg tggcagcccg gtttcattag gcggcgatgt    2760
ccctaacagt tgggaagatt tggctgttag tagccccttt gatctcccga ccccacctga    2820
gccggcaaca ccttcaagtg agctggtgat tgtgtcctca ccgcaatgca tcttcaggcc    2880
ggcgacaccc ttgagtgagc cggctccaat tcccgcacct cgcggaactg tgtctcgacc    2940
ggtgacaccc ttgagtgagc cgatccctgt gcccgcaccg cggcgtaagt ttcagcaggt    3000
gaaaagattg agttcggcgg cggcaatccc accgtaccag gacgagcccc tggatttgtc    3060
tgcttcctca cagactgaat atgaggcctc tcccccagca ccgccgcaga gcggggcgt     3120 tctgggagta gaggggcatg aagctgagga acccctgagt gaaatctcgg acatgtcggg    3180
taacattaaa cctgcgtccg tgtcatcaag cagctccttg tccagcgtga gaatcacacg    3240
cccaaaatac tcagctcaag ccatcatcga ctcgggcggg ccctgcagtg gcatctcca    3300 agaggtaaag gaaacatgcc ttagtgtcat gcgcgaggca tgtgatgcga ctaagcttga    3360
tgaccctgct acgcaggaat ggctttctcg catgtgggat cgggtggaca tgctgacttg    3420
gcgcaacacg tctgttttacc aggcgatttg caccttagat ggcaggttaa agttcctccc    3480
aaaaatgata ctcgagacac cgccgcccta tccgtgtgag tttgtgatga tgcctcacac    3540
gcctgcacct tccgtaggtg cggagagcga ccttaccatt ggctcagttg ctactgaaga    3600
tgttccacgc atcctcgaga aaatagaaaa tgtcggcgag atggccaacc agggaccctt    3660
ggccttctcc gaggataaac cggtagatga ccaacttgtc aacgaccccc ggatatcgtc    3720
gcggaggcct gacgagagca catcagctcc gtccgcaggc acaggtggcg ccggctcttt    3780
taccgatttg ccgccttcag atggcgcgga tgcggacggg gggggggccgt ttcggacggt    3840 aaaaagaaaa gctgaaaggc tctttgacca actgagccgt caggtttttg acctcgtctc    3900
ccatctccct gtttttcttct cacgccttttt ctaccctggc ggtggttatt ctccgggtga    3960 ttgggggttttt gcagctttta ctctattgtg cctcttttta tgttacagtt acccagcctt    4020
```

-continued

```
tggtattgct cccctcttgg gtgtgttttc tgggtcttct cggcgcgttc aatgggggt    4080 ttttggctgc tggttggctt ttgctgttgg tctgttcaag cctgtgtccg acccagtcgg    4140
cgctgcttgt gagtttgact cgccagagtg tagaaacatc cttcattctt ttgagcttct    4200
caaaccttgg gaccctgttc gcagccttgt tgtgggcccc gtcggtctcg gtcttgccat    4260
tcttggcagg ttactgggcg gggcacgctg catctggcac tttttgctta ggcttggcat    4320
tgttgcagac tgtatcttgg ctggagctta cgtgctttct caaggtaggt gtaaaaagtg    4380
ctggggatct tgtataagaa ctgctcctaa tgaggtcgct tttaacgtgt ttcctttcac    4440
acgtgcgacc aggtcgtcac ttatcgacct gtgcgatcgg ttttgtgcgc caaaggaat     4500 ggacccccatt tttctcgcca ctgggtggcg cgggtgctgg gccggccgaa gccccattga    4560
gcaaccctct gaaaaaccca tcgcgtttgc ccaattggat gaaaagaaga ttacggctag    4620
gactgtggtc gcccagcctt atgaccccaa ccaagccgta aagtgcttgc gggtattgca    4680
ggcgggtggg gcgatggtgg ctaaggcggt cccaaaagtg gtcaaggttt ccgctgttcc    4740
attccgagcc cccttctttc ccactggagt gaaagttgac cctgattgca gggtcgtggt    4800
tgaccctgac actttcactg cagctctccg gtctggctac tccaccacaa acctcgtcct    4860
tggtgtaggg gactttgccc agctgaatgg attaaaaatc aggcaaattt ccaagccttc    4920 aggggggggaggc ccacatctca tggctgccct gcatgttgcc tgctcgatgg ctctgcacat    4980
gcttgctggg atttatgtga ctgcggtggg ttcttgcggc accggcacca acgacccgtg    5040
gtgcgctaac ccgtttgccg tccctggcta cggacctggc tctctctgca cgtccagatt    5100
gtgcatttcc caacacggcc ttaccctgcc cttgacagca cttgtggcgg gattcggtat    5160
tcaagaaatt gccttggtcg ttttgatttt tgtttccatc ggaggcatgg ctcataggtt    5220
gagctgtaag gctgacatgc tgtgtgtttt gcttgcaatt gccagctatg tttgggtacc    5280
tcttacctgg ttgcttgtg tgtttccttg ctggttgcgc tgttttttctt tgcacccct     5340 caccatccta tggttggtgt ttttcttgat ttctgtgaat atgccttcag gaatcttggc    5400
catggtgttg ttggttttctc tttggcttct tggtcgttat actaatgttg ctggccttgt    5460 cacccccta gacattcatc attacaccag tggccccgc ggtgttgccg ccttggctat    5520
cgcaccagat gggacctact tggccgctgt ccgccgcgct cgttgactg gccgcaccat    5580 gctgttacc ccgtcccagc ttgggtctct acttgagggt gctttcagaa ctcgaaagcc    5640
ctcactgaac accgtcaatg tgatcgggtc ctccatgggc tctggcgggg tgtttaccat    5700
cgacgggaaa gtcaagtgcg taactgccgc acatgtcctt acgggcaatt cagctcgggt    5760
ttccggggtc ggcttcaatc aaatgctgga ctttgacgta aagggagatt tcgctatagc    5820
tgattgcccg aattggcaag gggctgcccc caagacccaa ttctgcacgg atggatggac    5880
tggccgtgcc tattggctaa catcctctgg cgtcgaaccc ggcgtcattg gaaaaggatt    5940
cgccttctgc ttcaccgcat gtggcgattc cgggtcccca gtgatcaccg aggccggtga    6000
gcttgtcggc gttcacacgg atcgaataa acaaggggg ggcattgtta cgcgcccctc    6060
aggccagttt tgtaatgtgg cacccatcaa gctaagcgaa ttaagtgaat tctttgctgg    6120
gcctaaggtc ccgctcggtg atgtgaaggt cggcagccac ataattaaag acataagcga    6180
ggtgccttca gatctttgtg ccttgcttgc tgccaaacct gaactggaag gaggcctctc    6240
caccgtccaa cttctttgtg tgttttttct cctgtggaga atgatgggac atgcctggac    6300
gcccttggtt gctgtgagtt tctttatttt gaatgaggtt ctcccagccg tcctggtccg    6360 gagtgtttc tcctttggaa tgtttgtgct atcctggctc acgccatggt ctgcgcaagt    6420
```

```
tctgatgatc aggcttctga cagcagctct taacaggaac agatggtcac ttgcctttttt    6480
cagcctcggt gcagtgaccg gttttgtcgc agatcttgcg gccactcagg ggcatccgtt    6540
gcaggcagtg atgaatttga gcacctatgc attcctgcct cggatgatgg ttgtgacctc    6600
accagtccca gtgatcacgt gtggtgtcgt gcacctactt gccatcattt tgtacttgtt    6660
taagtaccgt ggcccgcacc atatccttgt tggcgatgga gtgttctctg cggctttctt    6720
cttgagatac tttgccgagg gaaagttgag ggaagggggtg tcgcaatcct gcggaatgaa   6780
tcatgagtct ctgactggtg ccctcgctat gagactcaat gacgaggact tggatttcct    6840
tatgaaatgg actaattta agtgctttgt ttctgcgtcc aacatgagga atgcagcggg     6900
tcaatttatc gaggctgcct atgctaaagc acttagagta gaactggccc agttggtgca    6960
ggttgacaaa gttcgaggta ctttggccaa acttgaagct tttgctgata ccgtggcacc    7020
tcaactctcg cccggtgaca ttgttgtcgc tctcggccac acgcctgttg gcagtatctt    7080
cgacctaaag gttggtagca ccaagcatac cctccaagcc attgagacca gagtccttgc    7140
tgggtccaaa atgaccgtgg cgcgcgtcgt cgacccgacc cccacgcccc cacccgcacc    7200
cgtgcccatc cccctcccac cgaaagttct ggagaatggc cccaacgctt gggggggatga   7260
ggaccgtttg aataagaaga agaggcgcag gatggaagcc ctcggcatct atgttatggg    7320
cgggaaaaag taccagaaat tttgggacaa gaattccggt gatgtgtttt atgaggaggt    7380
ccataataac acagatgagt gggagtgtct cagagttggc gaccctgccg actttgaccc    7440
tgagaaggga actctgtgtg gacatgtcac cattgaaaac aaggcttacc atgtttacac    7500
ctccccatct ggtaagaagt tcttggtccc cgtcaaccca gagaatggaa gagtccaatg    7560
ggaagctgca aagctttccg tggagcaggc cctaggtatg atgaatgtcg acggcgaact    7620
gactgccaaa gaactggaga aactgaaaag aataattgac aaactccagg gcctgactaa    7680
ggagcagtgt ttaaactgct agccgccagc gacttgaccc gctgtggtcg cggcggcttg    7740
gttgttactg aaacagcggt aaaaatagtc aaatttcaca accggacctt caccctggga    7800
cctgtgaatt taaagtggc cagtgaggtt gagctaaaag acgcggttga gcacaaccaa    7860
cacccggttg cgagaccgat cgatggtgga gttgtgctcc tgcgttccgc ggttccttcg    7920
cttatagacg tcttgatctc cggtgctgat gcatctccca agttacttgc ccatcacggg    7980
ccgggaaaca ctgggatcga tggcacgctc tgggattttg agtccgaagc cactaaagag    8040
gaagtcgcac tcagtgcgca ataatacag gcttgtgaca ttaggcgcgg cgacgctcct     8100
gaaattggtc tcccttacaa gctgtaccct gttagggta accctgagcg ggtgaaagga    8160
gttctgcaga atacaaggtt tggagacata ccttacaaaa ccccccagtga cactggaagc   8220
ccagtgcacg cggctgcctg ccttacgccc aacgccactc cggtgactga tgggcgctcc    8280
gtcttggcca cgaccatgcc ccccgggttt gagttatatg taccgaccat accagcgtct    8340
gtccttgatt accttgactc taggcctgac tgccctaaac agctgacaga gcacggctgc    8400
gaagatgccg cactgaaaga cctctctaaa tatgacttgt ccacccaagg ctttgtttta    8460
cctggagttc ttcgccttgt gcggaaatac ctgtttgccc atgtaggtaa gtgcccaccc    8520
gttcatcggc cttctactta ccctgctaag aattctatgg ctggaataaa tgggaacagg    8580
ttcccaacca aggacattca gagcgtccct gaaatcgacg ttctgtgcgc acaggctgtg    8640
cgagaaaact ggcaaactgt tcacccccttgt actcttaaga acagtattg cgggaagaag    8700
aagactagga ccatactcgg caccaataac ttcatcgcac tagcccaccg agcagtgttg    8760
```

```
agtggtgtta cccagggctt catgaaaaag gcgtttaact cgcccatcgc cctcggaaag    8820
aacaagttta aggagctaca gactccggtc ctgggcaggt gccttgaagc tgatctcgca    8880
tcctgcgatc gatccacgcc tgcaattgtc cgctggtttg ccgccaacct tctttatgaa    8940
cttgcctgtg ctgaagagca tctaccgtcg tacgtgctga actgctgcca cgacttactg    9000
gtcacgcagt ccggcgcagt gactaagaga ggtggcctgt cgtctggcga cccgatcacc    9060
tctgtgtcta acaccattta tagtttggtg atctatgcac agcatatggt gcttagttac    9120
ttcaaaagtg gtcaccccca tggccttctg ttcttacaag accagctaaa gtttgaggac    9180
atgctcaagg ttcaaccect gatcgtctat tcggacgacc tcgtgctgta tgccgagtct    9240
cccaccatgc caaactatca ctggtgggtt gaacatctga atttgatgct ggggtttcag    9300
acggacccaa agaagacagc aataacagac tcgccatcat ttctaggctg tagaataata    9360
aatgggcgcc agctagtccc caaccgtgac aggatcctcg cggccctcgc ctatcacatg    9420
aaggcgagta atgtttctga atactatgcc tcagcggctg caatactcat ggacagctgt    9480
gcttgtttgg agtatgatcc tgaatggttt gaagaacttg tagttggaat agcgcagtgc    9540
gcccgcaagg acggctacag ctttcccggc acgccgttct tcatgtccat gtgggaaaaa    9600
ctcaggtcca attatgaggg gaagaagtcg agagtgtgcg ggtactgcgg ggccccggcc    9660
ccgtacgcta ctgcctgtgg cctcgacgtc tgcatttacc acacccactt ccaccagcat    9720
tgtccagtca caatctggtg tggccatcca gcgggttctg gttcttgtag tgagtgcaaa    9780
tcccctgtag ggaaaggcac aagccctttta gacgaggtgc tggaacaagt cccgtataag    9840
cccccacgga ccgttatcat gcatgtggag cagggtctca ccccccttga tccaggtaga    9900
taccaaactc gccgcggatt agtctctgtc aggcgtggaa ttaggggaaa tgaagttgaa    9960
ctaccagacg gtgattatgc tagcaccgcc ttgctcccta cctgcaaaga gatcaacatg   10020
gtcgctgtcg cttccaatgt attgcgcagc aggttcatca tcggcccacc cggtgctggg   10080
aaaacatact ggctccttca acaggtccag gatggtgatg ttatttacac accaactcac   10140
cagaccatgc ttgacatgat tagggctttg gggacgtgcc ggttcaacgt cccggcaggc   10200
acaacgctgc aattccccgt cccctcccgc accggtccgt gggttcgcat cctagccggc   10260
ggttggtgtc ctggcaagaa ttccttccta gatgaagcag cgtattgcaa tcaccttgat   10320
gttttgaggc ttcttagtaa aactaccctc acctgtctag gagacttcaa gcaactccac   10380
ccagtgggtt ttgattctca ttgctatgtt tttgacatca tgcctcaaac tcaactgaag   10440
accatctgga ggtttggaca gaatatctgt gatgccattc agccagatta cagggacaaa   10500
ctcatgtcca tggtcaacac aacccgtgtg acctacgtgg aaaaacctgt caggtatggg   10560
caggtcctca ccccctacca cagggaccga gaggacgacg ccatcactat tgactccagt   10620
caaggcgcca cattcgatgt ggtcacattg catttgccca ctaaagattc actcaacagg   10680
caaagagccc ttgttgccat caccagggca agacacgcta tctttgtgta tgacccacac   10740
aggcagctgc agggcttgtt tgatcttcct gcaaaaggca cacccgtcaa cctcgcagtg   10800
caccgcgacg ggcagctgat cgtgctggat agaaataaca agaatgcac ggttgctcag   10860
gctctaggca cggggataa atttagggcc acagacaagc gtgttgtaga ttctctccgc   10920
gccatttgtg ctgatctaga agggtcgagc tctccgctcc ccaaggtcgc acacaacttg   10980
ggatttatt tctcacctga tttaacacag tttgctaaac tcccagtaga acttgcacct   11040
cactggcccg tggtgacaac ccagaacaat gaaaagtggc cagatcggct ggttgccagc   11100
cttcgcccta tccataaata cagccgcgcg tgcatcggtg ccggctatat ggtgggccct   11160
```

```
tcggtgtttc taggcactcc tggggtcgtg tcatactatc tcacaaaatt tgttaagggc    11220
gaggctcaag tgcttccgga gacggttttc agcaccggcc gaattgaggt agactgccgg    11280
gaatatcttg atgatcggga gcgagaagtt gctgcgtccc tcccacacgc tttcattggc    11340
gacgtcaaag gcactaccgt tggaggatgt catcatgtca cctccagata cctcccgcgc    11400
gtccttccca aggaatcagt tgcggtagtc ggggtttcaa gccccggaaa agccgcgaaa    11460
gcattgtgca cactgacaga tgtgtacctc ccagatcttg aagcctatct ccacccggag    11520
acccagtcca agtgctggaa aatgatgttg gacttcaaag aagttcgact aatggtctgg    11580
aaagacaaaa cagcctattt ccaacttgaa ggtcgctatt tcacctggta tcagcttgcc    11640
agctatgcct cgtacatccg tgttcctgtc aactctacgg tgtacttgga cccctgcatg    11700
ggccccgccc tttgcaacag gagagtcgtc gggtccaccc actgggggc tgacctcgcg    11760 gtcaccccct tatgattacgg cgctaaaatt atcctgtcta gcgcgtacca tggtgaaatg    11820 cccccccggat acaaaattct ggcgtgcgcg gagttctcgt tggatgaccc agttaagtac    11880
aaacatacct gggggtttga atcggataca gcgtatctgt atgagttcac cggaaacggt    11940
gaggactggg aggattacaa tgatgcgttt cgtgcgcgcc aggaagggaa aatttataag    12000
gccactgcca ccagcttgaa gttttatttt ccccgggcc ctgtcattga accaacttta    12060
ggcctgaatt gaaatgaaat ggggtccatg caaagccttt ttgacaaaat tggccaactt    12120
tttgtggatg ctttcacgga gttcttggtg tccattgttg atatcattat attttttggcc    12180 attttgtttg gcttcaccat cgccggttgg ctggtggtct tttgcatcag attggtttgc    12240
tccgcgatac tccgtacgcg ccctgccatt cactctgagc aattacagaa gatcttatga    12300
ggcctttctt tcccagtgcc aagtggacat tcccacctgg ggaactaaac atccttttggg    12360 gatgctttgg caccataagg tgtcaaccct gattgatgaa atggtgtcgc gtcgaatgta    12420
ccgcatcatg gaaaaagcag ggcaggctgc ctggaaacag gtggtgagcg aggctacgct    12480
gtctcgcatt agtagtttgg atgtggtggc tcattttcag catctagccg ccattgaagc    12540
cgagacctgt aaatatttgg cctcccggct gcccatgcta cacaacctgc gcatgacagg    12600
gtcaaatgta accatagtgt ataatagcac tttgaatcag gtgtttgcta ttttttccaac    12660 ccctggttcc cggccaaagc ttcatgattt tcagcaatgg ttaatagctg tacattcctc    12720
catattttcc tctgttgcag cttcttgtac tcttttttgtt gtgctgtggt tgcgggttcc    12780
aatactacgt actgttttg gtttccgctg gttaggggca attttctttt cgaactcaca    12840
gtgaattaca cggtgtgtcc accttgcctc acccggcaag cagccacaga gatctacgaa    12900 cccgtaggt ctctttggtg caggatagg tatgaccgat gtggggagga cgatcatgac    12960
gagctagggt ttatgatacc gcctggcctc tccagcgaag gccacttgac tagtgtttac    13020
gcctggttgg cgttcttgtc cttcagctac acggcccagt tccatcccga gatattcggg    13080
atagggaatg tgagtcgagt ttatgttgac atcaaacatc aactcatctg cgccgaacat    13140
gacgggcaga acaccacctt gcctcgtcat gacaacattt cagccgtgtt tcagacctat    13200
taccaacatc aagtcgacgg cggcaattgg tttcacctag aatggcttcg tccctcttt    13260 tcctcgtggt tggttttaaa tgtctcttgg tttctcaggc gttcgcctgc aaaccatgtt    13320
tcagttcgag tcttgcagat attaagacca acaccaccgc agcggcaagc tttgctgtcc    13380
tccaagacat cagttgcctt aggcatcgcg actcggcctc tgaggcgatt cgcaaaatcc    13440
ctcagtgccg tacggcgata gggacacccg tgtatgttac catcacagcc aatgtgacag    13500
```

```
atgagaatta tttacattct tctgatctcc tcatgctttc ttcttgcctt ttctatgctt    13560
ctgagatgag tgaaaaggga tttaaggtgg tatttggcaa tgtgtcaggc atcgtggctg    13620
tgtgtgtcaa ttttaccagc tacgtccaac atgtcaagga gtttacccaa cgctccctgg    13680
tggtcgacca tgtgcggttg ctccatttca tgacacctga gaccatgagg tgggcaactg    13740
ttttagcctg tcttttttgcc attctgttgg caatttgaat gtttaagcat gttggagaaa    13800
tgcttgaccg cgggctgttg ctcgcgattg cttttctttgt ggtgtatcgt gccgttctgt    13860
tttgctgtgc tcgccaacgc cagcaacgac agcagctccc atctacagct gatttacaac    13920
ttgacgctat gtgagctgaa tggcacagat tggctagcta acaaatttga ttgggcagtg    13980
gagagttttg tcatctttcc cgttttgact cacattgtct cctatggtgc cctcactacc    14040
agccatttcc ttgacacagt cgctttagtc actgtgtcta ccgccgggtt tgttcacggg    14100
cggtatgtcc taagtagcat ctacgcggtc tgtgccctgg ctgcgttgac ttgcttcgtc    14160
attaggtttg caaagaattg catgtcctgg cgctacgcgt gtaccagata taccaacttt    14220
cttctggaca ctaagggcag actctatcgt tggcggtcgc ctgtcatcat agagaaaagg    14280
ggcaaagttg aggtcgaagg tcatctgatc gacctcaaaa gagttgtgct tgatggttcc    14340
gtggcaaccc ctataaccag agtttcagcg gaacaatggg gtcgtcctta gatgacttct    14400
gtcatgatag cacggctcca caaaggtgc ttttggcgtt ttctattacc tacacgccag    14460
tgatgatata tgccctaaag gtgagtcgcg gccgactgct agggcttctg cacctttga    14520 tcttcctgaa ttgtgcttc accttcgggt acatgacttt cgcgcacttt cagagtacaa    14580
ataaggtcgc gctcactatg ggagcagtag ttgcactcct ttgggggggtg tactcagcca    14640 tagaaacctg gaaattcatc acctccagat gccgtttgtg cttgctaggc cgcaagtaca    14700
ttctggcccc tgcccaccac gttgaaagtg ccgcaggctt tcatccgatt gcggcaaatg    14760
ataaccacgc atttgtcgtc cggcgtcccg gctccactac ggtcaacggc acattggtgc    14820 ccggggttaaa aagcctcgtg ttgggtggca gaaaagctgt taaacaggga gtggtaaacc    14880
ttgtcaaata tgccaaataa caacggcaag cagcagaaga gaaagaaggg ggatggccag    14940
ccagtcaatc agctgtgcca gatgctgggt aagatcatcg ctcagcaaaa ccagtccaga    15000
ggcaagggac cgggaaagaa aataagaag aaaaacccgg agaagcccca ttttcctcta    15060
gcgactgaag atgatgtcag acatcacttt accccctagtg agcggcaatt gtgtctgtcg    15120
tcaatccaga ccgcctttaa tcaaggcgct gggacttgca ccctgtcaga ttcagggagg    15180
ataagttaca ctgtggagtt tagtttgcct acgcatcata ctgtgcgcct gatccgcgtc    15240
acagcatcac cctcagcatg atgggctggc attcttgagg catctcagtg tttgaattgg    15300
aagaatgtgt ggttaacggc actgattgac attgtgcctc taagtcacct attcaattag    15360
ggcgaccgtg tgggggtgag atttaattgg cgagaaccat gcggccgaaa ttaaaaaaaa    15420 aaaaaaaaa aaaaaaaaa aaaaaaaaa a                                      15451
```

<210> SEQ ID NO 18
<211> LENGTH: 22
<212> TYPE: DNA
<213> ORGANISM: synthetic

<400> SEQUENCE: 18

```
gccaacagcg ccagcagctc tc                                                22
```

<210> SEQ ID NO 19
<211> LENGTH: 24

<212> TYPE: DNA
<213> ORGANISM: synthetic

<400> SEQUENCE: 19
gttgatttac gccttgacgc tatg          24

<210> SEQ ID NO 20
<211> LENGTH: 22
<212> TYPE: DNA
<213> ORGANISM: synthetic

<400> SEQUENCE: 20
gtgagctggc tggcacagat tg            22

<210> SEQ ID NO 21
<211> LENGTH: 53
<212> TYPE: DNA
<213> ORGANISM: synthetic

<400> SEQUENCE: 21
gccaacagcg ccagcagctc tcatcttcag ttgatttacg ccttgacgct atg          53

<210> SEQ ID NO 22
<211> LENGTH: 45
<212> TYPE: DNA
<213> ORGANISM: synthetic

<400> SEQUENCE: 22
gttgatttac gccttgacgc tatgtgagct ggctggcaca gattg                   45

<210> SEQ ID NO 23
<211> LENGTH: 74
<212> TYPE: DNA
<213> ORGANISM: synthetic

<400> SEQUENCE: 23
gccaacagcg ccagcagctc tcatcttcag ttgatttaca acttgacgct atgtgagctg   60
gctggcacag attg                                                     74

<210> SEQ ID NO 24
<211> LENGTH: 74
<212> TYPE: DNA
<213> ORGANISM: synthetic

<400> SEQUENCE: 24
gccaacagcg ccagcagctc tcatcttcag ttgatttacg ccttgacgct atgtgagctg   60
gctggcacag attg                                                     74

<210> SEQ ID NO 25
<211> LENGTH: 24
<212> TYPE: DNA
<213> ORGANISM: synthetic

<400> SEQUENCE: 25
ctaccaacat caggtcgatg gcgg          24

<210> SEQ ID NO 26
<211> LENGTH: 24

-continued

```
<212> TYPE: DNA
<213> ORGANISM: synthetic

<400> SEQUENCE: 26
gtcggccgcg acttaccttt agag                                            24
```